(12) United States Patent
Ohe

(10) Patent No.: US 7,541,189 B2
(45) Date of Patent: Jun. 2, 2009

(54) TRANSCRIPTION ACTIVATION COMPLEX AND UTILIZATION THEREOF

(75) Inventor: Norihisa Ohe, Nara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 795 days.

(21) Appl. No.: 10/465,914

(22) PCT Filed: Dec. 17, 2001

(86) PCT No.: PCT/JP01/11062

§ 371 (c)(1),
(2), (4) Date: Jun. 27, 2003

(87) PCT Pub. No.: WO02/053735

PCT Pub. Date: Jul. 11, 2002

(65) Prior Publication Data

US 2006/0216705 A1    Sep. 28, 2006

(30) Foreign Application Priority Data

Dec. 27, 2000 (JP) ............... 2000-398548
Mar. 19, 2001 (JP) ............... 2001-077740

(51) Int. Cl.
*C12N 15/00* (2006.01)
*C12N 15/63* (2006.01)
*C07K 14/00* (2006.01)
*A61K 48/00* (2006.01)

(52) U.S. Cl. .............. 435/455; 530/350; 435/325

(58) Field of Classification Search .............. None
See application file for complete search history.

(56) References Cited

OTHER PUBLICATIONS

R. Gerlai, "Eph receptors and neural plasticity", *Nature Reviews/Neurooscience*, vol. 2, Mar. 2001, pp. 205-209.

Y. Harigaya et al., "Disappearance of Actin-Binding Protein, Drebin, From Hippocampal Synapses in Alzheimer's Disease", *Journal of Neuroscience Research*, vol. 43, 1996, pp. 87-92.

K. Hatanpaa et al., "Loss of Proteins Regulating Synaptic Plasticity in Normal Aging of Human Brain and in Alzheimer Disease", *Journal of Neuropathology and Experimental Neurology*, vol. 58, No. 6, Jun. 1999, pp. 637-643.

T. Hosoya et al., "Defective development of secretory neurons in the hypothalamus of Arnt2-knockout mice", *Genes to Cells*, vol. 6, 2001, pp. 361-374.

A. Yamaki et al., "The Mammalian *Single-Minded* (*SIM*) Gene: Mouse cDNA Structure and Diencephalic Expression Indicate a Candidate Gene for Down Syndrome", *Genomics*, vol. 35, Article No. 0332, 1996, pp. 136-143.

J. Garcia et al., "Impaired Cued and Contextual Memory in NPAS2-Deficient Mice", *Science*, vol. 288, Jun. 23, 2000, pp. 2226-2230.

N. Ooe et al., "Identification of a Novel Basic Helix-Loop-Helix-PAS Factor, NXF, Reveals a Sim2 Competitive, Positive Regulatory Role in Dendritic-Cytoskeleton Modulator Drebrin Gene Expression", *Molecular and Cellular Biology*, vol. 24, No. 2, Jan. 2004, pp. 608-616.

Moffett, Peter, et al., Different transcriptional properties of mSim-1 and mSim-2, FEBS Lett (Jan. 2000), vol. 466, No. 1, pp. 80-86.

Moffett P. et al., The Murine Sim-2 g4ene product inhibits transcription by active repression and functional interference, Mol. Cell Biol. (1997), vol. 17, No. 9, pp. 4933 to 4947.

Swanson Hi, et al., DNA binding specificities and pairing rules of the Ah receptor, ARNT, and SIM proteins, J. Biol. Chem. (1995), vol. 270, No. 44, pp. 26292 to 26302.

*Primary Examiner*—David Guzo
*Assistant Examiner*—Michele K. Joike
(74) *Attorney, Agent, or Firm*—Sughrue Mion, PLLC

(57) ABSTRACT

The present invention provides a complex of the transcription coupling factor of any of ARNT 1 to 3 and the transcription regulatory factor comprising any of the amino acid sequence from the amino acid sequence group comprising for example the amino acid sequences represented by SEQ ID Nos.1 to 3, which is a transcription activating complex having an ability of binding to a DNA region (5'-ACGTG-3', SEQ ID No.16) to which a transcription inhibiting complex of the transcription coupling factor and a Sim2 as a transcription regulatory factor can be bound and having an ability of promoting the transcription of a gene located downstream of the DNA region.

6 Claims, 6 Drawing Sheets

TRANSCRIPTION ACTIVATION COMPLEX AND UTILIZATION THEREOF

TECHNICAL FIELD

The present invention relates to a transcription activation complex and utilization thereof.

BACKGROUND ART

Down's syndrome is one of the most frequent diseases relating to autosomal aberrations. A Down's syndrome patients has the chromosome No.21 in a somatic cell which is not a normal duplicate chromosome but is a trisomy (triplicate), which leads to a mental retardation, abnormal development, heart disease, leukemia, early Alzheimer's disease.

The results of many investigations made so far on the isolation, identification and functional analysis of the causative genes of this disease indicated that (1) the gene of Single-minded 2 (hereinafter designated as Sim2) known as a transcription regulatory factor playing an important role in the development and differentiation of a central nervous system cell is present in a critical region (q22.2) for the Down's syndrome on the human chromosome No.21, that (2) an increased Sim2 gene expression product in a cell is suggested to be a pathogenic component of the Down's syndrome since the Down's syndrome becomes symptomatic even when only this narrow critical region becomes trisomy, and that (3) a transcription inhibiting complex formed as a result of the binding between a transcription coupling factor classified into an ARNT family such as ARNT1 or ARNT2 (hereinafter sometimes referred to as an ARNT family transcription coupling factor) and a Sim2 exhibits an inhibitory action on a CME sequence (5'-ACGTG-3': a core sequence of an element required for the transcription in the midline in the central nervous system, which is the nucleotide sequence of a DNA to which the protein complex of this transcription coupling factor with the Sim2 can be bound), and more typically, an investigation of the Sim2 function for the activity on the transcription of a reporter gene comprising a CME sequence-carrying promoter bound functionally thereto revealed that the Sim2 has a potent inhibitory effect even on the transcription activity of an ARNT family coupling factor which is an auxiliary factor as its binding partner (i.e., transcription coupling factor) and a Sim2/ARNT family transcription coupling factor heterodimer complex (i.e., a transcription inhibiting complex formed as a result of the binding between the ARNT family transcription coupling factor and the Sim2) was revealed to have an inhibitory effect on the CME sequence, and the promotion of the transcription inhibition by this transcription inhibiting complex is now considered to be one of the causes of the Down's syndrome.

Based on the findings discussed above, a transcription activating complex allowing a transcription regulatory factor/ARNT family transcription coupling factor heterodimer complex to exhibit a promotive activity on the CME sequence has been desired to be found and forced to act competitively against the Sim2/ARNT family transcription coupling factor heterodimer complex, whereby achieving an application to the treatment of the Down's syndrome.

DISCLOSURE OF THE INVENTION

We made effort under such a circumstance and finally discovered that the complex of a certain ARNT family transcription coupling factor and a certain transcription regulatory factor has an ability of exerting a promotive activity on the CME sequence, whereby establishing the present invention.

Thus, the invention provides:

1. a complex of the transcription coupling factor of any of ARNT 1 to 3 and the transcription regulatory factor comprising any of the amino acid sequences shown below (hereinafter sometimes referred to as a present amino acid sequences), which is a transcription activating complex (hereinafter sometimes referred to as an inventive transcription activating complex) having an ability of binding to a DNA region (5'-ACGTG-3', SEQ ID No.16) to which a transcription inhibiting complex of a Sim2 as a transcription regulatory factor and the transcription coupling factor can be bound and having an ability of promoting the transcription of a gene located downstream of the DNA region, wherein the amino acid sequences are;

<<Amino Acid Sequence Group>>

(a) the amino acid sequence represented by any of SEQ ID Nos.1 to 3, (b) the amino acid sequence of a protein comprising an amino acid sequence exhibiting an amino acid identity of 90% or more to the amino acid sequence represented by any of SEQ ID Nos.1 to 3 and also having a transcription regulation ability, (c) the amino acid sequence of a protein comprising an amino acid sequence encoded by a DNA which hybridizes under a stringent condition with a DNA consisting of the nucleotide sequence represented by the nucleotide numbers 102 to 2507 in the nucleotide sequence represented by SEQ ID No.4 and also having a transcription regulation ability, (d) the amino acid sequence of a protein comprising an amino acid sequence encoded by a DNA which hybridizes under a stringent condition with a DNA consisting of the nucleotide sequence represented by the nucleotide numbers 51 to 2456 in the nucleotide sequence represented by SEQ ID No.5 and also having a transcription regulation ability, (e) the amino acid sequence a protein comprising an amino acid sequence encoded by a DNA which hybridizes under a stringent condition with a DNA consisting of the nucleotide sequence represented by the nucleotide numbers 35 to 2440 in the nucleotide sequence represented by SEQ ID No.6 and also having a transcription regulation ability;

2. a transformant (hereinafter sometimes referred to as an inventive transformant) obtainable by introducing one or more vectors (hereinafter sometimes generally referred to as present vector) having an ability of producing a transcription activating complex according to above-mentioned 1 into a host cell;

3. a transformant obtainable by introducing a single vector comprising the both of the DNAs shown below or several vectors comprising such DNAs independently into a host cell, wherein the DNAs are:

<<DNAs >>

(1) the DNA comprising a nucleotide sequence encoding the amino acid sequence of the transcription coupling factor of any of ARNT 1 to 3;

(2) the DNA comprising a nucleotide sequence encoding a present amino acid sequence;

4. A transformant according to the above-mentioned 2 or 3 further containing the DNA of a reporter gene comprising a promoter, as being operably connected thereto, said promoter contains DNA region (5'-ACGTG-3', SEQ ID No.16) to which the transcription inhibiting complex of the Sim2 as a transcription regulatory factor and the transcription coupling factor of any of ARNT 1 to 3 can be bound;

5. a method (hereinafter sometimes referred to as an inventive evaluation method) for evaluating an ability of regulating a transcription promoting ability (hereinafter sometimes referred to as a present regulating ability) possessed by a transcription activating complex according to the above-mentioned 1, which comprises:

(1) a first step for bringing a test substance into contact with a transformant according to the above-mentioned 4;

(2) a second step, after the first step, for measuring the expression level of the reporter gene possessed by the transformant or an index value correlating with the level; and, (3) a third step for evaluating the substance for its ability of regulating the transcription promoting ability possessed by the transcription activating complex based on the expression level or the index value correlating with the level measured in the second step;

6. a searching method (hereinafter sometimes referred to as an inventive searching method) comprising a step for selecting a substance having an ability of regulating the transcription promoting ability possessed by the transcription activating complex based on a regulating ability evaluated by the method according to the above-mentioned 5;

7. a therapeutic agent (hereinafter sometimes referred to as an inventive therapeutic agent) containing as an active ingredient a substance searched for by a method according to the above-mentioned 6 or a pharmaceutically acceptable salt thereof;

8. a therapeutic agent according to the above-mentioned 7 which is a Down's syndrome improving agent;

9. a use as a Down's syndrome improving agent a single vector comprising the both of the DNAs shown below or several vectors comprising said DNAs independently, wherein the DNAs are:

<<DNAs >>

(1) the DNA comprising a nucleotide sequence encoding the amino acid sequence of the transcription coupling factor of any of ARNT 1 to 3;

(2) the DNA comprising a nucleotide sequence encoding a present amino acid sequence;

10. a transcription activating complex (hereinafter sometimes referred to as an inventive transcription activating complex 2) containing a protein comprising one member (A or B) among the member I shown below and one member (X or Y) among the member II shown below and a protein comprising the other member (B or A) among the member I shown below and the other member (Y or X) among the member II shown below, the formation of the complex with the both protein being under the control by the ligand, the member I being:

<<Member I>>

(A) a region to which a transcription regulatory factor comprising any of the following amino acid sequences is bound in the transcription coupling factor of any of ARNT 1 to 3; or, (B) a region to which the transcription coupling factor of any of ARNT 1 to 3 is bound in a transcription regulatory factor comprising a present amino acid sequence; the member II being:

<<Member II>>

(X) a DNA binding region of a transcription regulatory factor which is functional in a host cell; or, (Y) a transcription activating region of a transcription regulatory factor which is functional in a host cell;

11. a transcription activating complex according to the above-mentioned 10 wherein the (X) among the member II is bound to a DNA consisting of any of the nucleotide sequences shown below, the DNA sequence group being:

<<DNA Sequence Group>>

(1) the nucleotide sequence of the DNA to which a Gal4 protein is bound (5'-CGGAGGACTGTCCTCCG-3', SEQ ID No.11);

(2) the nucleotide sequence of the DNA to which a Lex protein is bound (5'-TACTGTATGTACATACAGTA-3', SEQ ID No.12);

(3) the nucleotide sequence of the DNA to which a Lac I receptor protein is bound (5'-GAATTGTGAGCGCGCA-CAATTC-3', SEQ ID No.13);

(4) the nucleotide sequence of the DNA to which a tetracyclin receptor protein is bound (5'-TCGAGTTTACCACTC-CCTATCAGTGATAGAGAAAAGTGAAAG-3', SEQ ID No.14); or, (5) the nucleotide sequence of the DNA to which a ZFHD-1 protein is bound (5'-TAATGATGGGCG-3', SEQ ID No.15);

(6) the nucleotide sequence of the DNA to which a transcription inhibiting complex of the transcription coupling factor of any of ARNT 1 to 3 with the Sim2 as a transcription regulatory factor can be bound (5'-ACGTG-3', SEQ ID No.16);

12. a transcription activating complex according to the above-mentioned 10 wherein the (Y) among the member II is derived from any of the following proteins, the proteins being:

<<Proteins>>

(1) a Gal4 protein;

(2) a Lex protein;

(3) a Lac I receptor protein;

(4) a tetracyclin receptor protein;

(5) a ZFHD-1 protein;

(6) a B42 protein;

(7) a protein as a transcription coupling factor of any of ARNT 1 to 3;

(8) a VP16 protein;

13. a transcription activating complex according to the above-mentioned 10 wherein the both proteins formed said complex under the control of a ligand;

14. a transcription activating complex according to the above-mentioned 13 wherein the (B) among the member I has a region to which the ligand is bound;

15. a transformant (hereinafter sometimes referred to as an inventive transformant 2) obtainable by introducing;

(1) one member (a or b) among the member i shown below and one member (x or y) among the member ii shown below;

(2) the other member (b or a) among the member i shown below and the other member (y or x) among the member ii shown below; and;

(3) the member iii shown below, the member i being:

<<Member i>>

(a) the DNA comprising a nucleotide sequence encoding the amino acid sequence of the region to which a transcription regulatory factor comprising a present amino acid sequence is bound in the transcription coupling factor of any of ARNT 1 to 3;

(b) the DNA comprising a nucleotide sequence encoding the amino acid sequence of the region to which the transcription coupling factor of any of ARNT 1 to 3 is bound in the transcription regulatory factor comprising any of the amino acid sequences shown below; the member ii being:

<<Member ii>>

(X) a DNA comprising a nucleotide sequence encoding the amino acid sequence of a DNA binding region of a transcription regulatory factor which is functional in a host cell; or, (Y) a DNA comprising a nucleotide sequence encoding the amino acid sequence of a transcription activating region of a transcription regulatory factor which is functional in a host cell;

the member iii being:

<<Member iii>> a DNA comprising a reporter gene connected to the downstream of the promoter, said promoter contains a DNA to which a DNA binding region comprising the amino acid sequence encoded by the nucleotide sequence of (x) among the member ii can be bound;

16. a transformant according to the above-mentioned 15 wherein the (x) among the member ii is a DNA comprising the nucleotide sequence encoding the amino acid sequence of a protein which binds to the DNA consisting of any of the nucleotide sequences shown below, the nucleotide sequences being:

<<Nucleotide Sequence Group>>

(1) the nucleotide sequence of the DNA to which a Gal4 protein is bound (5'-CGGAGGACTGTCCTCCG-3', SEQ ID No.11);

(2) the nucleotide sequence of the DNA to which a Lex protein is bound (5'-TACTGTATGTACATACAGTA-3', SEQ ID No.12);

(3) the nucleotide sequence of the DNA to which a Lac I receptor protein is bound (5'-GAATTGTGAGCGCGCA-CAATTC-3', SEQ ID No.13);

(4) the nucleotide sequence of the DNA to which a tetracyclin receptor protein is bound (5'-TCGAGTTTACCACTC-CCTATCAGTGATAGAGAAAAGTGAAAG-3', SEQ ID No.14); or, (5) the nucleotide sequence of the DNA to which a ZFHD-1 protein is bound (5'-TAATGATGGGCG-3', SEQ ID No.15);

(6) the nucleotide sequence of the DNA to which a transcription inhibiting complex of the transcription coupling factor of any of ARNT 1 to 3 with the Sim2 as a transcription regulatory factor can be bound (5'-ACGTG-3', SEQ ID No.16);

17. a transformant according to the above-mentioned 15 wherein the (y) among the member ii is derived from a DNA comprising the nucleotide sequence encoding the amino acid sequence of any of the proteins shown below, the proteins being:

<<Proteins>>

(1) a Gal4 protein;
(2) a Lex protein;
(3) a Lac I receptor protein;
(4) a tetracyclin receptor protein;
(5) a ZFHD-1 protein;
(6) a B42 protein;
(7) a protein as a transcription coupling factor of any of ARNT 1 to 3;
(8) a VP16 protein;

18. a use of a transcription activating complex according to the above-mentioned 1 or 10 for a two-hybrid assay;

19. a use of a transformant according to the above-mentioned 3 or 15 for a two-hybrid assay;

20. a receptor binding assay (hereinafter sometimes referred to as an inventive binding assay) comprising the steps:

(1) a step for bringing a transcription activating complex according to the above-mentioned 10 to which a labeled ligand is bound into contact with a test substance; and, (2) a step for an indirect verification of the state of the binding between the transcription activating complex and the test substance by means of monitoring the level of a ligand in a free form or a ligand in a binding form generated as a result of the competition between the labeled ligand and the test substance or an index value correlating with the level; and the like.

BEST MODE FOR CARRYING OUT THE INVENTION

Figure 1:
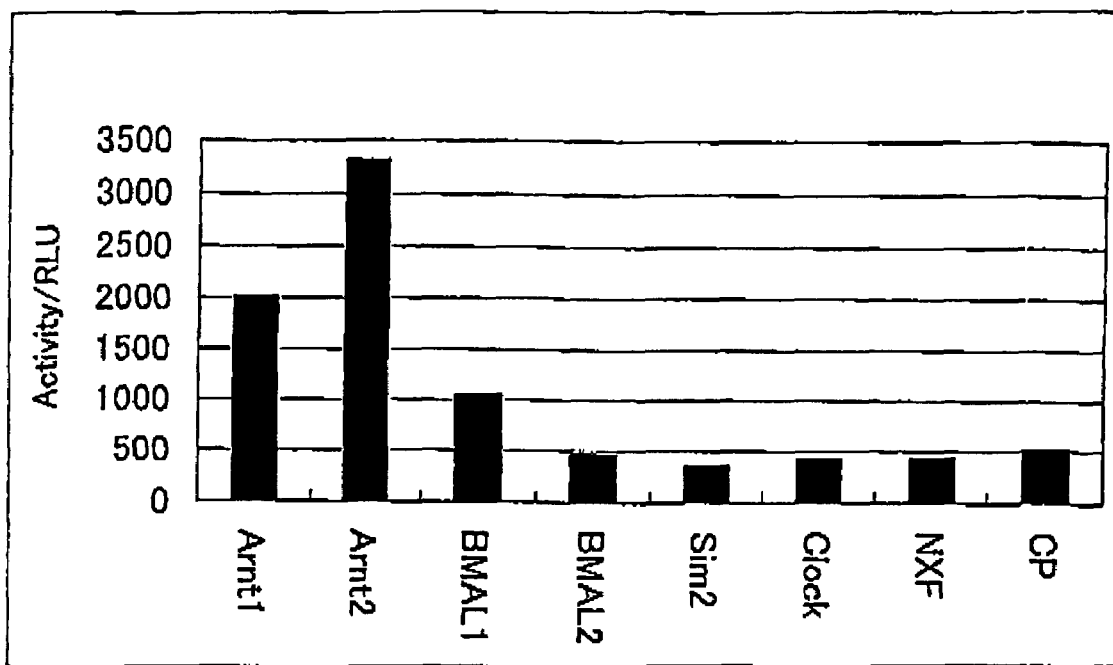
FIG. 1 shows the results of a two-hybrid assay (system employing Gal4-NXF+VP16-X) for verifying the formation of the complex of a present ARNT family transcription coupling factor and a present transcription regulatory factor. The abscissa represents a transcription coupling factor and the like employed in each test system. Those up to the third from the left end are of the present ARNT family transcription coupling factor. Those from the fourth to the sixth from the left end are of the non-present ARNT family transcription coupling factor, which correspond to the test system for comparison. The second from the right end is of a present transcription regulatory factor (NXF) which corresponds to the test system for investigating whether a homodimer is formed or not. The right end is of a CP, which corresponds to the test system for a negative control. The ordinate represents a luciferase activity level, which is an index value representing an activity on the transcription of a reporter gene.

The present invention is further detailed below.

An inventive transcription activating complex is a complex of the transcription coupling factor of any of ARNT 1 to 3 (hereinafter sometimes referred to as a present ARNT family transcription coupling factor) and the transcription regulatory factor (hereinafter sometimes referred to as a present transcription regulatory factor) comprising any of the amino acid sequences shown below (i.e., present amino acid sequences), which is a transcription activating complex having an ability of binding to a DNA region (5'-ACGTG-3', SEQ ID No.16) to which a transcription inhibiting complex of a Sim2 as a transcription regulatory factor and the transcription coupling factor can be bound and having an ability of promoting the transcription of a gene located downstream of the DNA region.

<<Amino Acid Sequence Group>>

(a) the amino acid sequence represented by any of SEQ ID Nos.1 to 3 (the transcription regulatory factor comprising the amino acid sequence represented by SEQ ID No.1 is a present transcription regulatory factor derived from a human and sometimes designated as an hNXF; the transcription regulatory factor comprising the amino acid sequence represented by SEQ ID No.2 is a present transcription regulatory factor derived from a mouse and sometimes designated as an mNXF; and the transcription regulatory factor comprising the amino acid sequence represented by SEQ ID No.3 is a present transcription regulatory factor derived from a rat and sometimes designated as an rNXF);

(b) the amino acid sequence of a protein comprising an amino acid sequence exhibiting an amino acid identity of 90% or more to the amino acid sequence represented by any of SEQ ID Nos.1 to 3 and also having a transcription regulation ability, (c) the amino acid sequence of a protein comprising an amino acid sequence encoded by a DNA which hybridizes under a stringent condition with a DNA consisting of the nucleotide sequence represented by the nucleotide numbers 102 to 2507 in the nucleotide sequence represented by SEQ ID No.4 and also having a transcription regulation ability, (d) the amino acid sequence of a protein comprising an amino acid sequence encoded by a DNA which hybridizes upper a stringent condition with a DNA consisting of the nucleotide sequence represented by the nucleotide numbers 51 to 2456 in the nucleotide sequence represented by SEQ ID No.5 and also having a transcription regulation ability, (e) the amino acid sequence a protein comprising an amino acid sequence encoded by a DNA which hybridizes under a stringent condition with a DNA consisting of the nucleotide sequence represented by the nucleotide numbers 35 to 2440 in the nucleotide sequence represented by SEQ ID No.6 and also having a transcription regulation ability.

A protein forming an inventive transcription activating complex, i.e., a transcription coupling factor of any of ARNT1 to 3 is any ARNT family transcription coupling factor such as an ARNT1, ARNT2 and ARNT3 (identical to BMAL 1). Such a transcription coupling factor is a transcription coupling factor having a high sequence identity when compared with each other. Such a transcription coupling factor forms a transcription inhibiting complex together with a transcription regulatory factor Sim2, whereby possessing an ability of binding the DNA region represented by SEQ ID No.16 (5'-ACGTG-3') and possessing an ability of inhibiting the transcription of a gene located downstream of the DNA region. Among such transcription coupling factors, those exemplified preferably are ARNT1 and ARNT2.

With regard to the other protein which forms an inventive transcription activating complex, the difference from the amino acid sequence represented by SEQ ID No. 1 to 3 observed in the amino acid sequence (i.e., present amino acid sequence) of the "transcription regulatory factor comprising any of the amino acid sequences shown below" may for example be the amino acid deletion, substitution, modification and addition. Any of such difference may be a variation introduced artificially by means of a site-directed mutagenesis and a mutagenic treatment, as well as a naturally occurring polymorphic variation such as a difference in the amino acid sequence due to the difference between the animal species, individuals, organs and tissues.

In the invention, the "amino acid identity" means an identity and a homology in the amino acid sequence between two proteins. The "amino acid identity" described above can be determined by comparing two amino acid sequence which are aligned optimally over the entire range of a reference amino acid. A reference protein here may have an addition or deletion (for example, a gap) in the optimal alignment of the two amino acid sequences. Such an amino acid identity can be calculated for example by producing an alignment utilizing a Clustal W algorism [Nucleic Acid Res., 22 (22): 4673-4680 (1994)] using a Vector NTI. The amino acid identity can be investigated also by using a sequence analysis software, typically Vector NTI, GENETYX-MAC or any other analytical tools provide DNA public database.

A preferred amino acid identity in the invention may for example be 90% or higher.

A "DNA which hybridizes under a stringent condition" described above may for example be a DNA capable of maintaining a hybrid, which was formed previously as a DNA-DNA hybrid by a hybridization at 65° C. at a high ion concentration [for example using 6×SSC (900 mM sodium chloride, 90 mM sodium citrate)], even after washing for 30 minutes at 65° C. at a low ion concentration [for example using 0.1×SSC (15 mM sodium chloride, 1.5 mM sodium citrate)].

The transcription regulating ability in the invention can be evaluated for example based on the assay employing a reporter gene described below.

First, a transformant is produced by introducing into a host cell a reporter gene connected to the downstream of a transcription controlling DNA containing a DNA region (5'-ACGTG-3', SEQ ID No.16; hereinafter sometimes referred to as a present responsive DNA region) to which a transcription inhibiting complex of a Sim2 as a transcription regulatory factor and a present transcription coupling factor can be bound and a gene comprising a nucleotide sequence encoding the amino acid sequence of a test transcription regulatory factor, and then the expression level of the reporter gene possessed by the transformant or an index value correlating with the level is measured, and then based on the expression level or the index value correlating with the level thus measured the transcription regulating ability possessed by the test transcription regulatory factor to be tested is evaluated.

The transcription regulating ability described above may for example be an ability of promoting or inhibiting the transcription of a gene (which means a reporter gene in the case of an assay employing a reporter gene described above) located downstream of the DNA region.

A reporter gene in an evaluation method described above may for example be a luciferase gene, secretor alkaline phosphatase gene, β-galactosidase gene, chloramphenicol acetyl transferase gene, growth factor gene and the like, with a gene encoding a reporter protein which is relatively stable in a host cell being preferred.

First, a transformant is obtained by introducing a reporter gene connected to the downstream of a transcription controlling region containing a present ARNT family transcription coupling factor and a present responsive DNA region and a gene comprising a nucleotide sequence encoding the amino acid sequence of a test transcription regulatory factor (hereinafter sometimes referred to as a test transcription regulatory factor gene) into a host cell (for example, HeLa Cell, CV-1 cell, Hepa1 cell, NIH3T3 cell, HepG2 cell COS1 cell, BF-2 cell, CHH-1 cell and the like). In this procedure, the test transcription regulatory factor gene as being integrated into a basic vector operably connected to a promoter which is functional in the host cell may be introduced into the host cell. The reporter gene connected to the downstream of a transcription controlling region containing the present responsive DNA region may also be employed as being integrated into the basic vector. It is also possible that a vector into which a reporter gene connected to the downstream of a transcription controlling region containing a present responsive DNA region has been integrated and a vector comprising a test transcription regulatory factor gene operably connected to a promoter which is functional in a host cell may be introduced into the host cell together with a vector comprising a marker gene. Then, the cell is incubated usually for several weeks, and then the intended transformant is selected based on the expression level of the introduced marker gene, whereby obtaining a transformant yielding by introducing into the host cell the reporter gene connected to the downstream of the transcription controlling region containing the present responsive DNA region and the test transcription regulatory factor gene operably connected to the promoter which is functional in the host cell.

As used herein, the "promoter which is functional in the host cell" may for example be an inducible promoter such as a GAL1 promoter or a routinely expressed promoter such as an ADH1 promoter (the ADH1 promoter can be prepared by a standard genetic engineering method for example from an yeast expression vector pAAH5 comprising an ADH1 promoter and terminator [available from Washington Research Foundation, Ammerer et al., Method in Enzymology, 110 part (p. 192-201)]; the ADH1 promoter is encompassed in the U.S. patent application Ser. No. 299,733 by Washington Research Foundation, and should be used industrially or commercially in United States only after obtaining the approval from the claimant) when a host cell is a budding yeast cell. When the host cell is an animal cell, then a Rous sarcoma virus (RSV) promoter and cytomegalovirus (CMV) promoter may be mentioned. The transcription controlling region may for example be a DNA consisting of a minimum TATA box sequence derived from a gene capable of being expressed in a host cell, which is the minimum promoter which is capable of functioning in the host cell, typically a DNA comprising a TATA box and a nucleotide sequence consisting of about 50 nucleotides near the transcription initiation point.

A transformant thus prepared may be cultured for example for several hours to several days, and then the expression level of the reporter gene possessed by the transformant or an index value correlating with the level is measured. When the test transcription regulatory factor is activated by the present responsive DNA region, then the transcription of the reporter gene is promoted, and the reporter protein encoded by this reporter gene is accumulated in the cell of the transformant or secreted into the culture medium. By measuring the expression level of this reporter gene or the index value correlating with the level, the expression level of the reporter gene or the index value correlating with the level per cell of the transformant is measured. Typically, when a luciferase gene is employed as a reporter gene, a crude cell extract prepared from the transformant is combined with luciferrin which is a substrate for the luciferase, whereby allowing a luminescence to be emitted at an intensity in proportion with the luciferase level in this crude cell extract. Accordingly, by measuring this luminescence using a measuring device such as a luminometer, the luciferase level, and thus the luciferase gene expression level, can be determined. Similarly, the expression level of the reporter gene or an index value correlating with the level in a transformant (i.e., a control transformant) which contains the reporter gene connected to the downstream of the transcription controlling region containing the present responsive DNA region but does not contain the test transcription regulatory factor gene is measured and this measured value is compared with the expression level of the reporter gene or the index value correlating with the level described above, whereby evaluating the transcription regulating ability possessed by the test transcription regulatory factor gene.

An inventive transcription activating complex can be obtained by culturing an inventive transformant and then recovering the product, which is (1) an inventive transcription activating complex or (2) a present ARNT family transcription coupling factor plus a present transcription activating factor, from the culture, while many cases utilize the inventive transcription activating complex in the form of a transformant which expresses the inventive transcription activating complex.

An inventive transcription activating complex can be produced by introducing one or more vectors (i.e., present vectors) having an ability of producing an inventive transcription activating complex into a host cell. Typically, a single vector comprising the both of the DNAs, namely, (1) the DNA comprising a nucleotide sequence encoding the amino acid sequence of the transcription coupling factor of any of ARNT 1 to 3 and (2) the DNA comprising a nucleotide sequence encoding a present amino acid sequence simultaneously, or several vectors comprising such DNAs independently may be introduced into a host cell.

Any conventional introducing process may be used to introduce present vectors into a host cell depending on the host cell. For the introduction into an *E. coli* host cell, any conventional method may be used, for example, including calcium chloride method and electroporation method as disclosed in the text (J. Sambrook, E. F. Frisch, and T. Maniatis, Molecular Cloning 2nd edition, Cold Spring Harbor Laboratory Press, 1989). The introduction of the vector into a mammal host cell or an insect host cell may be performed according to any general gene transfection method such as calcium phosphate method, DEAE dextran method, electroporation method, and lipofection method. For the introduction into an yeast host cell, for example, Yeast transformation kit (Clontech) may be used based on lithium method.

The introduction of the viral genome into the host cell via the viral vector can be made not only by any of the above general gene transfection methods but also by infecting the host cell with viral particles which carry viral genome containing the both of the DNAs described above.

In order to select an inventive transformant, for example, a marker gene may be introduced into a host cell together with a present vector, and then the host cell may be cultured by any method depending on the characteristic of the marker gene. For example, the marker gene may be a drug resistance gene against a selection drug that has killing activity on the host cell, and the present vector-containing host cell may be cultured in a medium that contains the selection drug. Examples of the combination of the drug resistance gene and the selection drug include the combinations of a neomycin resistance gene and neomycin, a hygromycin resistance gene and hygromycin, and a blasticidin S resistance gene and blasticidin S. Alternatively, the marker gene may complement auxotrophy of the host cell, and the present vector-containing cell may be cultured in a minimal medium free of the nutrient concerning the auxotrophy. When the present vector is introduced into a host cell capable of expressing the both of the DNAs described above, DNA binding activity may be detected.

For example, the inventive transformant in which the both of the DNAs described above are located in the chromosome of the host cell is obtained as follows. The present vector and the marker-containing vector are each digested with a restriction enzyme or the like into a linear chain and then introduced into the host cell by any method as described above. The cell is cultured generally for several weeks and then selected based on the expression amount of the introduced marker gene to give a desired transformant. For example, the present vector which contains the drug resistance gene as the marker gene is introduced into the host cell by any method as described above. The cell is subcultured in a selection drug-containing medium for at least several weeks, and then the drug-resistant clone surviving in the form of a colony is subjected to pure culture, resulting in the inventive transformant in which the both of the DNAs described above are incorporated in the chromosome of the host cell. In order to confirm the incorporation of the inventive gene in the host cell chromosome, the genome DNA may be prepared from the cell by a conventional genetic engineering method, and then the both of the DNAs described above may be detected in the prepared genome DNA by PCR, Southern hybridization, or the like using a DNA comprising a partial nucleotide sequence of the introduced DNAs described above as a primer or a probe. The transformant can be stored in a frozen state and then allowed to awake as needed. Therefore, not every experiment needs the transformant preparation, and tests can be performed using the transformant with the characteristics and the handling conditions checked in advance.

By culturing the inventive transformant thus obtained and then recovering the product, which is (1) an inventive transcription activating complex or (2) a present ARNT family transcription coupling factor and a present transcription activating factor, from the culture, whereby producing an inventive transcription activating complex.

For example, the inventive transformant is a microorganism, and in such a case, the transformant may be cultured using any medium that appropriately contains any carbon source, any nitrogen source, any organic or inorganic salt, and the like each for general microorganism culture. The cultivation may be carried out according to any conventional method for general microorganisms, such as solid culture method and liquid culture method (such as rotary shaking culture, reciprocal shaking culture, jar fermenter culture, and tank culture). The culture temperature and the pH of the medium can be each selected from a certain range in which the microorganism can grow. For example, the culture is generally performed at a temperature of about 15° C. to about 40° C. at a pH of about 6 to about 8. The culture time period depends on various culture conditions but is generally from about one day to about five days. When the expression vector contains an inducible promoter such as a temperature-inducible promoter and an IPTG-inducible promoter, the induction time is preferably within one day and generally several hours.

On the other hand, the transformant may be an animal cell such as a mammal cell and an insect cell, and the transformant may be cultured using any medium for general cell culture. If the transformant is prepared using the selection drug, the culture is preferably performed in the presence of the selection drug. For example, the mammal cell may be cultured using a DMEM medium (Nissui) containing FBS at a final content of 10% at 37° C. under 5% CO2 while the medium may be replaced with fresh one every several days. After the cells are grown in a confluent state, for example, an about 0.25% (w/v) trypsin-containing PBS solution is added so that the cells are separated and dispersed. The cells are then diluted several times and inoculated into a new plate and further cultured. Similarly, the insect cell may be cultured using any insect cell culture medium such as a 10% (v/v) FBS and 2% (w/v) Yeastlate-containig Grace's medium at a culture temperature of 25° C. to 35° C. If the cell tends to peel off the plate as in the case of Sf21 cell, the cells may be dispersed by pipetting and subcultured without using the trypsin solution. When the transformant contains the virus vector such as baculovirus, the culture is preferably terminated before the cell is killed and the cytoplasmic effect is observed, for example, up to 72 hours after the viral infection.

The product, which is (1) an inventive transcription activating complex or (2) a present ARNT family transcription coupling factor and a present transcription activating factor, produced by the inventive transformant may be recovered from the culture by any appropriate combination of conventional isolation or purification processes. For example, after the culture is completed, the transformant cells are collected by centrifugation or the like, and the collected cells are suspended in a general buffer such as a buffer comprising 20 mM HEPES pH7, 1 mM EDTA, 1 mM DTT, and 0.5 mM PMSF and then homogenized in a Polytron, a ultrasonic apparatus, a Dounce homogenizer, or the like. The resulting homogenate may be ultracentrifuged at several tens thousand×g for several tens minutes to about one hour, and then the supernatant fraction may be taken to give a fraction containing (1) an inventive transcription activating complex or (2) a present ARNT family transcription coupling factor and a present transcription activating factor. In addition, the supernatant fraction may be subjected to any type of chromatography such as ion exchange, hydrophobic, gel filtration, or affinity chromatography to give (1) an inventive transcription activating complex or (2) a present ARNT family transcription coupling factor and a present transcription activating factor in a further purified state. In this process, the fraction containing the inventive transcription activating complex or the like may be identified by a DNA binding assay or the like using a probe of an oligonucleotide with a length of about 15 bp to about 200 bp including a present responsive DNA region.

The resulting inventive transcription activating complex may be used in a receptor binding assay or the like for evaluating the ability or the amount of any test substance to bind to or bound to the transcription activating complex.

A DNA (hereinafter sometimes referred to as a present transcription regulatory factor DNA) encoding a transcription regulatory factor comprising a present amino acid sequence (i.e., a present transcription regulatory factor), which forms an inventive transcription activating complex, may be obtained for example from a tissue of an animal such as human, mouse, rat and the like in accordance with a genetic engineering method described for example in J. Sambrook, E. F. Frisch, T. Maniatis, Molecular Cloning, 2nd Edition, Cold Spring Harbor Laboratory (1989).

Typically, a total RNA derived from a tissue of an animal such as human, mouse and rat is first prepared. For example, a brain tissue is pulverized in a solution containing a protein denaturant such as guanidine hydrochloride or guanidine thiocyanate, and then the pulverized material is treated with phenol, chloroform and the like, to denature the protein. The denatured protein is removed for example by a centrifugation to obtain a supernatant, from which the total RNA is extracted by a guanidine hydrochloride/phenol method, SDS-phenol method, guanidine thiocyanate/CsCl method and the like. A commercially available kit based on the methods described above may for example be ISOGEN (NIPPON GENE). The resultant total RNA is used as a template and an oligo dT primer is annealed to a poly A sequence of the RNA, whereby synthesizing a single-stranded cDNA using a reverse transcriptase. Then, the synthesized single-stranded cDNA is used as a template together with a primer which is an RNA obtained by inserting a nick and a gap into the RNA chain using an E. coli RnaseH, whereby synthesizing a double-stranded cDNA using an E. coli DNA polymerase I. Subsequently, the both ends of the synthesized double-stranded cDNA is made blunt using a T4 DNA polymerase. The double-stranded cDNA having both blunt ends is purified and recovered by means of a standard procedure such as a phenol-chloroform extraction and ethanol precipitation. A commercially available kit based on the methods described above may for example be a cDNA synthesis system plus (Amarsham Pharmacia Biotech) or a TimeSaver cDNA synthesis kit (Amarsham Pharmacia Biotech). Then the resultant double-stranded cDNA is ligated to a vector such as a plasmid pUC118 or phage lgt10 using a ligase to prepare a cDNA library. As such a cDNA library, a commercially available cDNA library (GIBCO-BPL or Clontech) may also be employed.

Alternatively, a genomic DNA may be prepared from a tissue sample of an animal such as human, mouse and rat in accordance with a standard method described for example in J. Sambrook, E. F. Frisch, T. Maniatis, Molecular Cloning, 2nd Edition, Cold Spring Harbor Laboratory (1989), or M. Muramatsu, "Labomanual genetic engineering" (Maruzen, 1988). For example, when the sample is a hair, 2 or 3 hairs are washed with a sterilized water and then with ethanol, cut into 2 to 3 mm pieces, which are combined with 200 ml of a BCL-Buffer [10 mM Tris-HCl (pH7.5), 5 mM MgCl2, 0.32 sucrose, 1 Triton X-100] followed by a Proteinase K at the final concentration of 100 ml/ml and SDS at the final concentration of 0.5 (w/v). The mixture thus obtained is incubated at 70° C. for 1 hour, and then subjected to a phenol/chloroform extraction to obtain a genomic DNA. When the sample is a peripheral blood, the sample is treated using a DNA-Extraction kit (Stratagene) and the like to obtain a genomic DNA. The resultant genomic DNA is ligated to a vector such as a lgt10 using a ligase to obtain a genomic DNA library. As such a genomic DNA library, a commercially available genomic DNA library (Stratagene) may also be employed.

From a cDNA library or genomic DNA library obtained as described above, an inventive DNA can be obtained for example by a polymerase chain reaction (hereinafter abbreviated as PCR) using as a primer an oligonucleotide comprising a partial nucleotide sequence of the nucleotide sequence represented by SEQ ID No.4, 5, 6 or 59 (or 60) or the nucleotide sequence complementary to said partial nucleotide sequence or by a hybridization method using as a probe a DNA comprising the nucleotide sequence represented by SEQ ID No.4, 5, 6 or 59 (or 60) or a partial nucleotide sequence of said partial nucleotide sequence.

A primer employed in a PCR may for example be an oligonucleotide having a length of about 10 nucleotides to about 50 nucleotides which is an oligonucleotide comprising a nucleotide sequence selected from a 5' non-translation region of the nucleotide sequence represented by SEQ ID No.4, 5, 6 or 59 (or 60) and which is an oligonucleotide comprising the nucleotide sequence complementary to a nucleotide sequence selected from a 3' non-translation region of the nucleotide sequence represented by SEQ ID No.4, 5, 6 or 59 (or 60). Typically, the forward primer may for example be the oligonucleotide consisting of the nucleotide sequence represented by SEQ ID NO.7 and the oligonucleotide consisting of the nucleotide sequence represented by SEQ ID NO.8. The reverse primer may for example be the oligonucleotide consisting of the nucleotide sequence represented by SEQ ID NO.9 and the oligonucleotide consisting of the nucleotide sequence represented by SEQ ID NO.10. An example of the PCR condition involves an incubation in 50 ml of a reaction solution containing 5 ml of a 10-fold diluted buffer for a LA-Taq polymerase (Takara), 5 ml of a 2.5 mM dNTP mixture (each 2.5 mM dATP, dGTP, dCTP and dTTP) (the final concentration of each of dATP, dGTP, dCTP and dTTP is 0.25 mM), each 0.25 to 1.25 ml of 20 mM primers (final concentration of 0.1 to 0.5 mM), 0.1 to 0.5 mg of a template cDNA and 1.25 units of a LA-Taq polymerase (Takara) for 1 minutes at 95° C. followed by 3 minutes at 68° C. in a single cycle, the cycle being repeated 35 times.

A probe employed in a hybridization method may for example be the DNA consisting of the nucleotide sequence represented by the nucleotide numbers 102 to 2507 in the nucleotide sequence represented by SEQ ID No.4, a DNA consisting of the nucleotide sequence represented by the nucleotide numbers 51 to 2456 in the nucleotide sequence represented by SEQ ID No.5, a DNA consisting of the nucleotide sequence represented by the nucleotide numbers 35 to 2440 in the nucleotide sequence represented by SEQ ID No.6, a DNA consisting of the nucleotide sequence represented by the nucleotide numbers 1419 to 6164 in the nucleotide sequence represented by SEQ ID No.59 and the like. An example of the hybridization condition involves an incubation at 65° C. in the presence of 6×SSC (0.9M sodium chloride, 0.09M sodium citrate), 5× Denhart's solution (0.1 (w/v) ficoll 400, 0.1 (w/v) polyvinyl pyrrolidone), 0.1 (w/v) BSA), 0.5 (w/v) SDS and 100 mg/ml denatured salmon sperm DNA followed by an incubation at room temperature for 15 minutes in the presence of 1×SSC (0.15M sodium chloride, 0.015M sodium citrate) and 0.5 (w/v) SDS, followed by an incubation at 68° C. for 30 minutes in the presence of 0.1×SSC (0.015M sodium chloride, 0.0015M sodium citrate) and 0.5 (w/v) SDS. Alternatively, an incubation at 65° C. in the presence of 5×SSC, 50 mM HEPES, pH7.0, 10× Denhart's solution and 20 mg/ml denatured salmon sperm DNA followed by an incubation at room temperature for 30 minutes in 2×SSC, followed by an incubation at 65° C. for 40 minutes in 0.1× SSC, which is repeated twice, may also be exemplified.

A present transcription regulatory factor DNA can be prepared also by performing a chemical synthesis of a nucleic acid in accordance with a standard method such as a phosphite triester method (Hunkapiller, M. et al., Nature, 310, 105, 1984) based on the nucleotide sequence represented by SEQ ID NO.4, 5, 6 or 59 (or 60).

A present transcription regulatory factor DNA thus obtained can be cloned into a vector in accordance with a genetic engineering method described in J. Sambrook, E. F. Frisch, T. Maniatis, Molecular Cloning, 2nd Edition, Cold Spring Harbor Laboratory (1989). Typically, the cloning can for example be performed using a TA cloning kit (Invitrogen) or a commercially available plasmid vector such as pBluescriptII (Stratagene).

The nucleotide sequence of a resultant present transcription regulatory factor DNA can be identified by a Maxam Gilbert method (described for example in Maxam, A. M. & W. Glibert, Proc. Natl. Acad. Sci. USA, 74, 560, 1997) or a Sanger method (described for example in Sanger, F. & A. R. Coulson, J. Mol. Biol., 94, 441, 1975, Sanger, F. & Nicklen and A. R. Coulson., Proc. Natl. Acad. Sci. USA, 74, 5463, 1997).

A typical example of a present transcription regulatory factor DNA may for example be the DNA consisting of the nucleotide sequence represented by the nucleotide numbers 102 to 2507 in the nucleotide sequence represented by SEQ ID No.4, a DNA consisting of the nucleotide sequence represented by the nucleotide numbers 51 to 2456 in the nucleotide sequence represented by SEQ ID No.5, a DNA consisting of the nucleotide sequence represented by the nucleotide numbers 35 to 2440 in the nucleotide sequence represented by SEQ ID No.6, a DNA consisting of the nucleotide sequence represented by the nucleotide numbers 1419 to 6164 in the nucleotide sequence represented by SEQ ID No.59 and the like.

A present transcription regulatory factor DNA vector can be constructed by integrating a present transcription regulatory factor DNA, in accordance with a standard genetic engineering method, into a vector capable of being utilized in a host cell to which said gene is introduced (hereinafter referred to as a basic vector), such as a vector which contains a gene information capable of being replicated in the host cell, which can independently be proliferated, which can be isolated and purified from the host cell and which has a detectable marker.

A basic vector which can be employed for constructing a present transcription regulatory factor DNA vector may for example be a plasmid pUC119 (Takara) or phagimid pBluescriptII (Stratagene) when using a coliform as a host cell. When using a budding yeast as a host cell, then plasmids pGBT9, pGAD242, pACT2 (Clontech) may be exemplified. When using a mammalian cell as a host cell, a vector containing an autonomous replication origin derived from a virus such as pRc/RSV, pRc/CMV (Invitrogen), bovine papilloma virus plasmid pBV (Amarsham Pharmacia Biotech) or EB virus plasmid pCEP4 (Invitrogen) and a virus such as a vaccinia virus may be exemplified, while an insect virus such as a baculovirus may be exemplified when using a insect cell as a host cell. When the autonomous replication origin-containing vector such as the plasmid pACT2 for the yeast, the bovine papilloma virus plasmid pBPV, and the EB virus plasmid pCEP4 is used to form an inventive vector (or a present vector), the vector introduced in the host cell is held in the form of an episome in the cell.

In order to integrate a present transcription regulatory factor DNA into a virus such as a baculovirus or vaccinia virus, a transfer vector containing a nucleotide sequence homologous to the genome of a virus to be employed can be used. Such a transfer vector is typically a plasmid available from Pharmingen such as pVL1372, pVL1393 (Smith, G. E., Summers M. E. et al., Mol. Cell Biol., 3, 2156-2165 (1983) and pSFB5 (Funahashi, S. et al., J. Virol., 65, 5584-5588 (1991). When a present transcription regulatory factor DNA is inserted into a transfer vector described above and the transfer vector and the genome of a virus are introduced into a host cell simultaneously, a homologous recombination occurs between the transfer vector and the genome of the virus, whereby obtaining a virus into whose genome the present transcription regulatory factor DNA is integrated. The genome of a virus may be the genome for example of Baculovirus, Adenovirus, Vacciniavirus and the like.

More specifically, a present transcription regulatory factor DNA is integrated for example into a baculovirus by inserting the present transcription regulatory factor DNA into a multiple cloning site of a transfer vector such as pVL1393 or pBL1392 followed by introducing the DNA of said transfer vector and a baculovirus genome DNA (Baculogold; Pharmingen) into an insect cell line Sf21 (available from ATCC) for example by a calcium phosphate method followed by incubating the resulting cell. A virus particle containing the genome of the virus into which the present transcription regulatory factor DNA has been inserted is recovered from the culture medium for example by a centrifugation, and then made free from proteins using phenol and the like, whereby obtaining the genome of the virus containing the present transcription regulatory factor DNA. Subsequently, the genome of said virus is introduced into a host cell having a virus particle forming ability such as an insect cell line Sf21 for example by a calcium phosphate method and the resultant cell is incubated, whereby proliferating the virus particle containing the present transcription regulatory factor DNA.

On the other hand, a relatively small genome such as that of a mouse leukemia retrovirus can directly be integrated with a present transcription regulatory factor DNA without using any transfer vector. For example, a virus vector DC(X) (Eli Gilboa et al., BioTechniques, 4, 504-512 (1986)) is integrated with a present transcription regulatory factor DNA on its cloning site. The resultant virus vector into which the present transcription regulatory factor DNA has been integrated is introduced into a packaging cell such as an Ampli-GPE (J. Virol., 66, 3755 (1992)), whereby obtaining a virus particle containing the genome of the virus into which the present transcription regulatory factor DNA has been inserted.

A promoter capable of functioning in a host cell is operably connected to the upstream of a present transcription regulatory factor DNA and then integrated into a basic vector such as those described above, whereby constructing a present transcription regulatory factor DNA capable of allowing the present transcription regulatory factor DNA to be expressed in the host cell. The expression "operably connected" means that a promoter and a present transcription regulatory factor DNA are connected to each other in a condition which allows the present transcription regulatory factor DNA is expressed under the control of the promoter in a host cell into which the present transcription regulatory factor DNA is to be introduced. A promoter capable of functioning in a host cell may for example be a DNA exhibiting a promoter activity in a host cell into which it is to be introduced. Those which may be exemplified when the host cell is a coliform cell are E. coli lactose operon promoter (lacP), tryptophan operon promoter (trpP), arginine operon promoter (argP), galactose operon promoter (galP), tac promoter, T7 promoter, T3 promoter, λ phage promoter (λ-pL, λ-pR) and the like, while those which may be exemplified when the host cell is an animal cell or fission yeast are Rous sarcoma virus (RSV) promoter, cytomegalovirus (CMV) promoter, simian virus (SV40) early or late promoter, mouse mammary tumor virus (MMTV) promoter and the like. Those which may be exemplified when the host cell is a budding yeast are an ADH1 promoter and the like.

When a basic vector which initially possesses a promoter capable of functioning in a host cell is employed, a present transcription regulatory factor DNA may be inserted to the downstream of said promoter so that the vector-possessed promoter and the present transcription regulatory factor DNA are operably connected to each other. For example, each of the plasmids such as pRc/RSV and pRc/CMV described above is provided with a cloning site downstream of a promoter capable of functioning in an animal cell, and by inserting a present transcription regulatory factor DNA into said cloning site followed by a introduction into an animal cell, the present transcription regulatory factor DNA can be expressed. Since any of these plasmids has previously been integrated with a SV40 autonomous replication origin, the introduction of said plasmid into a host cell which has been transformed with an SV40 genome from which an ori is deleted, such as a COS cell, leads to an extremely increased number of the intracellular plasmid copies, resulting in a high expression of the present transcription regulatory factor DNA which has been integrated into said plasmid. Also since the plasmid pACT2 for yeast described above possesses an ADH1 promoter, a present transcription regulatory factor DNA vector capable of allowing a present transcription regulatory factor DNA to be expressed highly in a budding yeast such as CG1945 (Clontech) can be constructed by inserting the present transcription regulatory factor DNA into the downstream of the ADH1 promoter of said plasmid or a derivative thereof.

On the other hand, a vector comprising a DNA (hereinafter sometimes referred to as a present ARNT family transcription coupling factor DNA) comprising a nucleotide sequence encoding the amino acid sequence of any of ARNT1 to 3 can be produced by a method similar basically to the method for producing a present transcription regulatory factor DNA describe above except for using the present ARNT family transcription coupling factor DNA instead of the present transcription regulatory factor DNA. In this procedure, the present ARNT family transcription coupling factor DNA can be produced for example by designing a PCR primer pair for a Long PCR comprising the partial nucleotide sequences of the 5' non-translation region and the 3' non-translation region with referring to the nucleotide sequences such as human ARNT1 (accession No. NM_001668), human ARNT2 (accession No. AB002305), human ARNT3 (accession No. D89722) disclosed in a database, followed by a PCR for amplifying, from a human Brain cDNA library, a DNA comprising a full length translation region within the present ARNT family transcription coupling factor gene which is a region of the gene sandwiched between the primer pair.

For producing a single vector simultaneously comprising the both of the DNAs, namely, (1) the DNA comprising a nucleotide sequence encoding the amino acid sequence of the transcription coupling factor of any of ARNT 1 to 3 (i.e., the present ARNT family transcription coupling factor DNA) and (2) the DNA comprising a nucleotide sequence encoding a present amino acid sequence (i.e., the present transcription regulatory factor DNA), the DNA comprising a nucleotide sequence encoding the amino acid sequence of the transcription coupling factor of any of ARNT 1 to 3 and the DNA comprising a nucleotide sequence encoding a present amino acid sequence are integrated simultaneously into an expression vector intended to integrate two genes into an identical plasmid and to express the genes simultaneously, such as a pBI vector (Clontech). It is also possible to produce several vectors comprising both DNAs independently for example by integrating the DNA comprising a nucleotide sequence encoding the amino acid sequence of the transcription coupling factor of any of ARNT 1 to 3 and the DNA comprising a nucleotide sequence encoding a present amino acid sequence independently into several ordinary expression vectors such as a pRC/RSV vector (Invitrogen).

A single vector comprising the both of the DNAs described above or several vectors comprising such DNAs independently can be employed as a Down's syndrome improving pharmaceutical.

An inventive transformant thus produced may be a transformant which contains the DNA of a reporter gene comprising a promoter operably connected thereto which is capable of being activated by an inventive transcription activating complex in addition to a present vector.

Such a transformant can be utilized for example in evaluating a substance for the ability of regulating the transcription promoting ability possessed by an inventive transcription activating complex. For example, a method for evaluating the present regulating ability possessed by a substance may for example be an evaluation method (i.e., an inventive evaluation method) which comprises the steps:

(1) a first step for bringing a test substance into contact with a transformant described above;

(2) a second step, after the first step, for measuring the expression level of the reporter gene possessed by the transformant or an index value correlating with the level; and, (3) a third step for evaluating the substance for its ability of regulating the transcription promoting ability possessed by the transcription activating complex based on the expression level or the index value correlating with the level measured in the second step.

A further application is possible for example to a searching method (i.e., an inventive searching method) comprising a step for selecting a substance having an ability of regulating the transcription promoting ability possessed by the transcription activating complex based on a regulating ability evaluated by the evaluation method and a therapeutic agent (i.e., an inventive therapeutic agent), such as a Down's syndrome improving agent, containing as an active ingredient a substance searched for by such a searching method or a pharmaceutically acceptable salt thereof.

A therapeutic agent (i.e., an inventive therapeutic agent) containing as an active ingredient a substance selected by an inventive searching method or a pharmaceutically acceptable salt thereof can be administered at an effective dose orally or parenterally to a mammalian animal such as human. For example, the inventive therapeutic agent when administered orally can be given in an ordinary form such as a tablet, capsule, syrup and suspension. When the inventive therapeutic agent is given parenterally, it can be administered in an ordinary liquid form such as a solution, emulsion and suspension. A method for administering the inventive therapeutic agent in a form described above parenterally may for example be an injection or a rectal administration of a suppository.

Such a suitable dosage form can be produced by incorporating a substance selected by an inventive searching method or a pharmaceutically acceptable salt thereof into a pharmaceutically acceptable ordinary carrier, excipient, binder, stabilizer, diluent and the like. When employing an injection formulation, it may be possible to add acceptable buffering agents, solubilizing aids, osmotic agents and the like.

The dosage may vary depending on the age and the sex of the mammalian subject, degree of the disease, the type of the inventive therapeutic agent, dosage form and the like, the oral dose is usually about 1 mg to about 2 g as an active ingredient per day in an adult, preferably about 5 mg to about 1 g, while the injection may be given at about 0.1 mg to about 500 mg as an active ingredient in an adult. Such a daily dose may be given all at once or in several portions.

The invention also provides a transcription activating complex or transformant for a two-hybrid assay employing a region required for exerting the transcription promoting ability possessed by an inventive transcription activating complex.

Thus, the invention encompasses (1) an invention relating to a use of an inventive transcription activating complex and an inventive transcription activating complex 2 for a two-hybrid assay, and (2) an invention relating to a use of an inventive transformant and an inventive transformant 2 for a two-hybrid assay. For producing a system for such a two-hybrid assay, a commercial kit, such as Matchmaker Two-hybrid system (Clontech), CheckMate Mammalian Two-Hybrid System (Promega) may be employed.

An inventive transcription activating complex 2 contains a protein comprising one member (A or B) among the member I shown below and one member (X or Y) among the member II shown below and a protein comprising the other member (B or A) among the member I shown below and the other member (Y or X) among the member II shown below, and is a complex formed from the both proteins. It may also be a complex of the both proteins formed under the control by a ligand.

<<Member I>>

(A) A region to which a transcription regulatory factor comprising the present amino acid sequences is bound in the present ARNT family transcription coupling factor; or, (B) A region to which the present ARNT family transcription coupling factor is bound in a transcription regulatory factor comprising the present amino acid sequence.

<<Member II>>

(X) A DNA binding region of a transcription regulatory factor which is functional in a host cell; or, (Y) A transcription activating region of a transcription regulatory factor which is functional in a host cell.

In the invention, a transcription coupling factor comprising (A) in the member I is a transcription coupling factor which recognizes and thus binds to a complex of a present amino acid sequence-carrying transcription regulatory factor with a ligand, and also is a present ARNT family transcription coupling factor.

On the other hand, a transcription regulatory factor comprising (B) in the member I is a transcription regulatory factor comprising a present amino acid sequence which is capable of binding to a transcription coupling factor described above. In such a case, for the purpose of forming a complex with a ligand, the transcription regulatory factor has a region to which the ligand is bound. A DNA comprising a nucleotide sequence encoding the amino acid sequence of such a region is a partial nucleotide sequence of the transcription regulatory factor, such as the nucleotide sequence represented by the nucleotide numbers 132 to 2507 in the nucleotide sequence represented by SEQ ID No.4.

A transcription regulatory factor comprising (X) in the member II may for example be a transcription regulatory factor which binds to a DNA consisting of any of the nucleotide sequence such as the nucleotide sequence of the DNA to which a Gal4 protein is bound (5'-CGGAGGACTGTCCTCCG-3', SEQ ID No.11), the nucleotide sequence of the DNA to which a Lex protein is bound (5'-TACTGTATGTACATACAGTA-3', SEQ ID No.12), the nucleotide sequence of the DNA to which a Lac I receptor protein is bound (5'-GAATTGTGAGCGCGCACAATTC-3', SEQ ID No.13), the nucleotide sequence of the DNA to which a tetracyclin receptor protein is bound (5'-TCGAGTTTACCACTCCCTATCAGTGATAGAGAAAAGTGAAAG-3', SEQ ID No.14), the nucleotide sequence of the DNA to which a ZFHD-1 protein is bound (5'-TAATGATGGGCG-3', SEQ ID No.15), the nucleotide sequence of the DNA to which a transcription inhibiting complex of the transcription coupling factor of any of ARNT 1 to 3 with the Sim2 as a transcription regulatory factor can be bound (5'-ACGTG-3', SEQ ID No.16), and also is a transcription regulating factor which is functional in a host cell. On the other hand, a transcription regulatory factor comprising (Y) in the member II may for example be a transcription regulatory factor capable of functioning in a host cell such as a Gal4 protein, Lex protein, Lac I receptor protein; tetracyclin receptor protein, ZFHD-1 protein, B42 protein, a protein as a present ARNT transcription coupling factor and VP16 protein.

A transcription activating complex consisting of such various member is produced for example by an inventive transformant 2.

With regard to an inventive transformant 2, (a) in the member i means a DNA comprising a nucleotide sequence encoding the amino acid sequence of (A) in the member I, and such a DNA can be prepared by an ordinary genetic engineering method from a gene of a transcription coupling factor comprising (A) in the member I. On the other hand, (b) in the member i means a DNA comprising a nucleotide sequence encoding the amino acid sequence of (B) in the member I, and such a DNA can be prepared by an ordinary genetic engineering method from a gene of a present transcription regulatory factor comprising (B) in the member I.

(x) in the member ii means a DNA comprising a nucleotide sequence encoding the amino acid sequence of (X) in the member II, and such a DNA can be prepared by an ordinary genetic engineering method from a gene of a transcription coupling factor comprising (A) in the member I. On the other hand, (y) in the member ii means a DNA comprising a nucleotide sequence encoding the amino acid sequence of (Y) in the member II, and such a DNA can be prepared by an ordinary genetic engineering method from a gene of a present transcription regulatory factor comprising (Y) in the member II.

The member iii means a DNA comprising a reporter gene connected to the downstream of a promoter containing a DNA to which (X) in the member II can be bound. As used herein, a reporter gene means a reporter gene employed in an ordinary reporter assay such as a luciferase gene, secretor alkaline phosphatase gene, β-galactosidase gene, chloramphenicol acetyl transferase gene, growth factor gene and the like, with gene encoding a reporter protein which is relatively stable in a host cell being preferred. A DNA to which (X) in the member II can be bound may for example be a DNA consisting of any of the nucleotide sequences such as the nucleotide sequence of the DNA to which a Gal4 protein is bound (5'-CGGAGGACTGTCCTCCG-3', SEQ ID No.11), the nucleotide sequence of the DNA to which a Lex protein is bound (5'-TACTGTATGTACATACAGTA-3', SEQ ID No.12), the nucleotide sequence of the DNA to which a Lac I receptor protein is bound (5'-GAATTGTGAGCGCGCACAATTC-3', SEQ ID No.13), the nucleotide sequence of the DNA to which a tetracyclin receptor protein is bound (5'-TCGAGTTTACCACTCCCTATCAGTGATAGAGAAAAGTGAAAG-3', SEQ ID No.14), the nucleotide sequence of the DNA to which a ZFHD-1 protein is bound (5'-TAATGATGGGCG-3', SEQ ID No.15), the nucleotide sequence of the DNA to which a transcription inhibiting complex of the transcription coupling factor of any of ARNT 1 to 3 with the Sim2 as a transcription regulatory factor can be bound (5'-ACGTG-3', SEQ ID No.16).

Each of such various members is combined with each other as appropriate for the expression of an inventive transcription regulatory factor 2 and inserted into a vector, which is then introduced into an identical host cell using an ordinary genetic engineering method, whereby obtaining a present transformant. In such a case, each member may be introduced into an identical host cell (1) in the state where the member iii is kept independent, or (2) in the state where two chimera genes, namely, a chimera gene 1 obtained by ligating one member (a or b) among the member i and one member (x or y) among the member ii with aligning their nucleotide sequence reading frame and a chimera gene 2 obtained by ligating the other member (b or a) among the member i and the other member (y or x) among the member ii with aligning their nucleotide sequence reading frame, are produced and each of these chimera genes 1 and 2 is connected to the downstream of the promoter which is functional in the host cell (such as an inducible promoter such as a GAL1 promoter or a routinely expressed promoter such as an ADH promoter when a host cell is a budding yeast cell). When a utilizable intrinsic reporter gene is possessed by a host cell, then it may be utilized, and in such a case the introduction of a reporter gene can be omitted.

A host cell used for producing an inventive transformant 2 may for example be a budding yeast cell, a mammalian cell such as HeLa cell.

In a present evaluation method, a transformant and a test substance are allowed to be in contact with each other for several hours to several days, typically a transformant is cultured in a medium supplemented with a test substance for several hours to several days, and then the expression level of the reporter gene possessed by the transformant or an index value correlating with the level is measured. When the present transcription activating complex produced by the transformant is activated as a result of the binding of the test substance, the transcription of the reporter gene is promoted, and the reporter protein encoded by this reporter gene is accumulated in the cell of the transformant or secreted into the culture medium. By measuring the expression level of this reporter gene or the index value correlating with the level, the expression level of the reporter gene or the index value correlating with the level per cell of the transformant is measured.

Typically, when a luciferase gene is employed as a reporter gene, a crude cell extract prepared from the transformant which has been brought into contact with a test substance is combined with luciferrin which is a substrate for the luciferase, whereby allowing a luminescence to be emitted at an intensity in proportion with the luciferase level in this crude cell extract. Accordingly, by measuring this luminescence using a measuring device such as a luminometer, the luciferase level, and thus the luciferase gene expression level, can be determined. Similarly, the expression level of the reporter gene or an index value correlating with the level under the conditions involving no contact between the transformant and the test substance is measured, and this measured value is compared with the expression level of the reporter gene or an index value correlating with the level under the conditions involving the contact with the test substance, whereby evaluating the present regulating ability possessed by the test substance.

Based on a present regulating ability evaluated by an evaluation method described above, a substance having the present regulating ability can readily be selected, and a therapeutic agent containing such a substance or a pharmaceutically acceptable salt thereof as an active ingredient can be provided.

A therapeutic agent (i.e., an inventive therapeutic agent) containing as an active ingredient a substance selected by an inventive searching method or a pharmaceutically acceptable salt thereof can be administered at an effective dose orally or parenterally to a mammalian animal such as human. For example, the inventive therapeutic agent when administered orally can be given in an ordinary form such as a tablet, capsule, syrup and suspension. When the inventive therapeutic agent is given parenterally, it can be administered in an ordinary liquid form such as a solution, emulsion and suspension. A method for administering the inventive therapeutic agent in a form described above parenterally may for example be an injection or a rectal administration of a suppository.

Such a suitable dosage form can be produced by incorporating a substance selected by an inventive searching method or a pharmaceutically acceptable salt thereof into a pharmaceutically acceptable ordinary carrier, excipient, binder, stabilizer, diluent and the like. When employing an injection formulation, it may be possible to add acceptable buffering agents, solubilizing aids, osmotic agents and the like.

The dosage may vary depending on the age and the sex of the mammalian subject, degree of the disease, the type of the inventive therapeutic agent, dosage form and the like, the oral dose is usually about 1 mg to about 2 g as an active ingredient per day in an adult, preferably about 5 mg to about 1 g, while the injection may be given at about 0.1 mg to about 500 mg as an active ingredient in an adult. Such a daily dose may be given all at once or in several portions.

A disease for which an inventive therapeutic agent is indicated may for example be a disease related to Down's syndrome such as mental retardation.

The present invention is also directed to a receptor binding assay (the inventive binding assay).

The inventive binding assay enables the measurement of the ability of any chemical substance to bind to the inventive transcription activating complex 2, the quantification of the binding amount, and the analysis of the binding specificity or the binding strength. For example, a labeled ligand is preliminarily allowed to bind to the inventive transcription activating complex 2, which is recovered from the inventive transformant 2 as described above. The test material is then allowed to coexist with the labeled ligand so that the test substance competes with the labeled ligand. Depending on the affinity of each for the inventive transcription activating complex 2, the labeled ligand is released from the complex. The amount of the labeled ligand bound to the complex decreases, and therefore, the amount of the label bound to the complex decreases. Thus, the label amount of the free form or the bound form of the labeled ligand may be monitored to indirectly determine the binding state between the inventive transcription activating complex 2 and the test substance. For example, such a process enables the measurement of the ability of the test substance to bind to the inventive transcription activating complex 2.

The bound and free forms of the labeled ligand may be separated by hydroxyapatite method, glycerol density gradient ultracentrifugation or the like. The reaction system may broadly be classified into three groups. The first group includes a system in which only a solvent is added to the labeled ligand-bound inventive transcription activating complex 2 and corresponds to the system in which the addition amount of the test substance is zero. In this system, the label amount of the bound form of the labeled ligand represents the total amount of the labeled ligand bound to the inventive transcription activating complex 2 (the total binding amount). The second group includes a system in which for example, an unlabeled ligand is added to the labeled ligand-bound inventive transcription activating complex 2 in such a concentration that the inventive transcription activating complex 2 is saturated with the unlabeled ligand so as to have no capacity for binding to the labeled ligand (for example, 10 mM). In this system, the label amount of the bound form of the labeled ligand is determined as the amount of the labeled ligand nonspecifically bound to the inventive transcription activating complex 2 (the nonspecific binding amount). Therefore, the amount of the labeled ligand specifically bound to the inventive transcription activating complex 2 (the specific binding amount) is calculated by subtracting the nonspecific binding amount from the total binding amount. The third group includes a system in which the test substance is added to the labeled ligand-bound inventive transcription activating complex 2 at a final concentration of 10 mM, for example (such a concentration may arbitrarily be altered depending on the purpose). If the test substance has the ability to bind to the inventive transcription activating complex 2, the label amount of the bound form of the labeled ligand obtained in this system will be smaller than the specific binding amount obtained as described above under the condition that the addition amount of the test material is zero. Thus, the binding state between the inventive transcription activating complex 2 and the test substance is indirectly determined. The inventive binding assay may be performed to determine the ability of the test substance to bind to the inventive transcription activating complex 2. If the test substance include different substances, the assay can also determine whether the test substance includes any substance that has an affinity for the inventive transcription activating complex 2. If the ability of the test substance to bind to the inventive transcription activating complex 2 should be evaluated in a more detailed manner, for example, the test substance may be added at different concentrations in the third group in the process of the inventive binding assay. For example, the label amount of the bound form of the labeled ligand may be determined to produce the amounts of the bound and free forms of the ligand, respectively, and then the results may be subjected to the Scatchard analysis so that the binding affinity, the binding specificity, the binding capacity, or the like can be evaluated between the test substance and the inventive transcription activating complex 2.

The invention relating to a reporter assay, the invention relating to a two-hybrid assay and the inventive binding assay can be utilized for detecting a substance as an active ingredient for example in a Down's syndrome improving agent.

EXAMPLES

The present invention is further described in the following Examples, which are not intended to restrict the invention.

Example 1

Preparation of Present Transcription Regulatory Factor (mNXF) and Preparation of pGEM-mNXF as Vector Containing the Same Polynucleotides consisting of the nucleotide sequences represented by SEQ ID NOs.7 and 9 were synthesized using a DNA synthesizer (Applied Biosystems Model 394). Using the polynucleotides thus synthesized as primers together with a template which was 10 ng of a mouse Brain cDNA library (#10655-017, Gibco BRL), a PCR was conducted in which each 10 pmol of the polynucleotide described above was added to 50 µl of the reaction solution, and an LA-Taq polymerase (Takara) and a buffer attached to the kit containing this enzyme were employed. The reaction conditions of this PCR which employed a PCR system 9700 (Applied Biosystems) involved 35 cycles in total, each cycle consisting of an incubation for 1 minutes at 95° C. followed by 3 minutes at 68° C.

Then, the entire volume of the PCR reaction solution thus obtained was subjected to a low melting point agarose gel electrophoresis (agarose L, Nippon Gene) to purify and recover the amplified DNA fragment (about 2.5 kb). A part of the DNA thus purified and recovered was used together with a dye terminator sequence kit FS (Applied Biosystems) to prepare a direct sequencing sample, which was subjected to a direct nucleotide sequencing using an autosequencer (Applied Biosystems, Model 3700).

Subsequently, the amplified DNA (about 1 µg) purified and recovered as described above was mixed with a pGEM T easy vector (Promega) (10 ng), and combined with a T4 DNA Ligase to effect a reaction, whereby obtaining a pGEM-mNXF. The nucleotide sequence of the resultant pGEM-mNXF was determined using an ABI Model 3700 autosequencer by a dye terminator method. The determined nucleotide sequence was compared with the nucleotide sequence obtained by the direct sequencing described above, and it was confirmed that the nucleotide sequence in the translation region exhibited a complete agreement.

Example 2

Tests for Verifying Transcription Promoting Ability of the Inventive Transcription Activating Complex (2-1) Preparation of pGL3-TATA-Galx4 (Construction of Reporter Gene Plasmid into Which 4 Copies of DNA Binding Region of GAL4 as Transcription Regulatory Factor has been Introduced into Upstream of Luciferase Gene Comprising TATA Minimum Promoter)

A pGL3-TATA-Galx4 reporter gene plasmid employed for measuring the transcription regulating ability of a chimera protein of the DNA binding region of GAL4 as a transcription regulatory factor and any optional transcription regulatory factor is one formed by introducing, into the upstream of the luciferase gene comprising a TATA minimum promoter, 4 copies in tandem of a DNA to which the GAL4 DNA binding region can be bound. By measuring the expression level of the luciferase in the case that the chimera protein of the GAL4 DNA binding region and any transcription regulatory factor exerts its effect on the reporter gene plasmid described above, the transcription regulation ability possessed by this chimera protein can advantageously be measured. This pGL3-TATA-Galx4 reporter gene plasmid was prepared as described below.

First, two oligonucleotides each comprising a DNA to which the GAL4 DNA binding region can be bound (SEQ ID No.17: 5'-cgcgtcgagctcgggtcggaggactgtcctccgactgctcgagtc gagctcgggtcggaggactgtcctccgactgctcgaga-3', SEQ ID No.18: 5'-cgcgtctcgagcagtcggaggacagtcctccgacccgagctcgactcgag cagtcggaggacagtcctccgacccgagctcga-3') were hybridized, and phosphorylated at the 5' terminal using a T4 kinase, and then connected in tandem using a T4 Ligase. The resultant double-stranded oligonucleotide was subjected to a low melting point agarose electrophoresis (NuseiveGTG; FMCbio) to recover a DNA fragment in which these double stranded oligonucleotide are connected in tandem. The DNA fragment thus recovered was used as an insert fragment. It was ligated with the pGL3-TATA vector (0.1 µg) which had been cleaved with MluI and then treated with an alkaline phosphatase (BAP C75; Takara) in the presence of a T4 Ligase (Takara) (reaction at 16° C. for 16 hours), whereby obtaining a pGL3-TATA-Galx4 (a reporter gene plasmid formed by introducing, into the upstream of the luciferase gene comprising a TATA minimum promoter, 4 copies of the DNA binding region of GAL4 as a transcription regulatory factor).

(2-2) pRC/RSV-Gal4-DBD Preparation (Construction of Plasmid Expressing DNA Binding Region of GAL4 as Transcription Regulatory Factor)

On the other hand, a pRC/RSV-Gal4-DBD which is a plasmid expressing only the DNA binding region of GAL4 as a transcription regulatory factor (hereinafter sometimes designated as Gal4-DBD, a part lacking the transcriptional control region of GAL4) was prepared as described below.

A pM which is a plasmid comprising a DNA encoding a Gal4-DBD (contained in a commercial kit K1602-1; Clontech) was cleaved with NheI and XbaI, and then made blunt-ended using a T4 polymerase. This was subjected to a low melting point agarose electrophoresis (agarose L: Nippon Gene) to recover a DNA fragment (about 500 bp) encoding a Gal4-DBD. The recovered DNA fragment was employed as an insert fragment.

Then, a pRC/RVS (Invitrogen) was cleaved with HindIII, and made blunt-ended using a T4 polymerase. This was BAP-treated and used as a vector, and this vector (0.1 µg) was ligated with the insert fragment (0.5 µg) described above using a T4 Ligase, whereby obtaining a pRC/RSV-Gal4-DBD). The correct construction of the plasmid for expressing the Gal4-DBD under the control of the RSV promoter was verified using an ABI Model 3700 autosequencer to determine the nucleotide sequence by a dye terminator method.

(2-3) pRC/RSV-MA, pRC/RSV-MB, pRC/RSV-MC Preparation (construction of plasmid in which recognition site of pmaci as restriction enzyme giving blunt end in frame different from each other is introduced into downstream of DNA encoding Gal4-DBD for expressing chimera protein obtained by binding DNA binding region of GAL4 as transcription regulatory factor with transcription activating region of optional transcription regulatory factor)

While each of pRC/RSV-MA, pRC/RSV-MB, pRC/RSV-MC has a translation region of the Gal4-DBD downstream of the RSV promoter, and can be connected, at a further downstream PmaCI cleavage-derived blunt end, with a blunt-ended DNA fragment in such a manner that the translation frame of the DNA encoding the Gal4-DBD is in agreement with the translation frame of the blunt-ended DNA fragment. As a result, a chimera protein in which a GAL4 DNA binding region has been connected to a transcription regulation region of any optional transcription regulatory factor can be expressed.

Specifically, each of the pRC/RSV-MA, pRC/RSV-MB and pRC/RSV-MC was prepared as described below.

First, two oligonucleotides (SEQ ID No.19:5'-agcttcatc-ccacgtgagtcat-3', SEQ ID No.20: 5'-ctagatgactcacgtgggatga-3') were hybridized and then phosphorylated at the 5' terminal using a T4 kinase. This was used as an insert fragment. On the other hand, the pRC/RSV-Gal4-DBD prepared in Section (2-2) described above was used as a vector after the cleavage with HindIII 29dand XbaI followed by the BAP treatment. The both were then ligated using a T4 Ligase, whereby obtaining a pRC/RSV-MA. Similarly, other two nucleotides (SEQ ID No.21: 5'-agcttcatccacacgtgagtcat-3', SEQ ID No.22: 5'-ctagatgactcacgtgtggatga-3') were hybridized and then phosphorylated at the 5' terminal using a T4 kinase, and then was used as an insert fragment, whereby obtaining a pRC/RSV-MB. Similarly, other two nucleotides (SEQ ID No.23: 5'-agcttcatccaacacgtgagtcat-3', SEQ ID No.24: 5'-cta-gatgactcacgtgttggatga-3') were hybridized and then phosphorylated at the 5' terminal using a T4 kinase, and then was used as an insert fragment, whereby obtaining a pRC/RSV-MC.

(2-4) Preparation of pBlue-hArnt1kozac, pBlue-hArnt2kozac, pBlue-hArnt3kozac, pGEM-hBMAL2kozac, pRC/RSV-hSim2kozac and pBlue-hClockkozac (Construction of plasmids required for two-hybrid assay).

(2-4-1) pBlue-hArnt1kozac pBlue-hArnt1kozac which is a plasmid comprising a full length Arnt1 translation region was prepared as described below.

First, from a human liver mRNA (purchased from Clontech), a single stranded cDNA was prepared using a polydT primer (purchased from Amersham Pharmacia) and a reverse transcriptase (SuperScriptII purchased from Gibco). The resultant cDNA was employed as a template together with the forward primer 5'-ggccatggcggcgactactgccaaccccgaaatga-3' (SEQ ID No.25) and the reverse primer 5'-tgagggaagggaagg-gagaggaactttattctgt-3' (SEQ ID No.26) as well as a Pyrobest polymerase (Takara) to perform a PCR to obtain an amplified DNA fragment. The PCR condition involved 35 cycle in total, each cycle being performed at 95° C. for 1 minutes followed by 68° C. for 3 minutes. The amplified DNA thus obtained fragment was subjected to a 500-fold dilution with TE and used as a template together with the forward primer 5'-cccg-gcggccgcccagccaccatggcggcgactactgccaaccccgaaatgacatc-3' (SEQ ID No.27) and the reverse primer 5'-cccgtctagaaccccct-tatcctcaccccaatagttctattctgaa-3' (SEQ ID No.28) as well as a Pyrobest polymerase (Takara) to perform a PCR again to obtain an amplified DNA fragment. The PCR condition involved 35 cycle in total, each cycle being performed at 95° C. for 1 minutes followed by 68° C. for 3 minutes. The amplified DNA thus obtained fragment had a kozac sequence (5'-CCAGCCACC-3') immediately before the initiation codon of a DNA encoding Arnt1 and a NotI restriction enzyme site further upstream thereof. Into the downstream of the stop codon possessed by this amplified DNA fragment, an XbaI restriction enzyme site was further introduced. The resultant amplified DNA fragment was cleaved with the both of the restriction enzymes NotI and XbaI and subjected to a low melting point agarose electrophoresis to purify and recover a DNA fragment. The purified and recovered DNA fragment was employed as an insert fragment.

Subsequently, a pBluescript vector which had been cleaved with NotI and XbaI and then subjected to a BAP treatment was employed as a vector, and this vector (0.1 µg) was ligated with the insert fragment (0.5 µg) described above using a T4 Ligase to prepare a pBlue-hArnt1kozac. The correct construction of this plasmid and the correct nucleotide sequence for the Arnt1-encoding DNA translation part were verified by investigating the nucleotide sequence of the binding part and the nucleotide sequence of the translation part.

(2-4-2) pBlue-hArnt2kozac pBlue-hArnt2kozac which is a plasmid comprising a full length Arnt2-encoding DNA translation region was prepared as described below.

First, from a human Brain mRNA (purchased from Clontech) a single stranded cDNA was prepared using a polydT primer (purchased from Amersham Pharmacia) and a reverse transcriptase (SuperScriptII; purchased from Gibco). The resultant cDNA was employed as a template together with the forward primer 5'-catctctcacctggactgctgtgaccttcattcat-3' (SEQ ID No.29) and the reverse primer 5'-cacatgggcatcga-catcacagtatgggtggcact-3' (SEQ ID No.30) as well as a Pyrobest polymerase (Takara) to perform a PCR to obtain an amplified DNA fragment. The PCR condition involved 35 cycle in total, each cycle being performed at 95° C. for 1 minutes followed by 68° C. for 2 minutes. The amplified DNA thus obtained fragment was subjected to a 500-fold dilution with TE and used as a template together with the forward primer 5'-gggcgcggccgcccagccaccatggct-tcagacatacctggatctgtgacgttgcc-3' (SEQ ID No.31) and the reverse primer 5'-gggctctagactactcagaaaacggtg-gaaacatgcccaggtcgg-3' (SEQ ID No.32) as well as a Pyrobest polymerase (Takara) to perform a PCR again to obtain an amplified DNA fragment. The PCR condition involved 35 cycle in total, each cycle being performed at 95° C. for 1 minutes followed by 68° C. for 2 minutes. The amplified DNA thus obtained fragment had a kozac sequence (5'-CCAGCCACC-3') immediately before the initiation codon of a DNA encoding Arnt2 and a NotI restriction enzyme site further upstream thereof. Into the downstream of the Stop codon possessed by this amplified DNA fragment, an XbaI restriction enzyme site was further introduced. The resultant amplified DNA fragment was cleaved with the both of the restriction enzymes NotI and XbaI and subjected to a low melting point agarose electrophoresis to purify and recover a DNA fragment. The purified and recovered DNA fragment was employed as an insert fragment.

Subsequently, a pBluescript vector which had been cleaved with NotI and XbaI and then subjected to a BAP treatment was employed as a vector, and this vector (0.1 µg) was ligated with the insert fragment (0.5 µg) described above using a T4 Ligase to prepare a pBlue-hArnt2kozac. The correct construction of this plasmid and the correct nucleotide sequence for the Arnt2-encoding DNA translation part were verified by investigating the nucleotide sequence of the binding part and the nucleotide sequence of the translation part.

(2-4-3) pBlue-hArnt3kozac pBlue-hArnt3kozac which is a plasmid comprising a full length Arnt3-encoding DNA translation region was prepared as described below.

First, from a human Brain mRNA (purchased from Clontech), a single stranded cDNA was prepared using a polydT primer (purchased from Amersham Pharmacia) and a reverse transcriptase (SuperScriptII; purchased from Gibco). The resultant cDNA was employed as a template together with the forward primer 5'-atggacacagacaaagatgaccctcatggaaggtt-3' (SEQ ID No.33) and the reverse primer 5'-tgtttacagcggccatg-gcaagtcactaaagtcaac-3' (SEQ ID No.34) as well as a Pyrobest polymerase (Takara) to perform a PCR to obtain an amplified DNA fragment. The PCR condition involved 35 cycle in total, each cycle being performed at 95° C. for 1 minutes followed by 68° C. for 2 minutes. The amplified DNA thus obtained fragment was subjected to a 500-fold dilution with TE and used as a template together with the forward primer 5'-ggggcggccgccccagccaccatggaca-cagacaaagatgaccctcatggaaggtt-3' (SEQ ID No.35) and the reverse primer 5'-gggtctagatgtttacagcggccatg-gcaagtcactaaagtcaac-3' (SEQ ID No.36) as well as a Pyrobest polymerase (Takara) to perform a PCR again to obtain an amplified DNA fragment. The PCR condition involved 35 cycle in total, each cycle being performed at 95° C. for 1 minutes followed by 68° C. for 2 minutes. The amplified DNA thus obtained fragment had a kozac sequence (5'-CCAGCCACC-3') immediately before the initiation codon of a DNA encoding Arnt3 and a NotI restriction enzyme site further upstream thereof. Into the downstream of the stop codon possessed by this amplified DNA fragment, an XbaI restriction enzyme site was further introduced. The resultant amplified DNA fragment was cleaved with the both of the restriction enzymes NotI and XbaI and subjected to a low melting point agarose electrophoresis to purify and recover a DNA fragment. The purified and recovered DNA fragment was employed as an insert fragment.

Subsequently, a pBluescript vector which had been cleaved with NotI and XbaI and then subjected to a BAP treatment was employed as a vector, and this vector (0.1 µg) was ligated with the insert fragment (0.5 µg) described above using a T4 Ligase to prepare a pBlue-hArnt3kozac. The correct construction of this plasmid and the correct nucleotide sequence for the Arnt3-encoding DNA translation part were verified by investigating the nucleotide sequence of the binding part and the nucleotide sequence of the translation part.

(2-4-4) pGEM-hBmal2kozac pGEM-hBmal2kozac which is a plasmid comprising a full length Bmal2-encoding DNA translation region was prepared as described below.

First, from a human Brain mRNA (purchased from Clontech), a single stranded cDNA was prepared using a polydT primer (purchased from Amersham Pharmacia) and a reverse transcriptase (SuperScriptII; purchased from Gibco). The resultant cDNA was employed as a template together with the forward primer 5'-agctatggggtcttccagctcacacatgacagag-3' (SEQ ID No.37) and the reverse primer 5'-atcaaaggcta-gagggtccactggatgtcactgaa-3' (SEQ ID No.38) as well as a Pyrobest polymerase (Takara) to perform a PCR to obtain an amplified DNA fragment. The PCR condition involved 35 cycle in total, each cycle being performed at 95° C. for 1 minutes followed by 68° C. for 2 minutes. The amplified DNA thus obtained fragment was subjected to a 500-fold dilution with TE and used as a template together with the forward primer 5'-gggcgcggccgcccagccac-catggggtcttccagctcacacatgacagagtttcc-3' (SEQ ID No.39) and the reverse primer 5'-atcaaaggctagagggtccactggatgt-cactgaa-3' (SEQ ID No.40) as well as a LA-Taq polymerase (Takara) to perform a PCR again to obtain an amplified DNA fragment. The PCR condition involved 35 cycle in total, each cycle being performed at 95° C. for 1 minutes followed by 68° C. for 2 minutes. The amplified DNA thus obtained fragment had a kozac sequence (5'-CCAGCCACC-3') immediately before the initiation codon of a DNA encoding Bmal2 and a NotI restriction enzyme site further upstream thereof. The resultant amplified DNA fragment was subjected to a low melting point agarose electrophoresis for the purification and the recovery. The amplified DNA thus purified and recovered was employed as an insert fragment. This insert fragment (0.5 µg) was ligated with a pGEMeasyT (purchased from Promega) vector (0.1 µg) using a T4 Ligase to yield pGEM-hBmal2kozac. The correct construction of this plasmid and the correct nucleotide sequence of the DNA encoding Bmal2 translation part were verified by investigating the nucleotide sequence of the binding part and the nucleotide sequence of the translation part.

(2-4-5) pRC/RSV-hSim2kozac pRC/RSV-hSim2kozac which is a plasmid comprising a full length Sim2-encoding DNA translation region was prepared as described below.

First, from a human Kidney mRNA (purchased from Clontech), a single stranded cDNA was prepared using a polydT primer (purchased from Amersham Pharmacia) and a reverse transcriptase (SuperScriptII: purchased from Gibco). The resultant cDNA was employed as a template together with the forward primer 5'-gtctaatatgcccggagccgaggcgcgatgaagga-3' (SEQ ID No.41) and the reverse primer 5'-tcacctcccgttggtgat-gatgaccgaggcgcccag-3' (SEQ ID No.42) as well as a Pyrobest polymerase (Takara) to perform a PCR to obtain an amplified DNA fragment. The PCR condition involved 35 cycle in total, each cycle being performed at 95° C. for 1 minutes followed by 68° C. for 2 minutes. The amplified DNA thus obtained fragment was subjected to a 500-fold dilution with TE and used as a template together with the forward primer 5'-gggcgcggccgcccagccaccatgaag-gagaagtccaagaatgcggccaagaccag-3' (SEQ ID No.43) and the reverse primer 5'-gggctctagatcacctcccgttggtgat-gatgaccgaggcgccca-3' (SEQ ID No.44) as well as a Pyrobest polymerase (Takara) to perform a PCR again to obtain an amplified DNA fragment. The PCR condition involved 35 cycle in total, each cycle being performed at 95° C. for 1 minutes followed by 68° C. for 2 minutes. The amplified DMA thus obtained fragment had a kozac sequence (5'-CCAGCCACC-3') immediately before the initiation codon of a DNA encoding Sim2 and a NotI restriction enzyme site further upstream thereof. Into the downstream of the Stop codon possessed by this amplified DNA fragment, an XbaI restriction enzyme site was further introduced. The resultant amplified DNA fragment was cleaved with the both of the restriction enzymes NotI and XbaI and subjected to a low melting point agarose electrophoresis to purify and recover a DNA fragment. The purified and recovered DNA fragment was employed as an insert fragment.

Subsequently, a pRC/RSV vector which had been cleaved with NotI and XbaI and then subjected to a BAP treatment was employed as a vector, and this vector (0.1 µg) was ligated with the insert fragment (0.5 µg) described above using a T4 Ligase to prepare a pRC/RSV-hSim2kozac. The correct construction of this plasmid and the correct nucleotide sequence for the Sim2-encoding DNA translation part were verified by investigating the nucleotide sequence of the binding part and the nucleotide sequence of the translation part.

(2-4-6) pBlue-hClockkozac pBlue-hClockkozac which is a plasmid comprising a full length Clock translation region was prepared as described below.

First, from a human Brain mRNA (purchased from Clontech), a single stranded cDNA was prepared using a polydT primer (purchased from Amersham Pharmacia) and a reverse transcriptase (SuperScriptII; purchased from Gibco). The resultant cDNA was employed as a template together with the forward primer 5'-gatccaaggagtacaaaaggagaagtacaaatgtc-3' (SEQ ID No.45) and the reverse primer 5'-tactgcatctcat-gaaactgctggaactttccct-3' (SEQ ID No.46) as well as a Pyrobest polymerase (Takara) to perform a PCR to obtain an amplified DNA fragment. The PCR condition involved 35 cycle in total, each cycle being performed at 95° C. for 1 minutes followed by 68° C. for 3 minutes. The terminal of the amplified DNA fragment thus obtained was phosphorylated using a T4 kinase, and then subjected to a low melting point agarose electrophoresis to purify and recover an amplified DNA fragment (about 2.5 kbp). The amplified DNA fragment thus purified and recovered was employed as an insert fragment. A pBluescript II vector (Stratagene) which had been cleaved with SmaI and then subjected to a BAP treatment was employed as a vector, and this vector (0.1 µg) was ligated with the insert fragment (0.5 µg) described above using a T4 Ligase to prepare a pBlue-hClock. The correct Clock translation sequence of the resultant plasmid were verified by investigating the all nucleotide sequence of the translation sequence part.

Subsequently, 1 µg of this plasmid was employed as a template together with the forward primer 5'-gggcgggatc-cccagccaccatgttgtttaccgtaagctg-3' (SEQ ID No.47) and the reverse primer 5'-ctactgtggttgaaccttgg-31 (SEQ ID No.48) as well as a Pyrobest polymerase (Takara) to perform a PCR again to obtain an amplified DNA fragment. The PCR condition involved 35 cycle in total, each cycle being performed at 95° C. for 1 minutes followed by 68° C. for 3 minutes. The amplified DNA thus obtained has a kozac sequence (5'-CCAGCCACC-3') immediately before the initiation codon of the Clock. The terminal of the amplified DNA fragment thus obtained was phosphorylated using a T4 kinase, and then subjected to a low melting point agarose electrophoresis for purification and recovery. The amplified DNA fragment thus purified and recovered was employed as an insert fragment described above. Then, a pBluescript II vector which had been cleaved with SmaI and then subjected to a BAP treatment was employed as a vector, and this vector (0.1 µg) was ligated with the insert fragment (0.5 µg) using a T4 Ligase to prepare a pBlue-hClock kozac. The correct nucleotide sequence of the translation part of the DNA encoding the Clock in the plasmid thus prepared was verified by investigating the total nucleotide sequence of this translation part.

(2-5) Preparation of pRC/RSV-MC-mNXF(bHLH-PAS), pRC/RSV-MC-Arnt1 (bHLH-PAS), pRC/RSV-MC-Arnt2 (bHLH-PAS), pRC/RSV-MB-Arnt3(bHLH-PAS), pRC/RSV-MA-Bmal2(bHLH-PAS) (Construction of Chimera Protein-Expressing Plasmid Required for Two-Hybrid Assay (Part 1))

(2-5-1) pRC/RSV-MC-mNXF (bHLH-PAS)

A plasmid pRC/RSV-MC-mNXF(bHLH-PAS) which expresses a chimera protein (hereinafter sometimes designated as a Gal4-mNXF) resulting from the binding between the DNA-binding region of GAL4 as a transcription regulatory factor and the bHLH-PAS region part of a present transcription regulatory factor (mNXF) was produced as described below. A pGEM-mNXF prepared in EXAMPLE 1 was cleaved with SacI and ApaI and imparted with a blunt end using a T4 polymerase, and then subjected to a low melting point agarose electrophoresis (Agarose L; Nippon Gene) to purify and recover a DNA fragment (about 1.8 kbp: containing the bHLH-PAS region part of the present transcription regulatory factor(mNXF)). The DNA fragment thus purified and recovered was used as an insert fragment. A pRC/RSV-MC which had been cleaved with pmaCI and then subjected to a BAP treatment was employed as a vector, and this vector (0.1 µg) was ligated with the insert fragment (0.5 µg) described above using a T4 Ligase to prepare a pRC/RSV-MC-mNXF(bHLH-PAS). The correct construction of this plasmid and the agreement of the frame of the mNXF-encoding DNA translation part with the frame of the Gal4-DBD-encoding DNA were verified by investigating the nucleotide sequence of the binding part and the nucleotide sequence of the translation part.

(2-5-2) pRC/RSV-MC-Arnt1(bHLH-PAS)

A plasmid pRC/RSV-MC-Arnt1(bHLH-PAS) which expresses a chimera protein (hereinafter sometimes designated as a Gal4-Arnt1) resulting from the binding between the DNA-binding region of GAL4 as a transcription regulatory factor and the bHLH-PAS region part of a present ARNT transcription coupling factor Arnt1 was produced as described below.

A pBlue-hArnt1kozac prepared in the section (2-4-1) described above was cleaved with NotI and NaeI and imparted with a blunt end using a T4 polymerase, and then subjected to a low melting point agarose electrophoresis (Agarose L; Nippon Gene) to purify and recover a DNA fragment (about 1.8 kbp: containing the bHLH-PAS region part of Arnt1). The DNA fragment thus purified and recovered was used as an insert fragment. A pRC/RSV-MC which had been cleaved with pmaCI and then subjected to a BAP treatment was employed as a vector, and this vector (0.1 µg) was ligated with the insert fragment (0.5 µg) described above using a T4 Ligase to prepare a pRC/RSV-MC-Arnt1(bHLH-PAS). The correct construction of this plasmid and the agreement of the frame of the Arnt1-encoding DNA translation part with the frame of the Gal4-DBD-encoding DNA were verified by investigating the nucleotide sequence of the binding part and the nucleotide sequence of the translation part.

(2-5-3) pRC/RSV-MC-Arnt2(bHLH-PAS)

A plasmid pRC/RSV-MC-Arnt2(bHLH-PAS) which expresses a chimera protein (hereinafter sometimes designated as a Gal4-Arnt2) resulting from the binding between the DNA-binding region of GAL4 as a transcription regulatory factor and the bHLH-PAS region part of a present ARNT transcription coupling factor Arnt2 was produced as described below.

A pBlue-hArnt2kozac prepared in the section (2-4-2) described above was cleaved with NotI and BglII and imparted with a blunt end using a T4 polymerase, and then subjected to a low melting point agarose electrophoresis (Agarose L; Nippon Gene) to purify and recover a DNA fragment (about 1.5 kbp: containing the bHLH-PAS region part of Arnt2). The DNA fragment thus purified and recovered was used as an insert fragment. A pRC/RSV-MC which had been cleaved with pmaCI and then subjected to a BAP treatment was employed as a vector, and this vector (0.1 µg) was ligated with the insert fragment (0.5 µg) described above using a T4 Ligase to prepare a pRC/RSV-MC-Arnt2(bHLH-PAS). The correct construction of this plasmid and the agreement of the frame of the Arnt2-encoding DNA translation part with the frame of the Gal4-DBD-encoding DNA were verified by investigating the nucleotide sequence of the binding part and the nucleotide sequence of the translation part.

(2-5-4) pRC/RSV-MB-Arnt3(bHLH-PAS)

A plasmid pRC/RSV-MC-Arnt3(bHLH-PAS) which expresses a chimera protein (hereinafter sometimes designated as a Gal4-Arnt3) resulting from the binding between the DNA-binding region of GAL4 as a transcription regulatory factor and the bHLH-PAS region part of a present ARNT transcription coupling factor Arnt3 was produced as described below.

A pBlue-hArnt3kozac prepared in the section (2-4-3) described above was cleaved with NotI and SphI and imparted with a blunt end using a T4 polymerase, and then subjected to a low melting point agarose electrophoresis (Agarose L; Nippon Gene) to purify and recover a DNA fragment (about 1.3 kbp: containing the bHLH-PAS region part of Arnt3). The DNA fragment thus purified and recovered was used as an insert fragment. A pRC/RSV-MB which had been cleaved with pmaCI and then subjected to a BAP treatment was employed as a vector, and this vector (0.1 µg) was ligated with the insert fragment (0.5 µg) described above using a T4 Ligase to prepare a pRC/RSV-MB-Arnt3(bHLH-PAS). The correct construction of this plasmid and the agreement of the frame of the Arnt3-encoding DNA translation part with the frame of the Gal4-DBD-encoding DNA were verified by investigating the nucleotide sequence of the binding part and the nucleotide sequence of the translation part.

(2-5-5) pRC/RSV-MA-Bmal2(bHLH-PAS)

A plasmid pRC/RSV-MA-Bmal2(bHLH-PAS) which expresses a chimera protein (hereinafter sometimes designated as a Gal4-Bmal2) resulting from the binding between the DNA-binding region of GAL4 as a transcription regulatory factor and the bHLH-PAS region part of a transcription coupling factor Bmal2 was produced as described below.

A pGEM-hBmal2kozac prepared in the section (2-4-4) described above was cleaved with NotI and AccI and imparted with a blunt end using a T4 polymerase, and then subjected to a low melting point agarose electrophoresis (Agarose L; Nippon Gene) to purify and recover a DNA fragment (about 1.25 kbp: containing the bHLH-PAS region part of Bmal2). The DNA fragment thus purified and recovered was used as an insert fragment. A pRC/RSV-MA which had been cleaved with pmaCI and then subjected to a BAP treatment was employed as a vector, and this vector (0.1 µg) was ligated with the insert fragment (0.5 µg) described above using a T4 Ligase to prepare a pRC/RSV-MA-Bmal2 (bHLH-PAS). The correct construction of this plasmid and the agreement of the frame of the Bmal2-encoding DNA translation part with the frame of the Gal4-DBD-encoding DNA were verified by investigating the nucleotide sequence of the binding part and the nucleotide sequence of the translation part.

(2-6) Preparation of pVP16-Arnt1 (bHLH-PAS), pVP16-Arnt2 (bHLH-PAS), pVP16-Arnt3 (bHLH-PAS), pVP16-BMAL2(bHLH-PAS), pVP16-Sim2 (bHLH-PAS), pVP16-Clock (bHLH-PAS), pVP16-NXF (bHLH-PAS) and pVP16-CP (Construction of Chimera Protein-Expressing Plasmid Required for Two-Hybrid Assay (Part 2))

(2-6-1) pVP16-Arnt1 (bHLH-PAS)

A plasmid pVP16-Arnt1 (bHLH-PAS) which expresses a chimera protein (hereinafter sometimes designated as a VP16-Arnt1) resulting from the binding between the Vp16 transcription activating region and the bHLH-PAS region part of a transcription coupling factor Arnt1 was produced as described below.

A pBlue-hArnt1kozac prepared in the section (2-4-1) described above was cleaved with NotI and NaeI and imparted with a blunt end using a T4 polymerase, and then subjected to a low melting point agarose electrophoresis (Agarose L; Nippon Gene) to purify and recover a DNA fragment (about 1.8 kbp: containing the bHLH-PAS region part of Arnt1). The DNA fragment thus purified and recovered was used as an insert fragment. A pVP16 vector (purchased from Clontech) which had been cleaved with BamHI and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-Arnt1 (bHLH-PAS). The correct construction of this plasmid and the agreement of the frame of the Arnt1-encoding DNA translation part with the frame of the VP16 transcription activating region-encoding DNA were verified by investigating the nucleotide sequence of the binding part and the nucleotide sequence of the translation part.

(2-6-2) pVP16-Arnt2 (bHLH-PAS)

A plasmid pVP16-Arnt2 (bHLH-PAS) which expresses a chimera protein (hereinafter sometimes designated as a VP16-Arnt2) resulting from the binding between the Vp16 transcription activating region and the bHLH-PAS region part of a present ARNT transcription coupling factor Arnt2 was produced as described below.

A pBlue-hArnt2kozac prepared in the section (2-4-2) described above was cleaved with NotI and BglII and imparted with a blunt end using a T4 polymerase, and then subjected to a low melting point agarose electrophoresis (Agarose L; Nippon Gene) to purify and recover a DNA fragment (about 1.5 kbp: containing the bHLH-PAS region part of Arnt2). The DNA fragment thus purified and recovered was used as an insert fragment. A pVP16 vector (purchased from Clontech) which had been cleaved with BamHI and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-Arnt2 (bHLH-PAS). The correct construction of this plasmid and the agreement of the frame of the Arnt2-encoding DNA translation part with the frame of the VP16 transcription activating region-encoding DNA were verified by investigating the nucleotide sequence of the binding part and the nucleotide sequence of the translation part.

(2-6-3) pVP16-Arnt3 (bHLH-PAS)

A plasmid pVP16-Arnt3 which expresses a chimera protein (hereinafter sometimes designated as a VP16-Arnt3) resulting from the binding between the Vp16 transcription activating region and the full length present ARNT transcription coupling factor Arnt3 containing the bHLH-PAS region part was produced as described below.

A pBlue-hArnt3kozac prepared in the section (2-4-3) described above was cleaved with NotI and XbaI and imparted with a blunt end using a T4 polymerase, and then subjected to a low melting point agarose electrophoresis (Agarose L; Nippon Gene) to purify and recover a DNA fragment (about 1.8 kbp: containing the full length Arnt3). The DNA fragment thus purified and recovered was used as an insert fragment. A pVP16 vector (purchased from Clontech) which had been cleaved with EcoRI and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-Arnt3. The correct construction of this plasmid and the agreement of the frame of the Arnt3-encoding DNA translation part with the frame of the VP16 transcription activating region-encoding DNA were verified by investigating the nucleotide sequence of the binding part and the nucleotide sequence of the translation part.

(2-6-4) pVP16-BMAL2 (bHLH-PAS)

A plasmid pVP16-Bmal2 which expresses a chimera protein (hereinafter sometimes designated as a VP16-Bmal2) resulting from the binding between the Vp16 transcription activating region and the full length transcription coupling factor Bmal2 containing the bHLH-PAS region part was produced as described below.

A pGEM-hBmal2kozac prepared in the section (2-4-4) described above was cleaved with NotI and imparted with a blunt end using a T4 polymerase, and then subjected to a low melting point agarose electrophoresis (Agarose L; Nippon Gene) to purify and recover a DNA fragment (about 1.7 kbp: containing the full length Bmal2). The DNA fragment thus purified and recovered was used as an insert fragment. A pVP16 vector (purchased from Clontech) which had been cleaved with HindIII and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-Bmal2. The correct construction of this plasmid and the agreement of the frame of the Bmal2-encoding DNA translation part with the frame of the VP16 transcription activating region-encoding DNA were verified by investigating the nucleotide sequence of the binding part and the nucleotide sequence of the translation part.

(2-6-5) pVP16-Sim2 (bHLH-PAS)

A plasmid pVP16-Sim2 (bHLH-PAS) which expresses a chimera protein (hereinafter sometimes designated as a VP16-Sim2) resulting from the binding between the Vp16 transcription activating region and the bHLH-PAS region part of Sim2 was produced as described below. A pRC/RSV-hSim2kozac prepared in the section (2-4-5) described above was cleaved with NotI and BamHI and imparted with a blunt end using a T4 polymerase, and then subjected to a low melting point agarose electrophoresis (Agarose L; Nippon Gene) to purify and recover a DNA fragment (about 1.5 kbp: containing the bHLH-PAS region part of Sim2). The DNA fragment thus purified and recovered was used as an insert fragment. A pVP16 vector (purchased from Clontech) which had been cleaved with BamHI and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-Sim2 (bHLH-PAS). The correct construction of this plasmid and the agreement of the frame of the Sim2-encoding DNA translation part with the frame of the VP16 transcription activating region-encoding DNA were verified by investigating the nucleotide sequence of the binding part and the nucleotide sequence of the translation part.

(2-6-6) pVP16-Clock (bHLH-PAS)

A plasmid pVP16-Clock (bHLH-PAS) which expresses a chimera protein (hereinafter sometimes designated as a VP16-Clock) resulting from the binding between the Vp16 transcription activating region and the bHLH-PAS region part of Clock was produced as described below.

A pBlue-hClock kozac prepared in the section (2-4-6) described above was cleaved with HicII and NcoI and imparted with a blunt end using a T4 polymerase, and then subjected to a low melting point agarose electrophoresis (Agarose L; Nippon Gene) to purify and recover a DNA fragment (about 1.6 kbp: containing the bHLH-PAS region part of Clock). The DNA fragment thus purified and recovered was used as an insert fragment. A pVP16 vector (purchased from Clontech) which had been cleaved with BamHI and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-Clock (bHLH-PAS). The correct construction of this plasmid and the agreement of the frame of the Clock-encoding DNA translation part with the frame of the VP16 transcription activating region-encoding DNA were verified by investigating the nucleotide sequence of the binding part and the nucleotide sequence of the translation part.

(2-6-7) pVP16-NXF (bHLH-PAS)

A plasmid pVP16-NXF (bHLH-PAS) which expresses a chimera protein (hereinafter sometimes designated as a VP16-NXF) resulting from the binding between the Vp16 transcription activating region and the bHLH-PAS region part of a present transcription activating factor (mNXF) was produced as described below.

A pGEM-mNXF prepared in EXAMPLE 1 was cleaved with SacI and ApaI and imparted with a blunt end using a T4 polymerase, and then subjected to a low melting point agarose electrophoresis (Agarose L; Nippon Gene) to purify and recover a DNA fragment (about 1.8 kbp: containing the bHLH-PAS region part of a present transcription activating factor (mNXF)). The DNA fragment thus purified and recovered was used as an insert fragment. A pVP16 vector (purchased from Clontech) which had been cleaved with BamHI and then subjected to a BAP treatment and then further imparted with a blunt end using a T4 polymerase was employed as a vector, and this vector (0.1 µg) was ligated with the insert fragment (0.5 µg) described above using a T4 Ligase to prepare a pVP16-NXF (bHLH-PAS). The correct construction of this plasmid and the agreement of the frame of the present transcription activating factor (mNXF) DNA translation part with the frame of the VP16 transcription activating region-encoding DNA were verified by investigating the nucleotide sequence of the binding part and the nucleotide sequence of the translation part.

(2-6-8) pVP16-CP

A plasmid pVP16-CP which expresses a chimera protein of a virus core protein with V16 was purchased from Clontech. Since this protein has no relationship with the bHLH-PAS family, it does not bind to a transcription regulatory factor of the bHLH-PAS family. Accordingly, this plasmid was employed as a negative control plasmid in the test described in the section (2-6) shown below.

(2-7) Two-Hybrid Assay for Verifying Formation of Complex of Present ARNT Transcription Coupling Factor with Present Transcription Regulatory Factor About $5 \times 10^6$ HeLa cells were cultured in a 10% FBS-supplemented DMEM medium (NISSUI SEIYAKU) at 37° C. in the presence of 5% $CO_2$ in a petri dish (Falcon) whose diameter was about 10 cm. On the next day, the cultured cells were dispersed by a trypsin treatment, washed twice with a FBS-free DMEM medium, and then dispersed again in a FBS-free DMEM medium at the cell density of $5 \times 10^6$. 0.4 ml of this cell dispersion was combined with the three plasmid, namely, the reporter gene plasmid prepared in the Section (2-1) described above (pGL-TATA-Galx4) (for example 3 µg), the plasmid prepared in the Section (2-5) described above which expresses a chimera protein (for example 3 µg) and the plasmid prepared in the Section (2-6) described above which expresses a chimera protein (for example 3 µg), and the mixture was transferred into an electroporation cuvette, where a transfection was conducted by an electroporation method employing a Gene pulser (BIORAD) under the conditions involving 220V and 950 µF. After the transfection, the culture medium was replaced with a 10% FBS-supplemented DMEM, and then further cultured in a 6-well plate for about 24 hours. Then, the culture medium was removed from the wells, and the cells depositing on the plate wall were washed twice with PBS(-), and then 200 µl per well of a 5-fold diluted PGC 50 (TOYO INK) was added and allowed to stand at room temperature for 30 minutes. 20 µl Aliquots of this cell suspension were dispensed into a opaque plate (Corning International K.K), and this plate was mounted on a luminometer LB96P (Berthold Japan, Co. Ltd.) fitted with an enzyme substrate automatic injector, and after dispensing 50 µl of the substrate solution PGL100 (TOYO INK) automatically the luciferase activity of each well was determined.

As a result, it was revealed as evident from FIG. 1 that in the system employing Gal4-NXF each of VP16-Arnt1, VP16-Arnt2 and VP16-Arnt3 exhibited a binding activity (interaction) with the bHLH-PAS region part of the present transcription regulatory factor (NXF). On the other hand, none of Bmal2, Sim2 and Clock exhibited a binding activity (interaction) with the bHLH-PAS region part of the present transcription regulatory factor (NXF).

It was also revealed that no homodimer was formed between the present transcription regulatory factors (NXFs).

Figure 2:
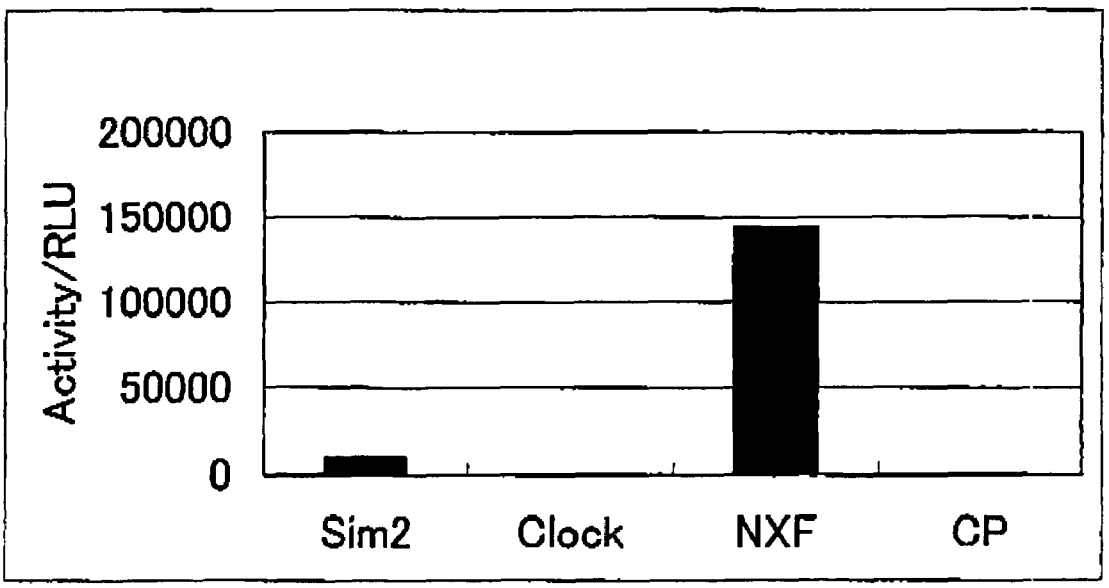
FIG. 2 shows the results of a two-hybrid assay (system employing Gal4-Arnt1+VP16-X) for verifying the formation of the complex of an ARNT 1 as a present ARNT family transcription coupling factor and a present transcription regulatory factor. The abscissa represents a transcription regulatory factor employed in each test system. The left end is of a Sim2, which corresponds to the test system for a positive control. The second from the left end was of a Clock, which corresponds to the test system for a comparison. The second from the right end is of a present transcription regulatory factor (NXF). The right end is of a CP, which corresponds to the test system for a negative control. The ordinate represents a luciferase activity level, which is an index value representing an activity on the transcription of a reporter gene.
Figure 3:
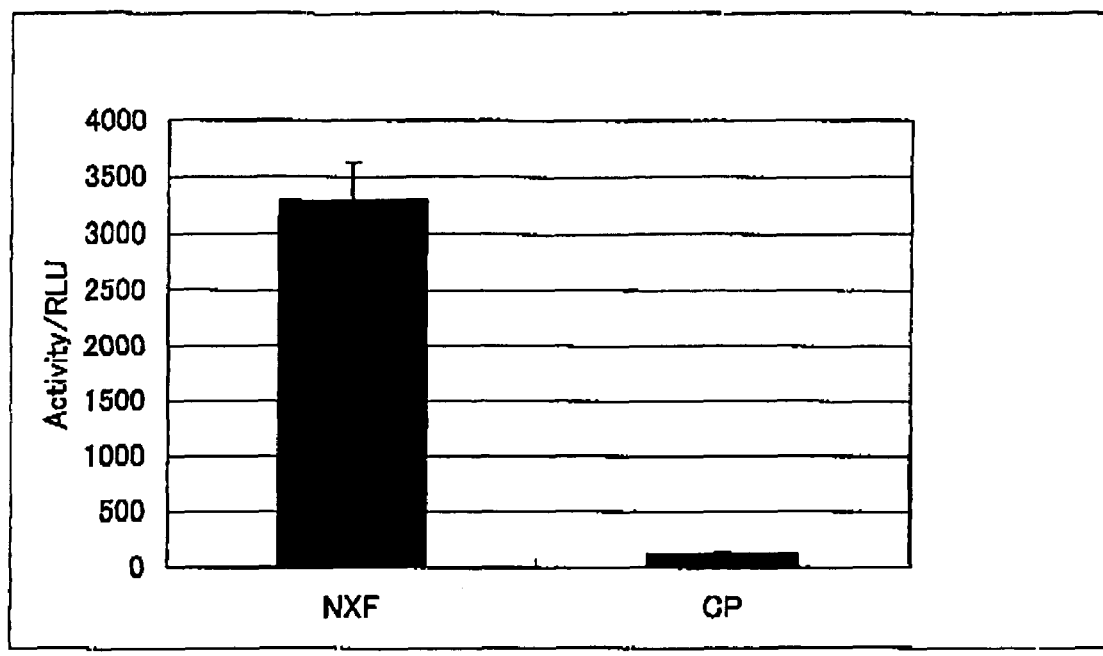
FIG. 3 shows the results of a two-hybrid assay (system employing Gal4-Arnt2+VP16-X) for verifying the formation of the complex of an ARNT 2 as a present ARNT family transcription coupling factor and a present transcription regulatory factor. The abscissa represents a transcription regulatory factor employed in each test system. The left end is of a present transcription regulatory factor (NXF). The right end is of a CP, which corresponds to the test system for a negative control. The ordinate represents a luciferase activity level, which is an index value representing an activity on the transcription of a reporter gene.
Figure 4:
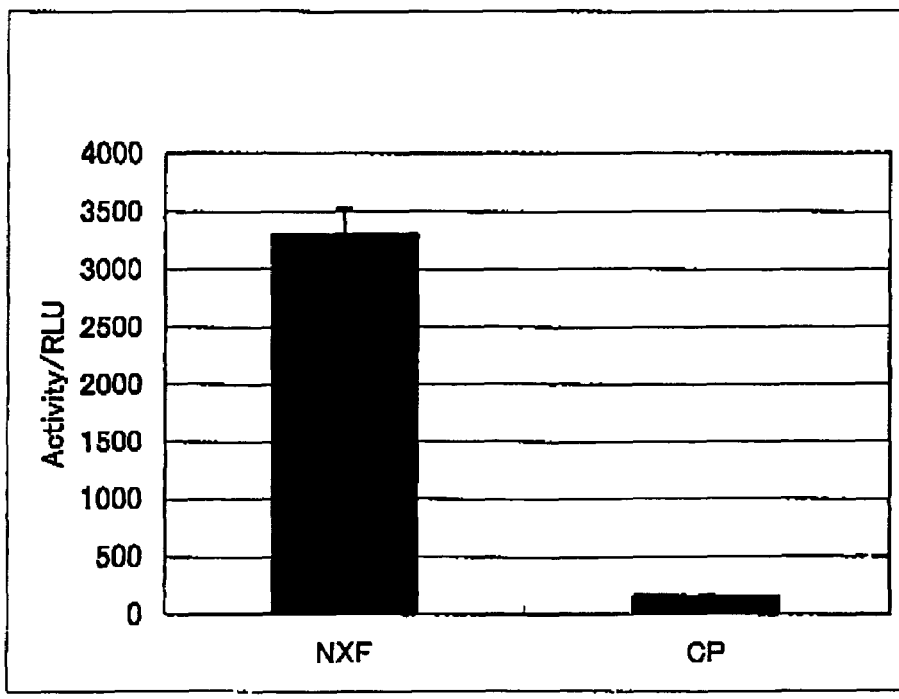
FIG. 4 shows the results of a two-hybrid assay (system employing Gal4-Arnt3+VP16-X) for verifying the formation of the complex of an ARNT 3 as a present ARNT family transcription coupling factor and a present transcription regulatory factor. The abscissa represents a transcription regulatory factor employed in each test system. The left end is of a present transcription regulatory factor (NXF). The right end is of a CP, which corresponds to the test system for a negative control. The ordinate represents a luciferase activity level, which is an index value representing an activity on the transcription of a reporter gene.

In addition, it was revealed as evident from FIGS. 2, 3 and 4 that in the system employing Gal4-Arnt1 (FIG. 2), Gal4-Arnt2 (FIG. 3) and Gal4-Arnt3 (FIG. 4) the inventive transcription regulatory factor (NXF) exhibited a binding activity (interaction) with the bHLH-PAS region part of any of Arnt1, Arnt2 and Arnt3.

Figure 5:
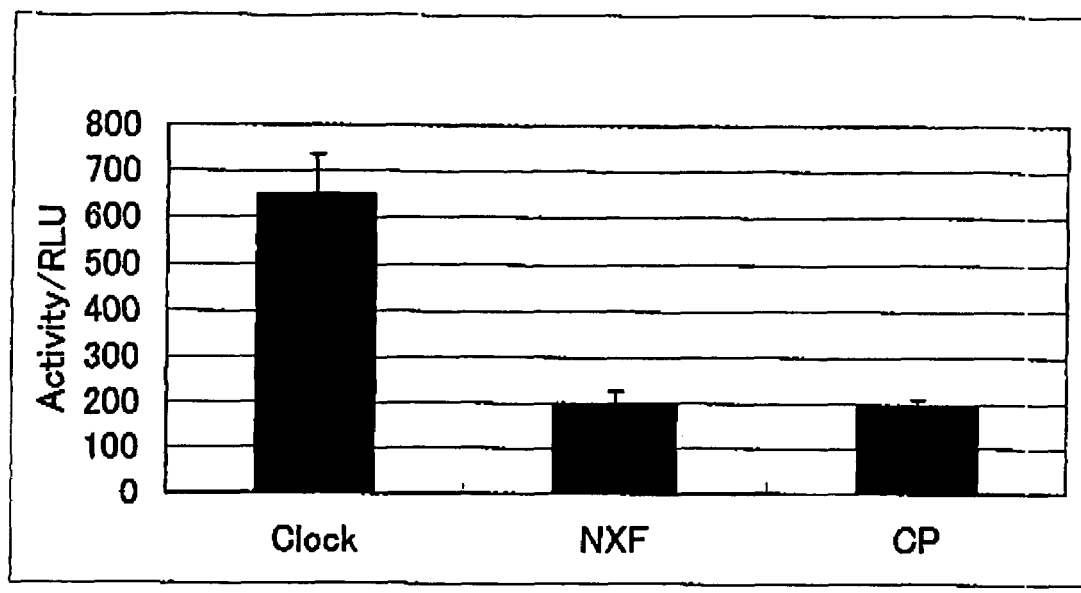
FIG. 5 shows the results of a two-hybrid assay (system employing Gal4-Bmal2+VP16-X) for verifying the formation of the complex of a Bmal2 as a non-present ARNT family transcription coupling factor and a present transcription regulatory factor. The abscissa represents a transcription regulatory factor employed in each test system. The left end is of a Clock, which corresponds to the test system for a positive control. The midst is of a present transcription regulatory factor (NXF). The right end is of a CP, which corresponds to the test system for a negative control. The ordinate represents a luciferase activity level, which is an index value representing an activity on the transcription of a reporter gene.

It was also revealed here again that in the system employing Gal4-Bmal2 (FIG. 5) the present transcription regulatory factor (NXF) exhibited no binding activity (interaction) with Bmal2.

(2-8) Gel Shift Assay for Verifying DNA Binding Ability Possessed by Inventive Transcription Activating Complex (2-8-1) Preparation of pVL1392-hArnt2kozac (Construction of Transfer Vector for Preparing Recombinant Virus Expressing Full Length Present ARNT Transcription Coupling Factor)

A transfer vector pVL1392-hArnt2kozac for producing a recombinant virus (Baculovirus) expressing a full length Arnt2 was prepared as described below.

First, the pBlue-hArnt2kozac prepared in the section (1-4) described above was cleaved simultaneously with NotI and XbaI, and then subjected to a low melting point agarose electrophoresis (Agarose L; Nippon Gene) to recover a DNA fragment (about 2.2 kbp: containing the full length Arnt 2 translation region). The recovered DNA fragment was employed as an insert fragment.

Subsequently, a pVL1392 vector (purchased from Pharmingen) which had been cleaved with NotI and XbaI and then subjected to a BAP treatment was employed as a vector, and this vector (0.1 µg) was ligated with the insert fragment (0.5 µg) described above using a T4 Ligase to prepare a pVL1392-hArnt2kozac which was a transfer vector for preparing a recombinant virus expressing the full length Arnt2. The correct construction of the translation region of the DNA encoding Arnt 2 downstream of a polyhedrin promoter was verified by investigating the nucleotide sequence of the binding part.

(2-8-2) Preparation of pVL1392-NXF (Construction of Transfer Vector for Preparing Recombinant Virus Expressing Full Length Present Transcription Regulatory Factor)

Then, a transfer vector pVL1392-rNXF for producing a recombinant virus (Baculovirus) expressing a full length present transcription regulatory factor (rNXF) was prepared as described below.

First, the pGEM-rNXF was cleaved simultaneously with ScaI and SacI and also with NotI, and then imparted with a blunt end using a T4 polymerase. The blunt-ended DNA fragment was subjected to a low melting point agarose electrophoresis (Agarose L; Nippon Gene) to recover a DNA fragment (about 2.5 kbp: containing the full length Arnt translation region of the present transcription regulatory factor (NXF)). The recovered DNA fragment was employed as an insert fragment.

Subsequently, a pVL1393 vector (purchased from Pharmingen) which had been cleaved with SmaI and then subjected to a BAP treatment was employed as a vector, and this vector (0.1 µg) was ligated with the insert fragment (0.5 µg) described above using a T4 Ligase to prepare a pVL1392-rNXF which was a transfer vector for preparing a recombinant virus expressing the present transcription regulatory factor (rNXF).

The correct construction of the translation region of the translation region of the present transcription regulatory factor (rNXF) downstream of a polyhedrin promoter was verified by investigating the nucleotide sequence of the binding part.

The pGEN-rNXF employed as described above was prepared by the method similar to that employed for preparing pGEM-mNXF described in EXAMPLE 1 except for using as a template a rat Brain cDNA library instead of the mouse Brain cDNA library.

(2-8-3) Preparation of Recombinant Virus Particle Comprising Present ARNT Transcription Coupling Factor Arnt2 or Present Transcription Regulatory Factor (rNXF) Introduced Therein An insect cell line Sf21 (purchased from Invitrogen) was cultured in a 10% FCS (fetal calf serum), 0.33% yeast hydrolysate, 0.33% lactoalbumin hydrolysate-supplemented Grace medium (purchased from Gibco) in an ordinary atmospheric environment at 27° C. The cultured cell was introduced with a transfer vector for preparing a recombinant virus and a Baculovirus genome DNA as described below.

First, $10^6$ cells were inoculated into the wells of a 6-well plate and allowed to stand for 2 hours. After ensuring the adhesion of the cells, the culture medium in each well was replaced with 0.8 ml of a serum-free Grace medium. To the cells thus prepared, a mixture prepared by mixing 0.25 µg of linear Baculovirus genome DNA (Baculo Gold DNA; purchased from Pharmingen) and 2 µg of the transfer vector for preparing the recombinant virus with 200 µl of the serum-free medium, adding 6 µl of a Cell Fectin reagent (purchased from Gibco) and allowing to stand at room temperature for 15 minute was added. After 5 hours, the culture medium in each well was replaced with an ordinary serum-containing Grace medium and incubated continuously for 72 hours. As a result of a homologous recombination of the transfer vector for preparing the recombinant virus and the Baculovirus genome DNA, a recombinant virus particle in which the present ARNT transcription coupling factor Arnt2-encoding DNA or the present transcription regulatory factor (rNXF) was integrated into the downstream of a promoter possessed by a polyhedrin protein gene derived from the Baculovirus was obtained. As a control, a commercially available wild baculovirus (non-recombinant virus, purchased from Pharmingen) was employed.

(2-8-4) Preparation of Whole Cell Extract Containing Present ARNT Transcription Coupling Factor Arnt2 or Present Transcription Regulatory Factor (NXF)

A whole cell extract containing a present ARNT transcription coupling factor Arnt2 or a present transcription regulatory factor (NXF) was prepared as described below.

First, $10^6$ cells of insect cell line SF21 in a T50 flask were infected with the recombinant virus particle prepared in the section (2-8-3) described above. 72 hours after the infection, the cells were centrifuged at 1000 G for 2 minutes to recover the cell pellets. The recovered cell pellets were homogenized by a pipetting operation in a buffer whose volume was 4 times that of the cells and which contained 20 mM HEPS (pH7.9), 300 mM NaCl and 20% Glycerol, and allowed to stand on ice for 30 minutes. Subsequently, it was centrifuged at 10000 G for 1 hour to recover the supernatant. This supernatant was employed in the following tests as a whole cell extract containing a present RNT transcription coupling factor Arnt2 or a present transcription regulatory factor (NXF).

(2-8-5) Gel Shift Assay

A gel shift assay was conducted as described below.

First, a CME double-stranded oligonucleotide was prepared by hybridizing two oligonucleotides (SEQ ID No.49: 5'-ctagaaatttgtacgtgccacaga-3', SEQ ID No.50:5'-tctgtg-gcacgtacaaatttctag-3'). On the other hand, an E-Box double-stranded oligonucleotide (a DNA which has a nucleotide sequence containing a single nucleotide substitution in a CME core sequence and to which Sim2 and Arnt2 are no longer bound) was prepared by hybridizing two oligonucleotides (SEQ ID No.51: 5'-caagtccacgtgcaggga-3', SEQ ID No.52: 5'-tccctgcacgtggacttg-3').

2 µg of the CME double-stranded oligonucleotide thus prepared was reacted in the presence of 10U of a T4 kinase and 3.7 MBq of [$\gamma$-$^{32}$P]-ATP (AA0018; Amarsham Pharmacia) at 37° C. for 1 hour to radiolabel its 5' terminal. This was centrifuged at 1000 G for 2 minutes using a spin column (ProbeQuant G50 micro columns; Amersham Pharmacia) to obtain as a passing-through fraction a radiolabeled CME double-stranded oligonucleotide which was free from any excessive radioactive substrate. The radiolabeled CME double-stranded oligonucleotide thus obtained was employed at about $10^4$ DPM/group as a hot probe DNA in the gel shift assay described below. The binding with the hot probe DNA in the gel shift assay was conducted by incubating a reaction solution containing 20 mM HEPES (pH7.9), 100 mM NaCl, 1 mM DTT, 5% Glycerol, 0.1 µg/µl Poly [dI-dC] and 1 µg of the whole cell extract prepared in the section (2-8-4) described above at 25° C. for 30 minutes. When a Cold probe DNA was added as a competitor to the binding reaction system, it was allowed to coexist in the binding reaction system in an amount which was 100 times the amount of the hot probe DNA. The binding reaction product formed as a result of the binding reaction described above was subjected to a 5% (acrylamide:bis=39:1) polyacrylamide gel electrophoresis using 0.5×TBE buffer. After the electrophoresis, the gel was brought into a close contact with a 3MMChr filter paper, which was dried and then used to expose an IP plate (FUJI, FILM) for about 3 hours. The radio-exposed IP plate was subjected to an imaging analyzer (FUJI FILM) to read the radio-exposed part, whereby obtaining an gal image.

Figure 6:
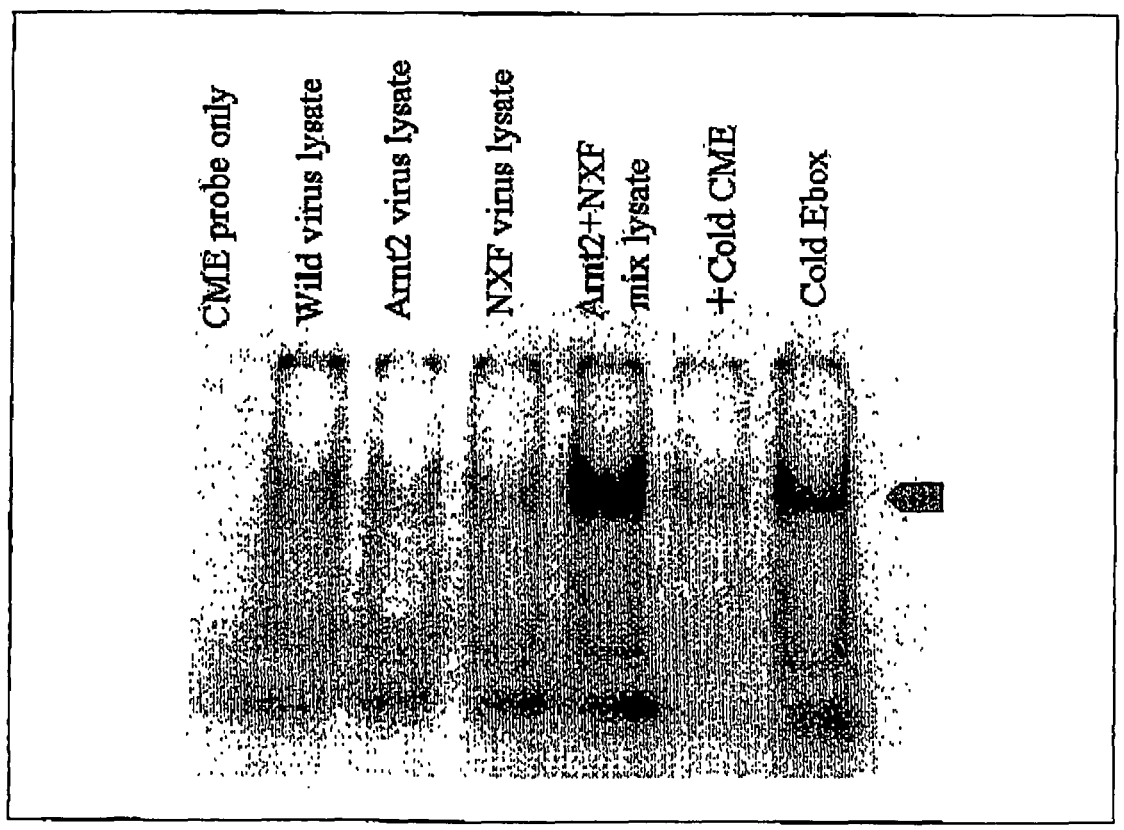
FIG. 6 shows the results of a gel sift assay for verifying the DNA binding ability possessed by an inventive transcription activating complex. Lane 1 employs only a probe as a sample, Lane 2 employs as a sample a total cell extract prepared from a cell infected with a wild Baculovirus (non-recombinant virus), Lane 3 employs as a sample a total cell extract containing an Arnt2 which is a present ARNT family transcription coupling factor, Lane 4 employs as a sample a total cell extract containing a present transcription regulatory factor (NXF), Lane 5 employs as a sample a total cell extract containing an Arnt2 which is a present ARNT family transcription coupling factor together with a present transcription regulatory factor (NXF) (i.e., corresponding to an inventive transcription activating complex), Lane 6 employs as a sample a total cell extract containing an inventive transcription activating complex (i.e., Arnt2 and NXF) when allowing a large excess of a non-radiolabeled CME double-stranded oligonucleotide as a Cold probe DNA to coexist in the binding reaction system and Lane 7 employs as a sample a total cell extract containing an inventive transcription activating complex (i.e., Arnt2 and NXF) when allowing a large excess of a non-radiolabeled E-box double-stranded oligonucleotide as a Cold probe DNA to coexist in the binding reaction system. Each of Lanes 5 and 7 exhibits a band indicating a specific binding (a band indicating the binding with a hot probe DNA).

As a result, FIG. 6 clearly indicated that the band showing the binding with the hot probe DNA (i.e., radiolabeled CME double-stranded oligonucleotide) was observed only when the present transcription regulatory factor (NXF) and the Arnt transcription coupling factor Arnt2 were coexisting. On the other hand, the band disappeared when allowing a large excess of the non-radiolabeled CME double-stranded oligonucleotide as a cold probe DNA to coexist in the binding reaction system, but did not disappeared even when allowing a large excess of the non-radiolabeled E-box double-stranded oligonucleotide as a cold probe DNA to coexist in the binding reaction system, revealing that the band was not bound to the E-box sequence but was bound specifically only to the CME sequence.

As described above, the inventive transcription activating complex was proven to be bound specifically only to the CME sequence (i.e., a DNA region to which the transcription inhibiting complex of the Arnt transcription coupling factor with the transcription regulatory factor Sim2 can be bound).

(2-9) Luciferase Assay Using CME Sequence Responsive Reporter for Verifying Transcription Promoting Ability Possessed by Inventive Transcription Activating Complex (2-9-1) Preparation of pRC/RSV-hArnt2kozac A plasmid for expressing a full length Arnt2 in a mammalian cell was prepared as described below.

First a pBlue-hArnt2kozac was cleaved simultaneously with NotI and XbaI, subjected to a low melting point agarose electrophoresis (agarose L; Nippon Gene) to recover a DNA fragment (about 2.2 kbp) containing a full length translation region of a DNA encoding Arnt2. The recovered DNA fragment was employed as an insert fragment.

Then, a pRC/RVS (purchased from Invitrogen) which had been cleaved with NotI and XbaI and then subjected to a BAP treatment was employed as a vector. This vector (0.1 µg) was ligated with the insert fragment (0.5 µg) described above using a T4 Ligase to prepare a pRC/RSV-hArnt2kozac which was a plasmid for expressing the full length Arnt2 in a mammalian cell (i.e., full length Arnt 2 mammalian cell expression plasmid).

(2-9-2) Preparation of pRC/RSV-mNXFsense (and pRC/RSV-mNXFantisense)

Then, a plasmid for expressing a full length present transcription regulatory factor (mNXF) in a mammalian cell was prepared as described below.

First, the direction of the insertion fragment in relation with the multiple cloning site of the pGEM-mNXF was in such a construction that the Sp6 promoter of a commercial pGEM vector was positioned upstream of the initiation codon. Then 1 µg of this pGEM-mNXF was employed as a template together with two oligonucleotide primers (forward primer 5'-gggcgctgcagcccagccaccatgtaccgatccaccaaggg-3' (SEQ ID No.53), reverse primer 5'-aatctcggcgttgatctggt-3' (SEQ ID No.54) to effect a PCR using a KODplus polymerase (TOYOBO), whereby a partial fragment of the present transcription regulatory factor (mNXF) DNA into which a Kozac sequence (5'-CCAGCCACC-3') immediately before the initiation codon of the present transcription regulatory factor (mNXF) and a PstI restriction enzyme site upstream thereof had been introduced. The PCR conditions employed 35 cycles, each cycle involving an incubation at 95° C. for 1 minutes followed by 55° C. for 30 seconds followed by 72° C. for 1 minutes. The amplified DNA fragment thus obtained was cleaved with PstI and BssHII, and subjected to a low melting point agarose gel electrophoresis (NusieveGTG agarose; FMCbio), whereby accomplishing the purification and recovery. The DNA fragment thus purified and recovered was used as an insert fragment. Then, a GEM-mNXF which had been cleaved with PstI and BssHII and then BAP-treated was subjected to a low melting point agarose gel electrophoresis (Agarose L, Nippon Gene) to recover a DNA fragment. The recovered DNA fragment (0.1 µg) was used as a vector. This vector was ligated with the insert fragment (0.5 µg) described above using a T4 Ligase to obtain a pGEM-mNXF kozac into which a Kozac sequence (5'-CCAGCCACC-3') had been introduced immediately before the initiation codon of the present transcription regulatory factor (mNXF). The nucleotide sequence of the insert fragment was verified to be correct using a DNA sequencer (Model 3700; PE biosystems).

Then, this pGEM-mNXF kozac was cleaved simultaneously with 3 enzymes PstI, NotI and ScaI, and then subjected to a low melting point agarose electrophoresis to recover an mNXF kozac PstI-NotI-cleaved DNA fragment (about 2.5 kbp). The recovered DNA fragment was imparted with a blunt end using a T4 polymerase and then used as an insert fragment. After cleaving an RSV promoter-carrying pRC/RSV (Invitrogen) was cleaved with HindIII, imparted with a blunt end using a T4 polymerase, and subjected to a BAP treatment, whereby obtaining a vector. This vector (0.1 µg) was ligated with the insert fragment (0.5 µg) described above using a T4 Ligase to obtain (a) a pRC/RSV-mNXF-sense which is a plasmid expressing the sense strand of the mNXF kozac under the control of the RSV promoter and (b) a pRC/RVS-mNXFantisense which is a plasmid expressing the antisense strand of the mNXF kozac under the control of the RSV promoter. Whether the prepared plasmid was the desired plasmid or not was checked by investigating the nucleotide sequence of the margin between the vector and the inserted fragment. Among these plasmids, only the pRC/RSV-mNXFsense was employed in the following tests as a plasmid for expressing the present transcription regulatory factor (mNXF) in a mammalian cell.

(2-9-3) Preparation of pRC/RSV-hSim2kozac

As a plasmid expressing Sim2 in a mammalian cell, a pRC/RSV-hSim2kozac prepared in the section (2-4-5) described above was employed.

(2-9-4) Preparation of pRC/RSV-hClock kozac

A plasmid expressing Clock was prepared as described below.

First, a pBlue-hClock kozac was cleaved by the both restriction enzymes, i.e., EcoRV and SpeI. This was imparted with a blunt end using a T4 polymerase, and subjected to a low melting point agarose electrophoresis to recover a DNA fragment (about 2.5 kbp: containing clock translation sequence). The recovered DNA fragment was employed as an insert fragment. A pRC/RSV vector which had been cleaved with HindIII and then imparted with a blunt end using a T4 polymerase was employed as a vector, and this vector (0.1 µg) was ligated with the insert fragment (0.5 µg) using a T4 Ligase, whereby obtaining a pRC/RSV-hClock kozac.

(2-9-5) Preparation of pGL3-TATA-CMEx4

A reporter gene plasmid comprising 4 copies of a CME sequence (i.e., a DNA region to which Sim1 or Sim2 can be bound) upstream of a luciferase gene comprising a TATA minimum promoter was prepared as described below.

First, a double-stranded oligonucleotide was prepared by hybridizing two oligonucleotides (SEQ ID No.55: 5'-ctagc-ctagaaatttgtacgtgccacagactagaaatttgtacgtgccacagag-3', SEQ ID No.56: 5'-ctagctctgtggcacgta-caaatttctagtctgtggcacgtacaaatttctagg-3'). The resultant double-stranded oligonucleotide had 2 copies of a CME sequence (i.e., a DNA region to which Sim1 or Sim2 can be bound) and has a sticky end capable of binding to a NheI restriction enzyme cleavage fragment. The terminal of this oligonucleotide was phosphorylated using a T4 kinase, and connected in tandem using a T4 Ligase to obtain a binding reaction product. The resultant binding reaction product was subjected to a low melting point agarose gel electrophoresis (NusieveGTG agarose; FMCbio) to recover a DNA fragment in which two double-stranded oligonucleotides were connected in tandem. The recovered DNA fragment was used as an insert fragment. A pGL3-TATA vector which had been cleaved with NheI and then subjected to a BAP treatment was employed as a vector, and this vector (0.1 µg) was ligated with the insert fragment (0.5 µg) using a T4 Ligase to prepare a pGL3-TATA-CMEx4 which is a reporter gene plasmid comprising 4 copies of the CME sequence (i.e., a DNA region to which Sim1 or Sim2 can be bound) upstream of a luciferase gene comprising a TATA minimum promoter. The correct construction was verified by investigating the nucleotide sequence of the promoter part.

(2-9-6) Preparation of pGL3-TATA-(Ebox)x3

A reporter gene plasmid comprising an E-box upstream of a luciferase gene comprising a TATA minimum promoter was prepared as described below.

First, a double-stranded oligonucleotide was prepared by hybridizing two oligonucleotides (SEQ ID No.57: 5'-ctttagc-cacgtgacagtgtaagcacacgtgggccctcaagtccacgtgcagggac-3': SEQ ID No.58: 5'-tcgagtccctgcacgtggacttgagggc-ccacgtgtgcttacactgtcacgtggctaaaggtac-3'). The resultant double-stranded oligonucleotide had 3 copies of a Clock responsive sequence (i.e., E-box: Science (1998) 280, 1564-1567, N. Gekakis et. al.) and has a sticky end capable of binding to a KpnI and XhoI restriction enzyme cleavage fragment. The terminal of this oligonucleotide was phosphorylated using a T4 kinase, used as an insert fragment. A pGL3-TATA vector which had been cleaved with KpnI and XhoI and then subjected to a BAP treatment was employed as a vector, and this vector (0.1 µg) was ligated with the insert fragment (0.5 µg) using a T4 Ligase to prepare a pGL3-TATA-(Ebox)x3 which is a reporter gene plasmid comprising 3 copies of the Clock responsive sequence (i.e., E-box) upstream of a luciferase gene comprising a TATA minimum promoter. The correct construction was verified by investigating the nucleotide sequence of the promoter part.

(2-9-7) Reporter Assay for Verifying Transcription Promoting Ability of Inventive Transcription Activating Complex About $5 \times 10^6$ HeLa cells were cultured in a 10% FBS-supplemented DMEM medium (NISSUI SEIYAKU) at 37° C. in the presence of 5% $CO_2$ in a petri dish (Falcon) whose diameter was about 10 cm. On the next day, the cultured cells were dispersed by a trypsin treatment, washed twice with a FBS-free DMEM medium, and then dispersed again in a FBS-free DMEM medium at the cell density of $5 \times 10^6$. 0.4 ml of this cell dispersion was mixed with an appropriate combination (detailed in the table shown below) of the three plasmid, namely, the reporter gene plasmid prepared in the Section (2-9-5, 6) described above (for example 3 µg), the plasmid prepared in the Section (2-9-1, 2) described above which expresses a protein (for example 3 µg) and the plasmid prepared in the Section (2-9-3, 4) described above which expresses a protein (for example 3 µg), and the mixture was transferred into an electroporation cuvette, where a transfection was conducted by an electroporation method employing a Gene pulser (BIORAD) under the conditions involving 220V and 950 µF. After the transfection, the culture medium was replaced with a 10% FBS-supplemented DMEM, and then further cultured in a 6-well plate for about 24 hours.

TABLE 1

| FIG. No. | Abscissa Column | Plasmid combination: Amount (μg) | | | | | Total amount (pRC/RSV as remainder) |
|---|---|---|---|---|---|---|---|
| | | Clock | Sim2 | mNXF | Arnt2 | Reporter gene | |
| FIG. 7 | A | 0 | 0 | 0 | 2 | 2 | 9 |
| | B | 0 | 0 | 1 | 2 | 2 | 9 |
| | C | 0 | 0 | 2 | 2 | 2 | 9 |
| | D | 0 | 0 | 3 | 2 | 2 | 9 |
| | E | 0 | 0 | 2 | 2 | 2 | 9 |
| | F | 0 | 1 | 2 | 2 | 2 | 9 |
| | G | 0 | 2 | 2 | 2 | 2 | 9 |
| | H | 0 | 3 | 2 | 2 | 2 | 9 |
| | I | 0 | 0 | 2 | 2 | 2 | 9 |
| | J | 1 | 0 | 2 | 2 | 2 | 9 |
| | K | 2 | 0 | 2 | 2 | 2 | 9 |
| | L | 3 | 0 | 2 | 2 | 2 | 9 |

Figure 8:
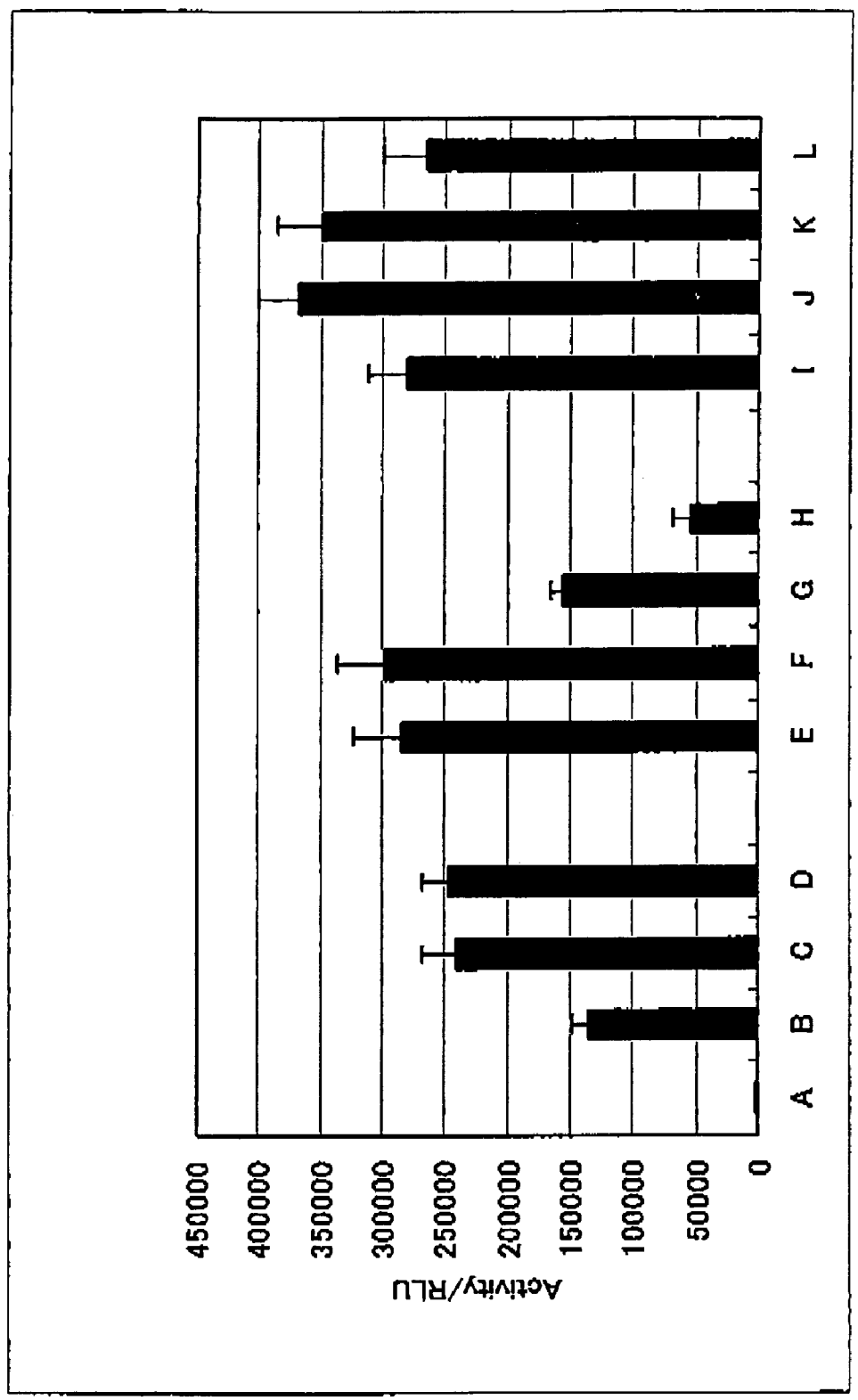
FIG. 8 shows the results of a reporter assay (in a system employing a reporter gene bound to a CME sequence-carrying promoter in a functional manner) for verifying the transcription promoting ability of an inventive transcription activating complex. The abscissa represents a combination of an Arnt2 which is a present ARNT family transcription coupling factor with any of various transcription regulatory factors (Clock, NXF or Sim2). Those up to the fourth (A, B, C, D) from the left end correspond to the test system for the dose dependency of the present transcription regulatory factor (NXF)-induced reporter gene transcription activity in the presence of the Arnt2 which is a present ARNT family transcription coupling factor. Those from the fifth to the eighth (E, F, G, H) from the left end correspond to the test system for the Sim2 influence on the present transcription regulatory factor (NXF)-induced reporter gene transcription activity in the presence of the Arnt2 which is a present ARNT family transcription coupling factor. Those from the ninth to the twelfth (I, J, K, L) from the left end correspond to the test system for the Clock influence on the present transcription regulatory factor (NXF)-induced reporter gene transcription activity in the presence of the Arnt2 which is a present ARNT family transcription coupling factor.

| | Column | Sim2 | mNXF | Arnt2 | Reporter gene | Total amount (pRC/RSV as remainder) |
|---|---|---|---|---|---|---|
| FIG. 8 | a | 0 | 2 | 2 | 2 | 9 |
| | b | 2 | 0 | 2 | 2 | 9 |
| | c | 2 | 1 | 2 | 2 | 9 |
| | d | 2 | 2 | 2 | 2 | 9 |
| | e | 2 | 3 | 2 | 2 | 9 |

Then, the culture medium was removed from the wells, and the cells depositing on the plate wall were washed twice with PBS(−), and then 200 μl per well of a 5-fold diluted PGC 50 (TOYO INK) was added and allowed to stand at room temperature for 30 minutes. 20 μl Aliquots of this cell suspension were dispensed into a opaque plate (Corning International K.K), and this plate was mounted on a luminometer LB96P (Berthold Japan, Co. Ltd.) fitted with an enzyme substrate automatic injector, and after dispensing 50 μl of the substrate solution PGL100 (TOYO INK) automatically the luciferase activity of each well was determined.

Figure 7:
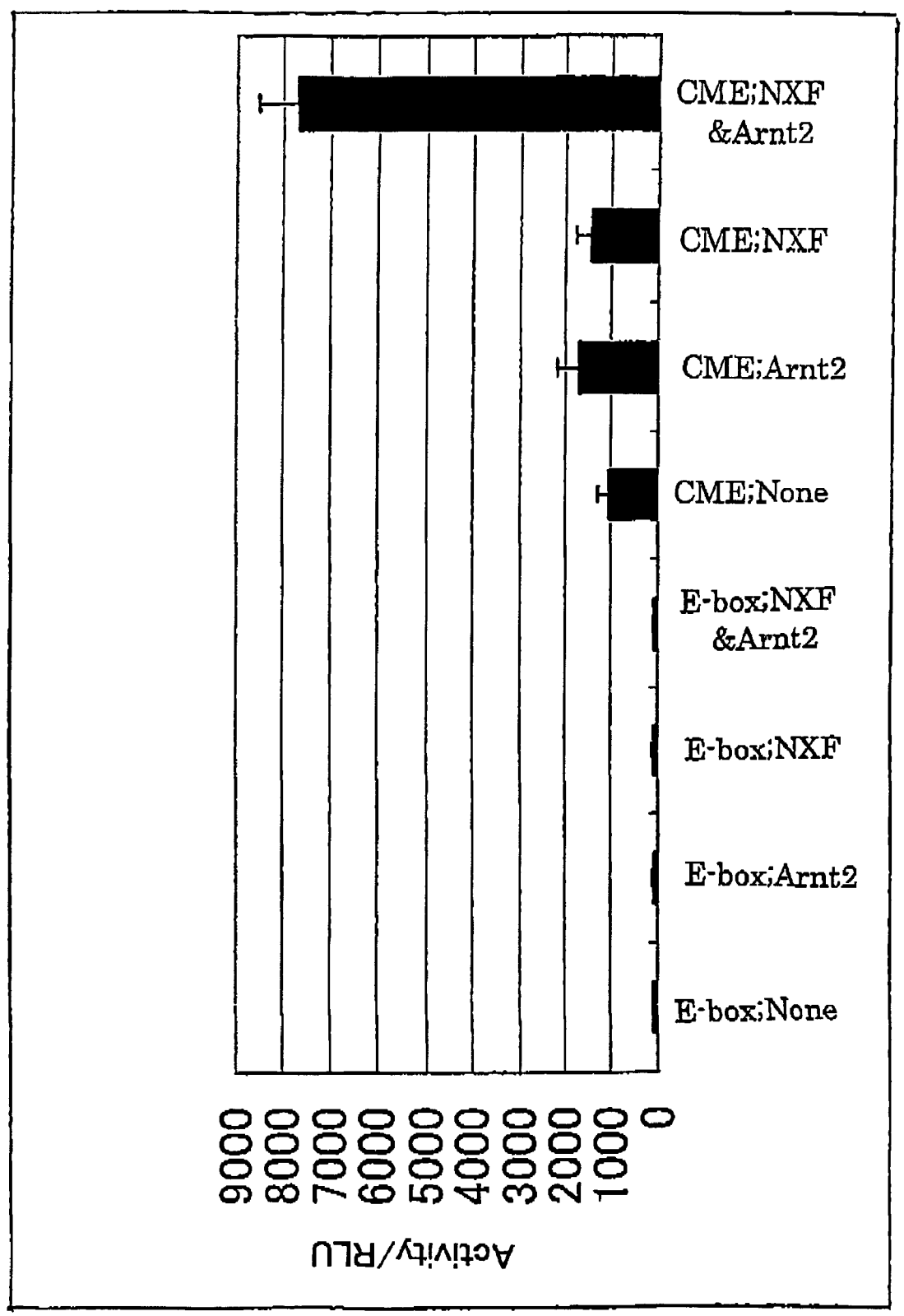
FIG. 7 shows the results of a reporter assay for verifying the transcription promoting ability of an inventive transcription activating complex. The abscissa represents a combination of an responsive sequence with a transcription regulatory factor and/or a transcription coupling factor plus transcription regulatory factor employed in each test system. Those up to the fourth from the left end are of the system employing an E-box sequences which is a Clock responsive sequence, which corresponds to the test system for comparison. On the other hand, those starting from the fifth from the left end are of the system employing a CME sequence, which corresponds to the test system according to the invention. The ordinate represents a luciferase activity level, which is an index value representing an activity on the transcription of the reporter gene. The right end indicates a potent transcription promoting ability of an inventive transcription activating complex (i.e., a coexpression of an Arnt2 which is a present ARNT family transcription coupling factor together with a present transcription regulatory factor (NXF)) on the reporter gene under the control of the CME sequence.

As evident from FIG. 7, the expression of the reporter gene controlled by the E-box sequence as a Clock responsive sequence was not influenced in the case of (a) the expression only of Arnt2 which is a present ARNT transcription coupling factor, (b) the expression only of the present transcription regulatory factor (NXF) or (c) the expression of the inventive transcription activating complex (i.e., co-expression of Arnt2 which is a present ARNT transcription coupling factor and the present transcription regulatory factor (NXF)).

On the other hand, the expression of the reporter gene controlled by the CEM sequence was not influenced in the cases of (a') the expression only of Arnt2 which is a present ARNT transcription coupling factor or (b') the expression only of the present transcription regulatory factor (NXF), but reflected a potent transcription promoting ability in the case of (c') the expression of the inventive transcription activating complex (i.e., co-expression of Arnt2 which is a present ARNT transcription coupling factor and the present transcription regulatory factor (NXF)).

Accordingly, it was revealed that the DNA region to which the inventive transcription activating complex can be bound is identical to the CME sequence, and the inventive transcription activating complex has a transcription promoting effect on the promoter containing the CME sequence.

Figure 9:
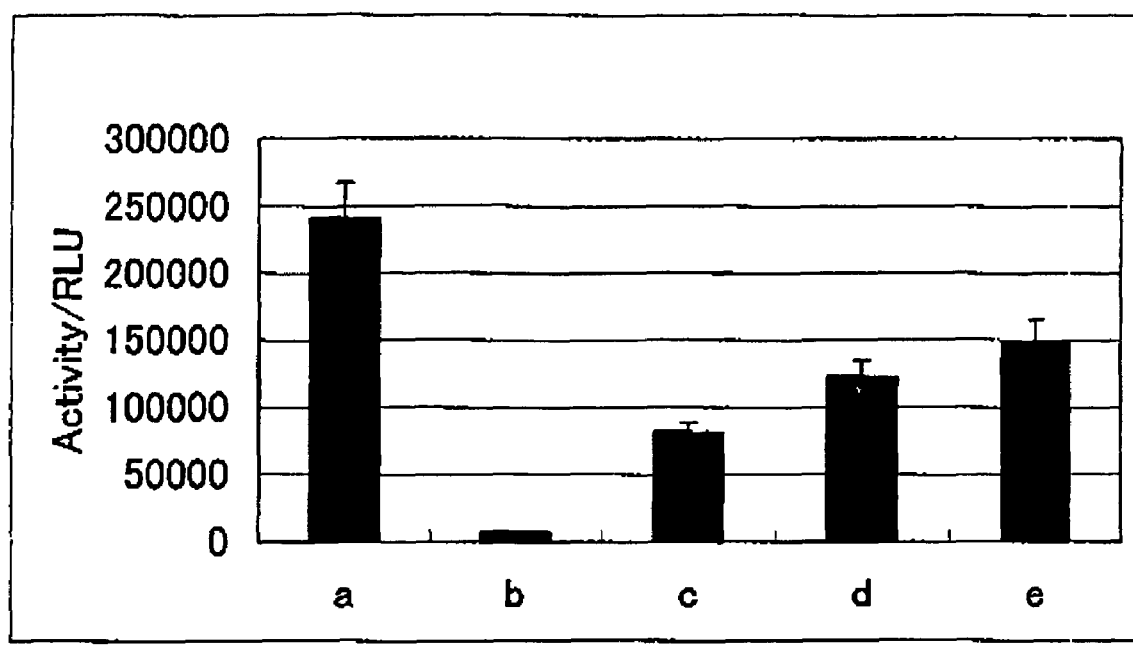
FIG. 9 shows the results of a reporter assay (in a system employing a reporter gene bound to a CME sequence-carrying promoter in a functional manner) for verifying the transcription promoting ability of an inventive transcription activating complex. The abscissa represents a combination of an Arnt2 which is a present ARNT family transcription coupling factor with any of various transcription regulatory factors (NXF and/or Sim2). Those starting from the second (b, c, d, e) from the left end correspond to the test system for the influence of a present transcription regulatory factor (NXF) on the present transcription regulatory factor (NXF)-induced reporter gene transcription activity in the presence of a Sim2 when an Arnt2 which is a present ARNT family transcription coupling factor is coexisting. The left end (a) is of the test system relating to the present transcription regulatory factor (NXF)-induced reporter gene transcription activity in the absence of a transcription regulating factor Sim2 when an Arnt2 which is a present ARNT family transcription coupling factor is coexisting, which corresponds to a control.

FIG. 8 also indicates that the present transcription regulatory factor (NXF) activated the transcription of the reporter gene in a dose-dependent manner in the presence of Arnt2 which is a present ARNT transcription coupling factor (see, A, B, C, D in FIG. 8). In the system where the transcription activity once increased by the present transcription activating complex was then exposed to the added Sim2 (E, F, G, H in FIG. 8), a dose dependent inhibition of the reporter gene transcription was noted. In the system where a negative control Clock was added instead of Sim2 (I, J, K, L in FIG. 8), no inhibition on the reporter gene transcription was noted, Furthermore, FIG. 9 revealed that in the system where the transcription activity once inhibited by the addition of Sim2 in the presence of Arnt2 was then exposed to the added present transcription regulatory factor (mNXF) (b, c, d, e in FIG. 9), a release from the inhibition of the transcription by Sim2 was observed in a dose dependent manner, resulting in the change in the condition toward the transcription activation. Thus, a release from the Sim2-induced inhibition of the transcription of the reporter gene operably connected to the promoter containing the CME sequence was confirmed.

INDUSTRIAL APPLICABILITY

The present invention is successful in providing a transcription activating complex in which a transcription regulatory factor/ARNT family transcription coupling factor heterodimer complex exhibits a promotive action on the CME sequence. By allowing the transcription activating complex to act competitively with a Sim2/ARNT family transcription coupling factor heterodimer complex, a therapy in a Down's syndrome patient is expected.

Free Text in Sequence Listing

SEQ ID No.7
  Designed oligonucleotide primer for PCR

SEQ ID No.8
  Designed oligonucleotide primer for PCR

SEQ ID No.9
  Designed oligonucleotide primer for PCR

SEQ ID No.10
  Designed oligonucleotide primer for PCR

SEQ ID No.11
Designed oligonucleotide for DNA region to which the protein can be bound SEQ ID No.12
Designed oligonucleotide for DNA region to which the protein can be bound SEQ ID No.13
Designed oligonucleotide for DNA region to which the protein can be bound SEQ ID No.14
Designed oligonucleotide for DNA region to which the protein can be bound SEQ ID No.15
Designed oligonucleotide for DNA region to which the protein can be bound SEQ ID No.16
Designed oligonucleotide for DNA region to which the protein can be bound SEQ ID No.17
Designed oligonucleotide for plasmid construction SEQ ID No.18
Designed oligonucleotide for plasmid construction SEQ ID No.19
Designed oligonucleotide for plasmid construction SEQ ID No.20
Designed oligonucleotide for plasmid construction SEQ ID No.21
Designed oligonucleotide for plasmid construction SEQ ID No.22
Designed oligonucleotide for plasmid construction SEQ ID No.23
Designed oligonucleotide for plasmid construction SEQ ID No.24
Designed oligonucleotide for plasmid construction SEQ ID No.25
Designed oligonucleotide primer for PCR SEQ ID No.26
Designed oligonucleotide primer for PCR SEQ ID No.27
Designed oligonucleotide primer for PCR SEQ ID No.28
Designed oligonucleotide primer for PCR SEQ ID No.29
Designed oligonucleotide primer for PCR SEQ ID No.30
Designed oligonucleotide primer for PCR SEQ ID No.31
Designed oligonucleotide primer for PCR SEQ ID No.32
Designed oligonucleotide primer for PCR SEQ ID No.33
Designed oligonucleotide primer for PCR SEQ ID No.34
Designed oligonucleotide primer for PCR SEQ ID No.35
Designed oligonucleotide primer for PCR SEQ ID No.36
Designed oligonucleotide primer for PCR SEQ ID No.37
Designed oligonucleotide primer for PCR SEQ ID No.38
Designed oligonucleotide primer for PCR SEQ ID No.39
Designed oligonucleotide primer for PCR SEQ ID No.40
Designed oligonucleotide primer for PCR SEQ ID No.41
Designed oligonucleotide primer for PCR SEQ ID No.42
Designed oligonucleotide primer for PCR SEQ ID No.43
Designed oligonucleotide primer for PCR SEQ ID No.44
Designed oligonucleotide primer for PCR SEQ ID No.45
Designed oligonucleotide primer for PCR SEQ ID No.46
Designed oligonucleotide primer for PCR SEQ ID No.47
Designed oligonucleotide primer for PCR SEQ ID No.48
Designed oligonucleotide primer for PCR SEQ ID No.49
Designed oligonucleotide for a CME double-stranded oligonucleotide SEQ ID No.50
Designed oligonucleotide for a CME double-stranded oligonucleotide SEQ ID No.51
Designed oligonucleotide for a E-box double-stranded oligonucleotide SEQ ID No.52
Designed oligonucleotide for a E-box double-stranded oligonucleotide SEQ ID No.53
Designed oligonucleotide primer for PCR SEQ ID No.54
Designed oligonucleotide primer for PCR SEQ ID No.55
Designed oligonucleotide for plasmid construction SEQ ID No.56
Designed oligonucleotide for plasmid construction SEQ ID No.57
Designed oligonucleotide for plasmid construction SEQ ID No.58
Designed oligonucleotide for plasmid construction

The invention claimed is:

1. An in vitro complex of a transcription coupling factor of any one of ARNT 1 to 3 and a transcription regulatory factor comprising any of the amino acid sequences shown below, which is a transcription activating complex that binds to a DNA region (5'-ACGTG-3', SEQ ID NO: 16) in competition with a transcription inhibiting complex of a Sim2 as a transcription regulatory factor and a transcription coupling factor of any one of ARNT 1 to 3 and which promotes transcription of a gene located downstream of the DNA region, wherein the amino acid sequences are:

(a) the amino acid sequence represented by any one of SEQ ID NOs: 1 to 3, (b) an amino acid sequence of a protein comprising an amino acid sequence exhibiting an amino acid identity of 90% or more to the amino acid sequence represented by any of SEQ ID NOs: 1 to 3 and regulates transcription of a gene located downstream of a DNA region comprising the nucleotide sequence of SEQ ID NO:16.

2. An in vitro host cell obtained by introducing one or more vectors encoding a transcription activating complex according to claim 1.

3. An in vitro host cell obtained by introducing a single vector comprising both of the DNAs shown below or several vectors comprising such DNAs independently into a host cell, wherein the DNAs are:

(1) a DNA comprising a nucleotide sequence encoding an amino acid sequence of a transcription coupling factor of any one of ARNT 1 to 3, and (2) a DNA comprising a nucleotide sequence encoding any of the amino acid sequences shown below:

(a) the amino acid sequence represented by any one of SEQ ID NOs: 1 to 3, (b) an amino acid sequence of a protein comprising an amino acid sequence exhibiting an amino acid identity of 90% or more to the amino acid sequence represented by any one of SEQ ID NOs: 1 to 3 and also having an ability to regulate transcription of a gene located downstream of a DNA region comprising the nucleotide sequence of SEQ ID NO:16.

4. An in vitro host cell according to claim 2 or 3 further containing a DNA of a reporter gene comprising a promoter, as being operably connected thereto, said promoter contains DNA region (5'-ACGTG-3, SEQ ID NO: 16) to which the transcription inhibiting complex of a Sim2 as a transcription regulatory factor and a transcription coupling factor of any one of ARNT 1 to 3 can be bound.

5. A method to evaluate regulation of transcription, an in vitro complex of a transcription coupling factor of any one of ARNT 1 to 3 and a transcription regulatory factor comprising any of the amino acid sequences shown below, which is a transcription activating complex that binds to a DNA region (5'-ACGTG-3', SEQ ID NO: 16) in competition with a transcription inhibiting complex of a Sim2 as a transcription regulatory factor and a transcription coupling factor of any one of ARNT 1 to 3 and which promotes transcription of a gene located downstream of the DNA region, wherein the amino acid sequences are:
- (a) the amino acid sequence represented by any one of SEQ ID NOs: 1 to 3,
- (b) an amino acid sequence of a protein comprising an amino acid sequence exhibiting an amino acid identity of 90% or more to the amino acid sequence represented by any of SEQ ID NOs: 1 to 3 and regulates transcription of a gene located downstream of a DNA region comprising the nucleotide sequence of SEQ ID NO: 16 which comprises:
- (1) contacting a test substance with an in vitro host cell according to claim 4;
- (2) measuring an expression level of the reporter gene possessed by the in vitro host cell; and,
- (3) evaluating the substance for its ability of regulating the transcription promoting ability possessed by the transcription activating complex based on the expression level correlating with the level measured in (2).

6. A searching method comprising selecting a substance having an ability to regulate the transcription promoting ability possessed by the transcription activating complex based on a regulating ability evaluated by the method according to claim 5.

* * * * *

SEQUENCE LISTING

<160> NUMBER OF SEQ ID NOS: 60

<210> SEQ ID NO 1
<211> LENGTH: 802
<212> TYPE: PRT
<213> ORGANISM: Homo sapiens

<400> SEQUENCE: 1

Met Tyr Arg Ser Thr Lys Gly Ala Ser Lys Ala Arg Arg Asp Gln Ile
1               5                   10                  15

Asn Ala Glu Ile Arg Asn Leu Lys Glu Leu Leu Pro Leu Ala Glu Ala
            20                  25                  30

Asp Lys Val Arg Leu Ser Tyr Leu His Ile Met Ser Leu Ala Cys Ile
        35                  40                  45

Tyr Thr Arg Lys Gly Val Phe Phe Ala Gly Thr Pro Leu Ala Gly
    50                  55                  60

Pro Thr Gly Leu Leu Ser Ala Gln Glu Leu Glu Asp Ile Val Ala Ala
65                  70                  75                  80

Leu Pro Gly Phe Leu Leu Val Phe Thr Ala Glu Gly Lys Leu Leu Tyr
                85                  90                  95

Leu Ser Glu Ser Val Ser Glu His Leu Gly His Ser Met Val Asp Leu
            100                 105                 110

Val Ala Gln Gly Asp Ser Ile Tyr Asp Ile Ile Asp Pro Ala Asp His
        115                 120                 125

Leu Thr Val Arg Gln Gln Leu Thr Leu Pro Ser Ala Leu Asp Thr Asp
    130                 135                 140

Arg Leu Phe Arg Cys Arg Phe Asn Thr Ser Lys Ser Leu Arg Arg Gln
145                 150                 155                 160

Ser Ala Gly Asn Lys Leu Val Leu Ile Arg Gly Arg Phe His Ala His
                165                 170                 175

Pro Pro Gly Ala Tyr Trp Ala Gly Asn Pro Val Phe Thr Ala Phe Cys
            180                 185                 190

Ala Pro Leu Glu Pro Arg Pro Arg Pro Gly Pro Gly Pro Gly Pro Gly
        195                 200                 205

Pro Ala Ser Leu Phe Leu Ala Met Phe Gln Ser Arg His Ala Lys Asp
    210                 215                 220

Leu Ala Leu Leu Asp Ile Ser Glu Ser Val Leu Ile Tyr Leu Gly Phe
225                 230                 235                 240

Glu Arg Ser Glu Leu Leu Cys Lys Ser Trp Tyr Gly Leu Leu His Pro
                245                 250                 255

Glu Asp Leu Ala His Ala Ser Ala Gln His Tyr Arg Leu Leu Ala Glu
            260                 265                 270

Ser Gly Asp Ile Gln Ala Glu Met Val Val Arg Leu Gln Ala Lys Thr
        275                 280                 285

Gly Gly Trp Ala Trp Ile Tyr Cys Leu Leu Tyr Ser Glu Gly Pro Glu
    290                 295                 300

Gly Pro Ile Thr Ala Asn Asn Tyr Pro Ile Ser Asp Met Glu Ala Trp
305                 310                 315                 320

Ser Leu Arg Gln Gln Leu Asn Ser Glu Asp Thr Gln Ala Ala Tyr Val
                325                 330                 335

Leu Gly Thr Pro Thr Met Leu Pro Ser Phe Pro Glu Asn Ile Leu Ser
            340                 345                 350

Gln Glu Glu Cys Ser Ser Thr Asn Pro Leu Phe Thr Ala Ala Leu Gly

-continued

```
                355                 360                 365
Ala Pro Arg Ser Thr Ser Phe Pro Ser Ala Pro Glu Leu Ser Val Val
    370                 375                 380
Ser Ala Ser Glu Glu Leu Pro Arg Pro Ser Lys Glu Leu Asp Phe Ser
385                 390                 395                 400
Tyr Leu Thr Phe Pro Ser Gly Pro Glu Pro Ser Leu Gln Ala Glu Leu
                405                 410                 415
Ser Lys Asp Leu Val Cys Thr Pro Pro Tyr Thr Pro His Gln Pro Gly
            420                 425                 430
Gly Cys Ala Phe Leu Phe Ser Leu His Glu Pro Phe Gln Thr His Leu
                435                 440                 445
Pro Thr Pro Ser Ser Thr Leu Gln Glu Gln Leu Thr Pro Ser Thr Ala
    450                 455                 460
Thr Phe Ser Asp Gln Leu Thr Pro Ser Ser Ala Thr Phe Pro Asp Pro
465                 470                 475                 480
Leu Thr Ser Pro Leu Gln Gly Gln Leu Thr Glu Thr Ser Val Arg Ser
                485                 490                 495
Tyr Glu Asp Gln Leu Thr Pro Cys Thr Ser Thr Phe Pro Asp Gln Leu
            500                 505                 510
Leu Pro Ser Thr Ala Thr Phe Pro Glu Pro Leu Gly Ser Pro Ala His
            515                 520                 525
Glu Gln Leu Thr Pro Pro Ser Thr Ala Phe Gln Ala His Leu Asp Ser
    530                 535                 540
Pro Ser Gln Thr Phe Pro Glu Gln Leu Ser Pro Asn Pro Thr Lys Thr
545                 550                 555                 560
Tyr Phe Ala Gln Glu Gly Cys Ser Phe Leu Tyr Glu Lys Leu Pro Pro
                565                 570                 575
Ser Pro Ser Ser Pro Gly Asn Gly Asp Cys Thr Leu Leu Ala Leu Ala
            580                 585                 590
Gln Leu Arg Gly Pro Leu Ser Val Asp Val Pro Leu Val Pro Glu Gly
        595                 600                 605
Leu Leu Thr Pro Glu Ala Ser Pro Val Lys Gln Ser Phe Phe His Tyr
    610                 615                 620
Ser Glu Lys Glu Gln Asn Glu Ile Asp Arg Leu Ile Gln Gln Ile Ser
625                 630                 635                 640
Gln Leu Ala Gln Gly Met Asp Arg Pro Phe Ser Ala Glu Ala Gly Thr
                645                 650                 655
Gly Gly Leu Glu Pro Leu Gly Gly Leu Glu Pro Leu Asp Ser Asn Leu
            660                 665                 670
Ser Leu Ser Gly Ala Gly Pro Pro Val Leu Ser Leu Asp Leu Lys Pro
        675                 680                 685
Trp Lys Cys Gln Glu Leu Asp Phe Leu Ala Asp Pro Asp Asn Met Phe
    690                 695                 700
Leu Glu Glu Thr Pro Val Glu Asp Ile Phe Met Asp Leu Ser Thr Pro
705                 710                 715                 720
Asp Pro Ser Glu Glu Trp Gly Ser Gly Asp Pro Glu Ala Glu Gly Pro
                725                 730                 735
Gly Gly Ala Pro Ser Pro Cys Asn Asn Leu Ser Pro Glu Asp His Ser
            740                 745                 750
Phe Leu Glu Asp Leu Ala Thr Tyr Glu Thr Ala Phe Glu Thr Gly Val
        755                 760                 765
Ser Ala Phe Pro Tyr Asp Gly Phe Thr Asp Glu Leu His Gln Leu Gln
    770                 775                 780
```

```
Ser Gln Val Gln Asp Ser Phe His Glu Asp Gly Ser Gly Gly Glu Pro
785                 790                 795                 800

Thr Phe

<210> SEQ ID NO 2
<211> LENGTH: 802
<212> TYPE: PRT
<213> ORGANISM: Mus musculus

<400> SEQUENCE: 2

Met Tyr Arg Ser Thr Lys Gly Ala Ser Lys Ala Arg Arg Asp Gln Ile
1               5                   10                  15

Asn Ala Glu Ile Arg Asn Leu Lys Glu Leu Leu Pro Leu Ala Glu Ala
            20                  25                  30

Asp Lys Val Arg Leu Ser Tyr Leu His Ile Met Ser Leu Ala Cys Ile
        35                  40                  45

Tyr Thr Arg Lys Gly Val Phe Phe Ala Gly Gly Thr Pro Leu Ala Gly
    50                  55                  60

Pro Thr Gly Leu Leu Ser Ala Gln Glu Leu Glu Asp Ile Val Ala Ala
65                  70                  75                  80

Leu Pro Gly Phe Leu Leu Val Phe Thr Ala Glu Gly Lys Leu Leu Tyr
                85                  90                  95

Leu Ser Glu Ser Val Ser Glu His Leu Gly His Ser Met Val Asp Leu
            100                 105                 110

Val Ala Gln Gly Asp Ser Ile Tyr Asp Ile Ile Asp Pro Ala Asp His
        115                 120                 125

Leu Thr Val Arg Gln Gln Leu Thr Met Pro Ser Ala Leu Asp Ala Asp
130                 135                 140

Arg Leu Phe Arg Cys Arg Phe Asn Thr Ser Lys Ser Leu Arg Arg Gln
145                 150                 155                 160

Ser Ser Gly Asn Lys Leu Val Leu Ile Arg Gly Arg Phe His Ala His
                165                 170                 175

Pro Pro Gly Ala Tyr Trp Ala Gly Asn Pro Val Phe Thr Ala Phe Cys
            180                 185                 190

Ala Pro Leu Glu Pro Arg Pro Arg Pro Gly Pro Gly Pro Gly Pro Gly
        195                 200                 205

Pro Gly Pro Ala Ser Leu Phe Leu Ala Met Phe Gln Ser Arg His Ala
    210                 215                 220

Lys Asp Leu Ala Leu Leu Asp Val Ser Glu Ser Val Leu Ile Tyr Leu
225                 230                 235                 240

Gly Phe Glu Arg Ser Glu Leu Leu Cys Lys Ser Trp Tyr Gly Leu Leu
                245                 250                 255

His Pro Glu Asp Leu Ala Gln Ala Ser Ser Gln His Tyr Arg Leu Leu
            260                 265                 270

Ala Glu Ser Gly Asp Ile Gln Ala Glu Met Val Val Arg Leu Gln Ala
        275                 280                 285

Lys His Gly Gly Trp Thr Trp Ile Tyr Cys Met Leu Tyr Ser Glu Gly
    290                 295                 300

Pro Glu Gly Pro Phe Thr Ala Asn Asn Tyr Pro Ile Ser Asp Thr Glu
305                 310                 315                 320

Ala Trp Ser Leu Arg Gln Gln Leu Asn Ser Glu Asp Thr Gln Ala Ala
                325                 330                 335

Tyr Val Leu Gly Thr Pro Ala Val Leu Pro Ser Phe Ser Glu Asn Val
            340                 345                 350
```

```
Phe Ser Gln Glu Gln Cys Ser Asn Pro Leu Phe Thr Pro Ser Leu Gly
            355                 360                 365

Thr Pro Arg Ser Ala Ser Phe Pro Arg Ala Pro Glu Leu Gly Val Ile
        370                 375                 380

Ser Thr Pro Glu Glu Leu Pro Gln Pro Ser Lys Glu Leu Asp Phe Ser
385                 390                 395                 400

Tyr Leu Pro Phe Pro Ala Arg Pro Glu Pro Ser Leu Gln Ala Asp Leu
                405                 410                 415

Ser Lys Asp Leu Val Cys Thr Pro Pro Tyr Thr Pro His Gln Pro Gly
            420                 425                 430

Gly Cys Ala Phe Leu Phe Ser Leu His Glu Pro Phe Gln Thr His Leu
            435                 440                 445

Pro Pro Pro Ser Ser Ser Leu Gln Glu Gln Leu Thr Pro Ser Thr Val
        450                 455                 460

Thr Phe Ser Glu Gln Leu Thr Pro Ser Ser Ala Thr Phe Pro Asp Pro
465                 470                 475                 480

Leu Thr Ser Ser Leu Gln Gly Gln Leu Thr Glu Ser Ser Ala Arg Ser
                485                 490                 495

Phe Glu Asp Gln Leu Thr Pro Cys Thr Ser Ser Phe Pro Asp Gln Leu
            500                 505                 510

Leu Pro Ser Thr Ala Thr Phe Pro Glu Pro Leu Gly Ser Pro Ala His
            515                 520                 525

Glu Gln Leu Thr Pro Pro Ser Thr Ala Phe Gln Ala His Leu Asn Ser
        530                 535                 540

Pro Ser Gln Thr Phe Pro Glu Gln Leu Ser Pro Asn Pro Thr Lys Thr
545                 550                 555                 560

Tyr Phe Ala Gln Glu Gly Cys Ser Phe Leu Tyr Glu Lys Leu Pro Pro
                565                 570                 575

Ser Pro Ser Ser Pro Gly Asn Gly Asp Cys Thr Leu Leu Ala Leu Ala
            580                 585                 590

Gln Leu Arg Gly Pro Leu Ser Val Asp Val Pro Leu Val Pro Glu Gly
            595                 600                 605

Leu Leu Thr Pro Glu Ala Ser Pro Val Lys Gln Ser Phe Phe His Tyr
        610                 615                 620

Thr Glu Lys Glu Gln Asn Glu Ile Asp Arg Leu Ile Gln Gln Ile Ser
625                 630                 635                 640

Gln Leu Ala Gln Gly Val Asp Arg Pro Phe Ser Ala Glu Ala Gly Thr
                645                 650                 655

Gly Gly Leu Glu Pro Leu Gly Gly Leu Glu Pro Leu Asn Pro Asn Leu
            660                 665                 670

Ser Leu Ser Gly Ala Gly Pro Pro Val Leu Ser Leu Asp Leu Lys Pro
            675                 680                 685

Trp Lys Cys Gln Glu Leu Asp Phe Leu Val Asp Pro Asp Asn Leu Phe
        690                 695                 700

Leu Glu Glu Thr Pro Val Glu Asp Ile Phe Met Asp Leu Ser Thr Pro
705                 710                 715                 720

Asp Pro Asn Gly Glu Trp Gly Ser Gly Asp Pro Glu Ala Glu Val Pro
                725                 730                 735

Gly Gly Thr Leu Ser Pro Cys Asn Asn Leu Ser Pro Glu Asp His Ser
            740                 745                 750

Phe Leu Glu Asp Leu Ala Thr Tyr Glu Thr Ala Phe Glu Thr Gly Val
            755                 760                 765
```

```
Ser Thr Phe Pro Tyr Glu Gly Phe Ala Asp Glu Leu His Gln Leu Gln
    770                 775                 780

Ser Gln Val Gln Asp Ser Phe His Glu Asp Gly Ser Gly Gly Glu Pro
785                 790                 795                 800

Thr Phe

<210> SEQ ID NO 3
<211> LENGTH: 802
<212> TYPE: PRT
<213> ORGANISM: Rattus norvegicus

<400> SEQUENCE: 3

Met Tyr Arg Ser Thr Lys Gly Ala Ser Lys Ala Arg Arg Asp Gln Ile
1               5                   10                  15

Asn Ala Glu Ile Arg Asn Leu Lys Glu Leu Leu Pro Leu Ala Glu Ala
            20                  25                  30

Asp Lys Val Arg Leu Ser Tyr Leu His Ile Met Ser Leu Ala Cys Ile
        35                  40                  45

Tyr Thr Arg Lys Gly Val Phe Phe Ala Gly Gly Thr Pro Leu Ala Gly
    50                  55                  60

Pro Thr Gly Leu Leu Ser Ala Gln Glu Leu Glu Asp Ile Val Ala Ala
65                  70                  75                  80

Leu Pro Gly Phe Leu Leu Val Phe Thr Ala Glu Gly Lys Leu Leu Tyr
                85                  90                  95

Leu Ser Glu Ser Val Ser Glu His Leu Gly His Ser Met Val Asp Leu
            100                 105                 110

Val Ala Gln Gly Asp Ser Ile Tyr Asp Ile Ile Asp Pro Ala Asp His
        115                 120                 125

Leu Thr Val Arg Gln Gln Leu Thr Met Pro Ser Ala Leu Asp Ala Asp
    130                 135                 140

Arg Leu Phe Arg Cys Arg Phe Asn Thr Ser Lys Ser Leu Arg Arg Gln
145                 150                 155                 160

Ser Ala Gly Asn Lys Leu Val Leu Ile Arg Gly Arg Phe His Ala His
                165                 170                 175

Pro Pro Gly Ala Tyr Trp Ala Gly Asn Pro Val Phe Thr Ala Phe Cys
            180                 185                 190

Ala Pro Leu Glu Pro Arg Pro Arg Pro Gly Pro Gly Pro Gly Pro Gly
        195                 200                 205

Pro Gly Pro Ala Ser Leu Phe Leu Ala Met Phe Gln Ser Arg His Ala
    210                 215                 220

Lys Asp Leu Ala Leu Leu Asp Ile Ser Glu Ser Val Leu Ile Tyr Leu
225                 230                 235                 240

Gly Phe Glu Arg Ser Glu Leu Leu Cys Lys Ser Trp Tyr Gly Leu Leu
                245                 250                 255

His Pro Glu Asp Leu Ala His Ala Ser Ser Gln His Tyr Arg Leu Leu
            260                 265                 270

Ala Glu Asn Gly Asp Ile Gln Ala Glu Met Val Val Arg Leu Gln Ala
        275                 280                 285

Lys His Gly Gly Trp Thr Trp Ile Tyr Cys Met Leu Tyr Ser Asp Gly
    290                 295                 300

Pro Glu Gly Pro Ile Thr Ala Asn Asn Tyr Pro Ile Ser Asp Thr Glu
305                 310                 315                 320

Ala Trp Ser Leu Arg Gln Gln Leu Asn Ser Glu Asn Thr Gln Ala Ala
                325                 330                 335
```

```
Tyr Val Leu Gly Thr Pro Ala Val Leu Pro Ser Phe Ser Glu Asn Val
            340                 345                 350

Phe Ser Gln Glu His Cys Ser Asn Pro Leu Phe Thr Pro Ala Leu Gly
            355                 360                 365

Thr Pro Arg Ser Ala Ser Phe Pro Arg Ala Pro Glu Leu Gly Val Ile
            370                 375                 380

Ser Thr Ser Glu Glu Leu Ala Gln Pro Ser Lys Glu Leu Asp Phe Ser
385                 390                 395                 400

Tyr Leu Pro Phe Pro Ala Arg Pro Glu Pro Ser Leu Gln Ala Asp Leu
            405                 410                 415

Ser Lys Asp Leu Val Cys Thr Pro Pro Tyr Thr Pro His Gln Pro Gly
            420                 425                 430

Gly Cys Ala Phe Leu Phe Ser Leu His Glu Pro Phe Gln Thr His Leu
            435                 440                 445

Pro Pro Pro Ser Ser Ser Leu Gln Glu Gln Leu Thr Pro Ser Thr Val
            450                 455                 460

Thr Phe Ser Glu Gln Leu Thr Pro Ser Ser Ala Thr Phe Pro Asp Pro
465                 470                 475                 480

Leu Thr Ser Ser Leu Gln Gly Gln Leu Thr Glu Ser Ser Ala Arg Ser
            485                 490                 495

Phe Glu Glu Gln Leu Thr Pro Cys Thr Ser Thr Phe Pro Asp Gln Leu
            500                 505                 510

Leu Pro Ser Thr Ala Thr Phe Pro Glu Pro Leu Gly Ser Pro Thr His
            515                 520                 525

Glu Gln Leu Thr Pro Pro Ser Thr Ala Phe Gln Ala His Leu Asn Ser
            530                 535                 540

Pro Ser Gln Thr Phe Pro Glu Gln Leu Ser Pro Asn Pro Thr Lys Thr
545                 550                 555                 560

Tyr Phe Ala Gln Glu Gly Cys Ser Phe Leu Tyr Glu Lys Leu Pro Pro
            565                 570                 575

Ser Pro Ser Ser Pro Gly Asn Gly Asp Cys Thr Leu Leu Ala Leu Ala
            580                 585                 590

Gln Leu Arg Gly Pro Leu Ser Val Asp Val Pro Leu Val Pro Glu Gly
            595                 600                 605

Leu Leu Thr Pro Glu Ala Ser Pro Val Lys Gln Ser Phe Phe His Tyr
            610                 615                 620

Thr Glu Lys Glu Gln Asn Glu Ile Asp Arg Leu Ile Gln Gln Ile Ser
625                 630                 635                 640

Gln Leu Ala Gln Gly Met Asp Arg Pro Phe Ser Ala Glu Ala Gly Thr
            645                 650                 655

Gly Gly Leu Glu Pro Leu Gly Leu Glu Pro Leu Asn Pro Asn Leu
            660                 665                 670

Ser Leu Ser Gly Ala Gly Pro Pro Val Leu Ser Leu Asp Leu Lys Pro
            675                 680                 685

Trp Lys Cys Gln Glu Leu Asp Phe Leu Val Asp Pro Asp Asn Leu Phe
            690                 695                 700

Leu Glu Glu Thr Pro Val Glu Asp Ile Phe Met Asp Leu Ser Thr Pro
705                 710                 715                 720

Asp Pro Asn Gly Glu Trp Gly Ser Gly Asp Pro Glu Ala Glu Val Pro
            725                 730                 735

Gly Gly Thr Leu Ser Pro Cys Asn Asn Leu Ser Pro Glu Asp His Ser
            740                 745                 750

Phe Leu Glu Asp Leu Ala Thr Tyr Glu Thr Ala Phe Glu Thr Gly Val
```

```
                    755                 760                 765
Ser Thr Phe Pro Tyr Glu Gly Phe Ala Asp Glu Leu His Gln Leu Gln
        770                 775                 780
Ser Gln Val Gln Asp Ser Phe His Glu Asp Gly Ser Gly Gly Glu Pro
785                 790                 795                 800

Thr Phe

<210> SEQ ID NO 4
<211> LENGTH: 3252
<212> TYPE: DNA
<213> ORGANISM: Homo sapiens
<220> FEATURE:
<221> NAME/KEY: CDS
<222> LOCATION: (102)..(2510)

<400> SEQUENCE: 4
tgagcgagag acggggaagc acggaggagg aagccgccgg tgcgtcggga cgggagcgca        60
ggtgctcggg cacccgagct ggagctccgc agccgccggt c atg tac cgc tcc acc      116
                                              Met Tyr Arg Ser Thr
                                               1               5 aag ggc gcc tcc aag gcg cgc cgg gac cag atc aac gcc gag atc cgg        164
Lys Gly Ala Ser Lys Ala Arg Arg Asp Gln Ile Asn Ala Glu Ile Arg
             10                  15                  20 aac ctc aag gag ctg ctg ccg ctg gcc gaa gcg gac aag gtc cgg ctg        212
Asn Leu Lys Glu Leu Leu Pro Leu Ala Glu Ala Asp Lys Val Arg Leu
         25                  30                  35 tcc tac ctg cac atc atg agc ctc gcc tgc atc tac act cgc aag ggc        260
Ser Tyr Leu His Ile Met Ser Leu Ala Cys Ile Tyr Thr Arg Lys Gly
     40                  45                  50 gtc ttc ttc gct ggt ggc act cct ctg gcg ggc ccc acg ggg ctt ctc        308
Val Phe Phe Ala Gly Gly Thr Pro Leu Ala Gly Pro Thr Gly Leu Leu
 55                  60                  65 tca gct caa gag ctt gag gac atc gta gcg gca cta ccc ggc ttt ctg        356
Ser Ala Gln Glu Leu Glu Asp Ile Val Ala Ala Leu Pro Gly Phe Leu
 70                  75                  80                  85 ctt gtg ttc aca gcc gag ggg aaa ttg ctc tac ctg tct gag agt gtg        404
Leu Val Phe Thr Ala Glu Gly Lys Leu Leu Tyr Leu Ser Glu Ser Val
             90                  95                 100 agc gag cat ctg ggc cac tcc atg gtt gac ctg gtt gcc cag ggt gac        452
Ser Glu His Leu Gly His Ser Met Val Asp Leu Val Ala Gln Gly Asp
            105                 110                 115 agc atc tac gac atc att gac cca gct gac cac ctc act gtg cgc cag        500
Ser Ile Tyr Asp Ile Ile Asp Pro Ala Asp His Leu Thr Val Arg Gln
        120                 125                 130 caa ctc acc ctg ccc tct gcc ctg gac act gat cgc ctc ttc cgc tgc        548
Gln Leu Thr Leu Pro Ser Ala Leu Asp Thr Asp Arg Leu Phe Arg Cys
    135                 140                 145 cgc ttc aac acc tcc aag tcc ctc agg cgc cag agt gca ggc aac aaa        596
Arg Phe Asn Thr Ser Lys Ser Leu Arg Arg Gln Ser Ala Gly Asn Lys
150                 155                 160                 165 ctc gtg ctt att cga ggc cga ttc cat gct cac cca cct gga gcc tac        644
Leu Val Leu Ile Arg Gly Arg Phe His Ala His Pro Pro Gly Ala Tyr
                170                 175                 180 tgg gca gga aat ccc gtg ttc aca gct ttc tgt gcc cct ctg gag ccg        692
Trp Ala Gly Asn Pro Val Phe Thr Ala Phe Cys Ala Pro Leu Glu Pro
            185                 190                 195 aga ccc cgc cca ggt cct ggc cct ggc cct ggc cct gcc tcg ctc ttc        740
Arg Pro Arg Pro Gly Pro Gly Pro Gly Pro Gly Pro Ala Ser Leu Phe
        200                 205                 210
```

-continued

| | | |
|---|---|---|
| ctg gcc atg ttc cag agc cgc cat gct aaa gac ctg gct cta ctg gac<br>Leu Ala Met Phe Gln Ser Arg His Ala Lys Asp Leu Ala Leu Leu Asp<br>215                    220                    225 | | 788 |
| atc tcc gag agt gtc cta atc tac ctg ggc ttt gag cgc agt gaa ctg<br>Ile Ser Glu Ser Val Leu Ile Tyr Leu Gly Phe Glu Arg Ser Glu Leu<br>230                    235                    240                    245 | | 836 |
| ctt tgt aaa tca tgg tat gga ctg ctg cac ccc gag gac ctg gcc cac<br>Leu Cys Lys Ser Trp Tyr Gly Leu Leu His Pro Glu Asp Leu Ala His<br>                    250                    255                    260 | | 884 |
| gct tct gct caa cac tac cgc ctg ttg gct gag agt gga gat att cag<br>Ala Ser Ala Gln His Tyr Arg Leu Leu Ala Glu Ser Gly Asp Ile Gln<br>              265                    270                    275 | | 932 |
| gca gag atg gtg gtg agg cta cag gcc aag act gga ggc tgg gca tgg<br>Ala Glu Met Val Val Arg Leu Gln Ala Lys Thr Gly Gly Trp Ala Trp<br>280                    285                    290 | | 980 |
| att tac tgc ctg tta tac tca gaa ggt cca gag gga ccc att act gcc<br>Ile Tyr Cys Leu Leu Tyr Ser Glu Gly Pro Glu Gly Pro Ile Thr Ala<br>295                    300                    305 | | 1028 |
| aat aac tac cca atc agt gac atg gaa gcc tgg agc ctc cgc cag cag<br>Asn Asn Tyr Pro Ile Ser Asp Met Glu Ala Trp Ser Leu Arg Gln Gln<br>310                    315                    320                    325 | | 1076 |
| ttg aac tct gaa gac acc cag gca gct tat gtc ctg ggc act ccg acc<br>Leu Asn Ser Glu Asp Thr Gln Ala Ala Tyr Val Leu Gly Thr Pro Thr<br>                    330                    335                    340 | | 1124 |
| atg ctg ccc tca ttc cct gaa aac att ctt tcc cag gaa gag tgc tcc<br>Met Leu Pro Ser Phe Pro Glu Asn Ile Leu Ser Gln Glu Glu Cys Ser<br>              345                    350                    355 | | 1172 |
| agc act aac cca ctc ttc acc gca gca ctg ggg gct ccc aga agc acc<br>Ser Thr Asn Pro Leu Phe Thr Ala Ala Leu Gly Ala Pro Arg Ser Thr<br>360                    365                    370 | | 1220 |
| agc ttc ccc agt gct cct gaa ctg agt gtt gtc tct gca tca gaa gag<br>Ser Phe Pro Ser Ala Pro Glu Leu Ser Val Val Ser Ala Ser Glu Glu<br>375                    380                    385 | | 1268 |
| ctt ccc cga ccc tcc aaa gaa ctg gac ttc agt tac ctg aca ttc cct<br>Leu Pro Arg Pro Ser Lys Glu Leu Asp Phe Ser Tyr Leu Thr Phe Pro<br>390                    395                    400                    405 | | 1316 |
| tct ggg cct gag cct tct ctc caa gca gaa cta agc aag gat ctt gtg<br>Ser Gly Pro Glu Pro Ser Leu Gln Ala Glu Leu Ser Lys Asp Leu Val<br>                    410                    415                    420 | | 1364 |
| tgc act cca cct tac acg ccc cat cag cca gga ggc tgt gcc ttc ctc<br>Cys Thr Pro Pro Tyr Thr Pro His Gln Pro Gly Gly Cys Ala Phe Leu<br>              425                    430                    435 | | 1412 |
| ttc agc ctc cat gag ccc ttc cag acc cat ttg ccc acc cca tcc agc<br>Phe Ser Leu His Glu Pro Phe Gln Thr His Leu Pro Thr Pro Ser Ser<br>440                    445                    450 | | 1460 |
| act ctt caa gaa cag ctg act cca agc act gcg acc ttc tct gat cag<br>Thr Leu Gln Glu Gln Leu Thr Pro Ser Thr Ala Thr Phe Ser Asp Gln<br>455                    460                    465 | | 1508 |
| ttg acg ccc agc agt gca acc ttc cca gat cca cta act agc cca ctg<br>Leu Thr Pro Ser Ser Ala Thr Phe Pro Asp Pro Leu Thr Ser Pro Leu<br>470                    475                    480                    485 | | 1556 |
| caa ggc cag ttg act gaa acc tcg gtc aga agc tat gaa gac cag ttg<br>Gln Gly Gln Leu Thr Glu Thr Ser Val Arg Ser Tyr Glu Asp Gln Leu<br>                    490                    495                    500 | | 1604 |
| act ccc tgc acc tcc acc ttc cca gac cag ctg ctt ccc agc aca gcc<br>Thr Pro Cys Thr Ser Thr Phe Pro Asp Gln Leu Leu Pro Ser Thr Ala<br>              505                    510                    515 | | 1652 |
| acc ttc cca gag cct ctg ggc agc cct gcc cat gaa cag ctg act cct<br>Thr Phe Pro Glu Pro Leu Gly Ser Pro Ala His Glu Gln Leu Thr Pro<br>520                    525                    530 | | 1700 |

```
ccc agc aca gca ttc caa gca cac ctg gac agc ccc agc caa acc ttc    1748
Pro Ser Thr Ala Phe Gln Ala His Leu Asp Ser Pro Ser Gln Thr Phe
    535                 540                 545 cca gag caa ctg agc ccc aac cct acc aag act tac ttt gcc cag gag    1796
Pro Glu Gln Leu Ser Pro Asn Pro Thr Lys Thr Tyr Phe Ala Gln Glu
550                 555                 560                 565 gga tgc agt ttt ctc tat gag aag ttg ccc cca agt cct agc agc cct    1844
Gly Cys Ser Phe Leu Tyr Glu Lys Leu Pro Pro Ser Pro Ser Ser Pro
                570                 575                 580 ggt aat ggg gac tgc acg ctc ttg gcc cta gcc cag ctc cgg ggc ccc    1892
Gly Asn Gly Asp Cys Thr Leu Leu Ala Leu Ala Gln Leu Arg Gly Pro
            585                 590                 595 ctc tct gtg gat gtc ccc ctg gtg ccc gaa ggc ctg ctc aca cct gag    1940
Leu Ser Val Asp Val Pro Leu Val Pro Glu Gly Leu Leu Thr Pro Glu
        600                 605                 610 gcc tct cca gtc aag cag agt ttc ttc cac tac tct gaa aag gag cag    1988
Ala Ser Pro Val Lys Gln Ser Phe Phe His Tyr Ser Glu Lys Glu Gln
    615                 620                 625 aat gag ata gac cgt ctc atc cag cag att agc caa ttg gct cag ggc    2036
Asn Glu Ile Asp Arg Leu Ile Gln Gln Ile Ser Gln Leu Ala Gln Gly
630                 635                 640                 645 atg gac aga ccc ttc tca gct gag gct ggc act ggc gga cta gag cca    2084
Met Asp Arg Pro Phe Ser Ala Glu Ala Gly Thr Gly Gly Leu Glu Pro
                650                 655                 660 ctt gga gga ctg gag ccc ctg gac tcc aac ctg tcc ctg tca ggg gca    2132
Leu Gly Gly Leu Glu Pro Leu Asp Ser Asn Leu Ser Leu Ser Gly Ala
            665                 670                 675 ggc ccc cct gtg ctc agc ctg gac ctg aaa ccc tgg aaa tgc agg gag    2180
Gly Pro Pro Val Leu Ser Leu Asp Leu Lys Pro Trp Lys Cys Gln Glu
        680                 685                 690 ctg gac ttc ctg gct gac cct gat aac atg ttc ctg gaa gag acg ccc    2228
Leu Asp Phe Leu Ala Asp Pro Asp Asn Met Phe Leu Glu Glu Thr Pro
    695                 700                 705 gtg gaa gac atc ttc atg gat ctc tct acc cca gat ccc agt gag gaa    2276
Val Glu Asp Ile Phe Met Asp Leu Ser Thr Pro Asp Pro Ser Glu Glu
710                 715                 720                 725 tgg ggc tca ggg gat cct gag gca gag ggc cca gga ggg gcc cca tcg    2324
Trp Gly Ser Gly Asp Pro Glu Ala Glu Gly Pro Gly Gly Ala Pro Ser
                730                 735                 740 cct tgc aac aac ctg tcc cca gaa gac cac agc ttc ctg gag gac ctg    2372
Pro Cys Asn Asn Leu Ser Pro Glu Asp His Ser Phe Leu Glu Asp Leu
            745                 750                 755 gcc aca tat gaa acc gcc ttt gag aca ggt gtc tca gca ttc ccc tat    2420
Ala Thr Tyr Glu Thr Ala Phe Glu Thr Gly Val Ser Ala Phe Pro Tyr
        760                 765                 770 gat ggg ttt act gat gag ttg cat caa ctc cag agc caa gtt caa gac    2468
Asp Gly Phe Thr Asp Glu Leu His Gln Leu Gln Ser Gln Val Gln Asp
    775                 780                 785 agc ttc cat gaa gat gga agt gga ggg gaa cca acg ttt tga            2510
Ser Phe His Glu Asp Gly Ser Gly Gly Glu Pro Thr Phe
790                 795                 800 ataagtctgt gacttaacgt cgtcaagtat ggcatattgt catcaagacg tggagccgct    2570
ctccaccccc ccgggactgt tgggggggatt ctgagggcca gagggggata tatatgattc   2630
```

ccaggcccc gcaggatttt ggggggggggg aggtgggagg gcaagggagg ggagcttctt    2690
tttaaaatca agagacttcg agcgatccca gtttccattt caatctgtat tcactcgtag    2750
tgagtttcct tgaatgggat ttcaagcgga gaatggggga gtctcacttc cccgccgcct    2810

```
tgccccattg gcctgggcca gttctccact cctaggggcc aagccacccc tagccttggt      2870
gggggaaagg cagggcccac ccgggccagc ccgtgccctg aggggctctt gacacccacg      2930
tagaattctc tacacaccag taacgggatt tcaattccga tggactctgc cgccctggcg      2990
gcccttcctg tgacttttgc gccccgcgcc tggggtgggg ggtgcgaaaa aacgctacgt      3050
tcctttccga tggaggaagg cagacctgcc gtcacacgtg tgcttgcacg agtgcgtgta      3110
cctggtgcgg gactcacccg gccgccagac tgcctgggcc tgcccaaatg ccacctcgg       3170 tggtgctgcg gtgactttgt agccaacttt ataataaagt ccagtttgcc ttttggtaa       3230 aaaaaaaaaa aaaaaaaaaa aa                                              3252

<210> SEQ ID NO 5
<211> LENGTH: 3087
<212> TYPE: DNA
<213> ORGANISM: Mus musculus
<220> FEATURE:
<221> NAME/KEY: CDS
<222> LOCATION: (51)..(2459)

<400> SEQUENCE: 5
aggatcgcag gtgctcggga gccggagctg gagctccaca gccggcagtc atg tac          56
                                                       Met Tyr
                                                         1 cga tcc acc aag ggc gcc tcc aag gcg cgc cgc gac cag atc aac gcc         104
Arg Ser Thr Lys Gly Ala Ser Lys Ala Arg Arg Asp Gln Ile Asn Ala
              5                  10                  15 gag att cgg aac ctc aag gag ctg ctg ccg ttg gct gaa gcg gac aag         152
Glu Ile Arg Asn Leu Lys Glu Leu Leu Pro Leu Ala Glu Ala Asp Lys
         20                  25                  30 gtc cgg ctg tcc tac ctg cac atc atg agt ctt gcc tgc atc tac act         200
Val Arg Leu Ser Tyr Leu His Ile Met Ser Leu Ala Cys Ile Tyr Thr
 35                  40                  45                  50 cgc aag ggt gtc ttc ttt gct gga ggc act cct ttg gct ggc ccc acc         248
Arg Lys Gly Val Phe Phe Ala Gly Gly Thr Pro Leu Ala Gly Pro Thr
                 55                  60                  65 ggg ctt ctc tct gct caa gag ctt gaa gac att gtg gca gca cta cct         296
Gly Leu Leu Ser Ala Gln Glu Leu Glu Asp Ile Val Ala Ala Leu Pro
             70                  75                  80 gga ttt ctc ctt gta ttc aca gct gag ggg aag ttg cta tac ctg tcg         344
Gly Phe Leu Leu Val Phe Thr Ala Glu Gly Lys Leu Leu Tyr Leu Ser
         85                  90                  95 gag agt gtg agc gag cat ctg ggc cac tct atg gtg gac ctg gtt gcc         392
Glu Ser Val Ser Glu His Leu Gly His Ser Met Val Asp Leu Val Ala
    100                 105                 110 cag ggc gac agt atc tac gat atc att gac cct gct gac cat ctc act         440
Gln Gly Asp Ser Ile Tyr Asp Ile Ile Asp Pro Ala Asp His Leu Thr
115                 120                 125                 130 gtg cgc cag cag ctc acc atg ccc tct gct ctg gat gct gat cgc ctt         488
Val Arg Gln Gln Leu Thr Met Pro Ser Ala Leu Asp Ala Asp Arg Leu
                135                 140                 145 ttc cgt tgt cga ttc aac acc tcc aag tcc ctc cgg cgc cag agt tca         536
Phe Arg Cys Arg Phe Asn Thr Ser Lys Ser Leu Arg Arg Gln Ser Ser
            150                 155                 160 gga aac aaa ctg gtg ctt att cga ggt cga ttc cat gct cac cca cct         584
Gly Asn Lys Leu Val Leu Ile Arg Gly Arg Phe His Ala His Pro Pro
        165                 170                 175 ggg gcc tac tgg gca gga aac cct gtg ttc acc gct ttc tgc gcc cca         632
Gly Ala Tyr Trp Ala Gly Asn Pro Val Phe Thr Ala Phe Cys Ala Pro
    180                 185                 190
```

-continued

| | | |
|---|---|---|
| ctg gag cca aga ccc cgc cct ggc ccc ggc cct ggc cct ggt<br>Leu Glu Pro Arg Pro Arg Pro Gly Pro Gly Pro Gly Pro Gly<br>195                       200                        205                        210 | 680 |
| cct gct tct ctc ttc ctg gcc atg ttc cag agc cgg cat gct aag gac<br>Pro Ala Ser Leu Phe Leu Ala Met Phe Gln Ser Arg His Ala Lys Asp<br>                              215                        220                        225 | 728 |
| cta gcc cta ctg gac gtt tct gaa agt gtc cta atc tac ctg ggc ttt<br>Leu Ala Leu Leu Asp Val Ser Glu Ser Val Leu Ile Tyr Leu Gly Phe<br>                230                        235                        240 | 776 |
| gag cgc agc gaa ctg ctc tgt aaa tca tgg tat gga ctg cta cac ccc<br>Glu Arg Ser Glu Leu Leu Cys Lys Ser Trp Tyr Gly Leu Leu His Pro<br>              245                        250                        255 | 824 |
| gag gac ctg gcc caa gct tct tct caa cac tac cgc ctg ttg gct gaa<br>Glu Asp Leu Ala Gln Ala Ser Ser Gln His Tyr Arg Leu Leu Ala Glu<br>260                        265                        270 | 872 |
| agt gga gat att cag gct gaa atg gtg gtg aga ctt caa gcc aag cat<br>Ser Gly Asp Ile Gln Ala Glu Met Val Val Arg Leu Gln Ala Lys His<br>275                        280                        285                        290 | 920 |
| gga ggc tgg aca tgg att tac tgc atg cta tac tca gaa ggt cca gaa<br>Gly Gly Trp Thr Trp Ile Tyr Cys Met Leu Tyr Ser Glu Gly Pro Glu<br>                              295                        300                        305 | 968 |
| ggc cct ttt act gcc aat aac tac cct atc agt gac acg gaa gcc tgg<br>Gly Pro Phe Thr Ala Asn Asn Tyr Pro Ile Ser Asp Thr Glu Ala Trp<br>                            310                        315                        320 | 1016 |
| agc ctc cgc cag cag cta aac tct gaa gac acc cag gca gcc tat gtc<br>Ser Leu Arg Gln Gln Leu Asn Ser Glu Asp Thr Gln Ala Ala Tyr Val<br>                            325                        330                        335 | 1064 |
| cta gga acc cca gct gtg cta ccc tca ttc tct gag aat gtc ttc tcc<br>Leu Gly Thr Pro Ala Val Leu Pro Ser Phe Ser Glu Asn Val Phe Ser<br>340                        345                        350 | 1112 |
| cag gag caa tgc tct aat cca ctc ttt aca cca tcc ctg ggg act cct<br>Gln Glu Gln Cys Ser Asn Pro Leu Phe Thr Pro Ser Leu Gly Thr Pro<br>355                        360                        365                        370 | 1160 |
| aga agt gcc agc ttc ccc agg gct cct gaa cta ggt gtg atc tca aca<br>Arg Ser Ala Ser Phe Pro Arg Ala Pro Glu Leu Gly Val Ile Ser Thr<br>                            375                        380                        385 | 1208 |
| cca gaa gag ctt ccc caa ccc tcc aaa gag ctg gac ttc agt tac ctg<br>Pro Glu Glu Leu Pro Gln Pro Ser Lys Glu Leu Asp Phe Ser Tyr Leu<br>                            390                        395                        400 | 1256 |
| cca ttc cct gct agg cct gag cct tcc ctc caa gca gac ctg agc aag<br>Pro Phe Pro Ala Arg Pro Glu Pro Ser Leu Gln Ala Asp Leu Ser Lys<br>                            405                        410                        415 | 1304 |
| gat ttg gtg tgt act cca cct tac aca ccc cac cag cca gga ggc tgt<br>Asp Leu Val Cys Thr Pro Pro Tyr Thr Pro His Gln Pro Gly Gly Cys<br>420                        425                        430 | 1352 |
| gcc ttc ctc ttc agc ctc cat gaa ccc ttc cag act cac ttg ccc cct<br>Ala Phe Leu Phe Ser Leu His Glu Pro Phe Gln Thr His Leu Pro Pro<br>435                        440                        445                        450 | 1400 |
| ccg tcc agc tct ctc caa gaa cag ctg aca cca agt aca gtg act ttc<br>Pro Ser Ser Ser Leu Gln Glu Gln Leu Thr Pro Ser Thr Val Thr Phe<br>                            455                        460                        465 | 1448 |
| tct gaa cag ttg aca ccc agc agt gct acc ttc cca gac cca cta acc<br>Ser Glu Gln Leu Thr Pro Ser Ser Ala Thr Phe Pro Asp Pro Leu Thr<br>470                        475                        480 | 1496 |
| agt tca cta caa gga cag ttg aca gaa agc tca gcc aga agc ttt gaa<br>Ser Ser Leu Gln Gly Gln Leu Thr Glu Ser Ser Ala Arg Ser Phe Glu<br>485                        490                        495 | 1544 |
| gac cag ttg act cca tgc acc tct tcc ttc cct gac cag cta ctt ccc<br>Asp Gln Leu Thr Pro Cys Thr Ser Ser Phe Pro Asp Gln Leu Leu Pro<br>500                        505                        510 | 1592 |

```
agc act gcc aca ttc cca gag cct ctg ggc agc ccc gcc cat gag cag    1640
Ser Thr Ala Thr Phe Pro Glu Pro Leu Gly Ser Pro Ala His Glu Gln
515                 520                 525                 530 ctg act cct ccc agc aca gca ttc cag gct cat ctg aac agc ccc agc    1688
Leu Thr Pro Pro Ser Thr Ala Phe Gln Ala His Leu Asn Ser Pro Ser
                535                 540                 545 caa acc ttc cca gag caa ctg agc ccc aat cct acc aag act tac ttc    1736
Gln Thr Phe Pro Glu Gln Leu Ser Pro Asn Pro Thr Lys Thr Tyr Phe
            550                 555                 560 gcc cag gag gga tgc agt ttt ctc tat gag aag ttg ccc cca agt cct    1784
Ala Gln Glu Gly Cys Ser Phe Leu Tyr Glu Lys Leu Pro Pro Ser Pro
        565                 570                 575 agc agc cct ggt aat ggg gac tgt aca ctc ctg gcc cta gct cag ctc    1832
Ser Ser Pro Gly Asn Gly Asp Cys Thr Leu Leu Ala Leu Ala Gln Leu
    580                 585                 590 cgg ggc ccc ctc tct gtg gat gtc ccc ctg gtg ccc gaa ggc ctg ctc    1880
Arg Gly Pro Leu Ser Val Asp Val Pro Leu Val Pro Glu Gly Leu Leu
595                 600                 605                 610 aca cct gag gcc tct cca gtc aag caa agt ttc ttc cac tac aca gag    1928
Thr Pro Glu Ala Ser Pro Val Lys Gln Ser Phe Phe His Tyr Thr Glu
                615                 620                 625 aaa gag caa aat gag ata gat cgt ctc att cag cag atc agc cag ttg    1976
Lys Glu Gln Asn Glu Ile Asp Arg Leu Ile Gln Gln Ile Ser Gln Leu
            630                 635                 640 gct cag ggc gtg gac agg ccc ttc tca gct gag gct ggc act ggg ggg    2024
Ala Gln Gly Val Asp Arg Pro Phe Ser Ala Glu Ala Gly Thr Gly Gly
        645                 650                 655 ctg gag cca ctt gga ggg ctg gag ccc ctg aac cct aac ctg tcc ctg    2072
Leu Glu Pro Leu Gly Gly Leu Glu Pro Leu Asn Pro Asn Leu Ser Leu
    660                 665                 670 tca ggg gct gga ccc cct gtg ctt agc ctg gat ctt aaa ccc tgg aaa    2120
Ser Gly Ala Gly Pro Pro Val Leu Ser Leu Asp Leu Lys Pro Trp Lys
675                 680                 685                 690 tgc cag gag ctg gac ttc ctg gtt gac cct gat aat tta ttc ctg gaa    2168
Cys Gln Glu Leu Asp Phe Leu Val Asp Pro Asp Asn Leu Phe Leu Glu
                695                 700                 705 gag acg cca gtg gaa gac atc ttc atg gat ctt tct act cca gac ccc    2216
Glu Thr Pro Val Glu Asp Ile Phe Met Asp Leu Ser Thr Pro Asp Pro
            710                 715                 720 aat ggg gaa tgg ggt tca ggg gat cct gag gca gag gtc cca gga ggg    2264
Asn Gly Glu Trp Gly Ser Gly Asp Pro Glu Ala Glu Val Pro Gly Gly
        725                 730                 735 acc ctg tca cct tgc aac aac ctg tcc cca gaa gat cac agc ttc ctg    2312
Thr Leu Ser Pro Cys Asn Asn Leu Ser Pro Glu Asp His Ser Phe Leu
    740                 745                 750 gag gac ttg gcc acc tat gaa acc gcc ttt gag aca ggt gtc tca aca    2360
Glu Asp Leu Ala Thr Tyr Glu Thr Ala Phe Glu Thr Gly Val Ser Thr
755                 760                 765                 770 ttc ccc tac gaa ggg ttt gct gat gag ttg cat caa ctc cag agc caa    2408
Phe Pro Tyr Glu Gly Phe Ala Asp Glu Leu His Gln Leu Gln Ser Gln
                775                 780                 785 gtt caa gac agc ttc cat gaa gat gga agt gga ggg gaa cca acg ttt    2456
Val Gln Asp Ser Phe His Glu Asp Gly Ser Gly Gly Glu Pro Thr Phe
            790                 795                 800 tga ataagtctgt gacttaacgt cttcaagtat ggcatattgt catcaagacg         2509
tggagccgct ctccaccccc ccgggactgt tgggggggatt ctgggggcca gagggggata  2569
tatctgattc tccaggccct gaaggattta gggggaggt gggagggtaa gggagggag    2629
```

```
caacttttta aaatcaagag acttcgagcg atcccagttt ccatttcaat ctgtattcac    2689
tcgtagtgag tttccttgaa tggatttcaa gcggagaatg ggggagtctc acttcctcac    2749
cgcgctgccc catgggcctg gccagttct ccactcctag gggcaaagcc acccctgggc     2809
tttggtgggg gaaaggcatg gcccacctgg ggctagcctg tgccccgagg ggctcttgac    2869
acccacgtag aattctctac aaaccagtaa cgggatttca attccgacgg actctgccgc    2929
cctggcggct cttcctgtga cttttgcgcc ccgcgcctgg ggtgggggc gcgaagagac     2989 gctacattcc tttccgatgg aggaaggcag atctgccgtc acacgtgtgc ttgcacgagt    3049
gcgtgtacct ggtgcgggac tcacccggcc gccagacc                            3087

<210> SEQ ID NO 6
<211> LENGTH: 2459
<212> TYPE: DNA
<213> ORGANISM: Rattus norvegicus
<220> FEATURE:
<221> NAME/KEY: CDS
<222> LOCATION: (35)..(2443)

<400> SEQUENCE: 6
gggagccgga gctggagctc cacggccggc agtc atg tac cga tcc acc aag ggc    55
                                     Met Tyr Arg Ser Thr Lys Gly
                                      1               5 gcc tcc aag gcg cgc cgc gac cag atc aac gcc gag att cgg aac ctc    103
Ala Ser Lys Ala Arg Arg Asp Gln Ile Asn Ala Glu Ile Arg Asn Leu
         10                  15                  20 aag gaa ctg ctg ccg ttg gct gaa gcg gac aag gtc cgg ctg tcc tac    151
Lys Glu Leu Leu Pro Leu Ala Glu Ala Asp Lys Val Arg Leu Ser Tyr
     25                  30                  35 ctg cac atc atg agt ctt gcc tgc atc tac act cgc aag ggt gtc ttc    199
Leu His Ile Met Ser Leu Ala Cys Ile Tyr Thr Arg Lys Gly Val Phe
 40                  45                  50                  55 ttt gct gga ggc act cct ttg gct ggc ccc acg ggg ctt ctc tct gct    247
Phe Ala Gly Gly Thr Pro Leu Ala Gly Pro Thr Gly Leu Leu Ser Ala
                 60                  65                  70 caa gag ctt gaa gac ata gtg gca gca cta cct gga ttt cta ctt gtg    295
Gln Glu Leu Glu Asp Ile Val Ala Ala Leu Pro Gly Phe Leu Leu Val
             75                  80                  85 ttc aca gct gag ggg aag ttg cta tac ctg tcg gag agt gtg agc gag    343
Phe Thr Ala Glu Gly Lys Leu Leu Tyr Leu Ser Glu Ser Val Ser Glu
         90                  95                 100 cat ctg ggc cat tct atg gtg gat ctg gtt gcc cag ggt gac agt att    391
His Leu Gly His Ser Met Val Asp Leu Val Ala Gln Gly Asp Ser Ile
    105                 110                 115 tac gac atc att gac cct gct gac cat ctc act gtg cgc cag cag ctc    439
Tyr Asp Ile Ile Asp Pro Ala Asp His Leu Thr Val Arg Gln Gln Leu
120                 125                 130                 135 acc atg ccc tct gct ctg gat gct gat cgc ctt ttc cgt tgt cga ttt    487
Thr Met Pro Ser Ala Leu Asp Ala Asp Arg Leu Phe Arg Cys Arg Phe
                140                 145                 150 aac aca tcc aag tcc ctc cgg cgc cag agt gca ggc aac aaa ctg gtg    535
Asn Thr Ser Lys Ser Leu Arg Arg Gln Ser Ala Gly Asn Lys Leu Val
            155                 160                 165 ctt att cga ggt cga ttc cat gct cac cca cct ggg gcc tac tgg gca    583
Leu Ile Arg Gly Arg Phe His Ala His Pro Pro Gly Ala Tyr Trp Ala
        170                 175                 180 gga aac ccc gtg ttc aca gct ttc tgt gcc cca ctg gag cca aga ccc    631
Gly Asn Pro Val Phe Thr Ala Phe Cys Ala Pro Leu Glu Pro Arg Pro
    185                 190                 195
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cgt | ccc | ggc | cct | ggc | cct | ggc | cct | ggc | cct | ggt | cct | gcc | tct | ctc | ttc | 679  |
| Arg | Pro | Gly | Pro | Gly | Pro | Gly | Pro | Gly | Pro | Gly | Pro | Ala | Ser | Leu | Phe |      |
| 200 |     |     |     | 205 |     |     |     | 210 |     |     |     |     | 215 |     |     |      |
| ctg | gcc | atg | ttc | cag | agc | cgg | cat | gct | aag | gac | cta | gcc | cta | ctg | gac | 727  |
| Leu | Ala | Met | Phe | Gln | Ser | Arg | His | Ala | Lys | Asp | Leu | Ala | Leu | Leu | Asp |      |
|     |     |     |     | 220 |     |     |     |     | 225 |     |     |     |     | 230 |     |      |
| att | tct | gaa | agt | gtc | cta | atc | tac | ctg | ggc | ttt | gag | cgc | agc | gaa | ctg | 775  |
| Ile | Ser | Glu | Ser | Val | Leu | Ile | Tyr | Leu | Gly | Phe | Glu | Arg | Ser | Glu | Leu |      |
|     |     |     | 235 |     |     |     |     | 240 |     |     |     |     | 245 |     |     |      |
| ctc | tgt | aaa | tca | tgg | tat | gga | ctg | cta | cac | ccc | gag | gac | ctg | gcc | cac | 823  |
| Leu | Cys | Lys | Ser | Trp | Tyr | Gly | Leu | Leu | His | Pro | Glu | Asp | Leu | Ala | His |      |
|     |     | 250 |     |     |     |     | 255 |     |     |     |     | 260 |     |     |     |      |
| gct | tct | tct | caa | cac | tac | cgc | ctg | ttg | gct | gaa | aat | gga | gat | att | cag | 871  |
| Ala | Ser | Ser | Gln | His | Tyr | Arg | Leu | Leu | Ala | Glu | Asn | Gly | Asp | Ile | Gln |      |
|     | 265 |     |     |     |     | 270 |     |     |     |     | 275 |     |     |     |     |      |
| gct | gaa | atg | gtg | gtg | aga | ctt | caa | gcc | aag | cat | gga | ggc | tgg | aca | tgg | 919  |
| Ala | Glu | Met | Val | Val | Arg | Leu | Gln | Ala | Lys | His | Gly | Gly | Trp | Thr | Trp |      |
| 280 |     |     |     |     | 285 |     |     |     |     | 290 |     |     |     |     | 295 |      |
| att | tac | tgc | atg | cta | tac | tcg | gat | ggt | cca | gaa | ggc | cct | att | act | gcc | 967  |
| Ile | Tyr | Cys | Met | Leu | Tyr | Ser | Asp | Gly | Pro | Glu | Gly | Pro | Ile | Thr | Ala |      |
|     |     |     |     |     | 300 |     |     |     |     | 305 |     |     |     |     | 310 |      |
| aat | aac | tac | cct | atc | agt | gac | acg | gaa | gcc | tgg | agt | ctt | cgc | cag | cag | 1015 |
| Asn | Asn | Tyr | Pro | Ile | Ser | Asp | Thr | Glu | Ala | Trp | Ser | Leu | Arg | Gln | Gln |      |
|     |     |     |     | 315 |     |     |     |     | 320 |     |     |     |     | 325 |     |      |
| cta | aac | tct | gaa | aac | acc | cag | gca | gcc | tat | gtc | cta | gga | acc | cca | gct | 1063 |
| Leu | Asn | Ser | Glu | Asn | Thr | Gln | Ala | Ala | Tyr | Val | Leu | Gly | Thr | Pro | Ala |      |
|     |     |     | 330 |     |     |     |     | 335 |     |     |     |     | 340 |     |     |      |
| gtg | cta | ccc | tca | ttc | tct | gag | aat | gtc | ttc | tcc | cag | gag | cac | tgc | tct | 1111 |
| Val | Leu | Pro | Ser | Phe | Ser | Glu | Asn | Val | Phe | Ser | Gln | Glu | His | Cys | Ser |      |
|     | 345 |     |     |     |     | 350 |     |     |     |     | 355 |     |     |     |     |      |
| aat | cca | ctc | ttt | aca | cca | gcc | ctg | ggg | act | cct | aga | agt | gcc | agc | ttc | 1159 |
| Asn | Pro | Leu | Phe | Thr | Pro | Ala | Leu | Gly | Thr | Pro | Arg | Ser | Ala | Ser | Phe |      |
| 360 |     |     |     |     | 365 |     |     |     |     | 370 |     |     |     |     | 375 |      |
| ccc | agg | gcc | cct | gaa | cta | ggt | gtg | atc | tca | aca | tca | gaa | gag | ctt | gcc | 1207 |
| Pro | Arg | Ala | Pro | Glu | Leu | Gly | Val | Ile | Ser | Thr | Ser | Glu | Glu | Leu | Ala |      |
|     |     |     |     | 380 |     |     |     |     | 385 |     |     |     |     | 390 |     |      |
| caa | ccc | tcc | aaa | gaa | ctg | gac | ttc | agt | tac | ctg | cca | ttc | cct | gca | agg | 1255 |
| Gln | Pro | Ser | Lys | Glu | Leu | Asp | Phe | Ser | Tyr | Leu | Pro | Phe | Pro | Ala | Arg |      |
|     |     |     | 395 |     |     |     |     | 400 |     |     |     |     | 405 |     |     |      |
| cct | gag | cct | tcc | ctc | caa | gca | gac | ttg | agc | aag | gat | ttg | gtg | tgt | act | 1303 |
| Pro | Glu | Pro | Ser | Leu | Gln | Ala | Asp | Leu | Ser | Lys | Asp | Leu | Val | Cys | Thr |      |
|     |     | 410 |     |     |     |     | 415 |     |     |     |     | 420 |     |     |     |      |
| cca | cct | tac | aca | ccc | cac | cag | cca | gga | ggc | tgc | gcc | ttc | ctc | ttc | agc | 1351 |
| Pro | Pro | Tyr | Thr | Pro | His | Gln | Pro | Gly | Gly | Cys | Ala | Phe | Leu | Phe | Ser |      |
|     | 425 |     |     |     |     | 430 |     |     |     |     | 435 |     |     |     |     |      |
| ctc | cat | gaa | ccc | ttc | cag | act | cac | ttg | ccc | cct | cca | tcc | agc | tct | ctc | 1399 |
| Leu | His | Glu | Pro | Phe | Gln | Thr | His | Leu | Pro | Pro | Pro | Ser | Ser | Ser | Leu |      |
| 440 |     |     |     |     | 445 |     |     |     |     | 450 |     |     |     |     | 455 |      |
| caa | gaa | cag | ctg | acg | cca | agc | acg | gtg | act | ttc | tct | gaa | cag | ttg | aca | 1447 |
| Gln | Glu | Gln | Leu | Thr | Pro | Ser | Thr | Val | Thr | Phe | Ser | Glu | Gln | Leu | Thr |      |
|     |     |     |     | 460 |     |     |     |     | 465 |     |     |     |     | 470 |     |      |
| cca | agc | agt | gca | acc | ttc | cca | gat | cca | cta | acc | agt | tca | cta | caa | gga | 1495 |
| Pro | Ser | Ser | Ala | Thr | Phe | Pro | Asp | Pro | Leu | Thr | Ser | Ser | Leu | Gln | Gly |      |
|     |     |     | 475 |     |     |     |     | 480 |     |     |     |     | 485 |     |     |      |
| cag | ttg | act | gaa | agc | tca | gcc | aga | agc | ttt | gaa | gaa | caa | ttg | act | ccg | 1543 |
| Gln | Leu | Thr | Glu | Ser | Ser | Ala | Arg | Ser | Phe | Glu | Glu | Gln | Leu | Thr | Pro |      |
|     |     | 490 |     |     |     |     | 495 |     |     |     |     | 500 |     |     |     |      |
| tgc | acc | tct | acc | ttc | cct | gac | cag | ctg | ctt | ccc | agc | act | gcc | acg | ttc | 1591 |
| Cys | Thr | Ser | Thr | Phe | Pro | Asp | Gln | Leu | Leu | Pro | Ser | Thr | Ala | Thr | Phe |      |
|     | 505 |     |     |     |     | 510 |     |     |     |     | 515 |     |     |     |     |      |

```
cca gaa cct ctg ggt agc ccc acc cat gag cag ctg act cct ccc agc      1639
Pro Glu Pro Leu Gly Ser Pro Thr His Glu Gln Leu Thr Pro Pro Ser
520                 525                 530                 535 aca gca ttc caa gca cat ctg aac agt cct agc caa acc ttc cca gag      1687
Thr Ala Phe Gln Ala His Leu Asn Ser Pro Ser Gln Thr Phe Pro Glu
            540                 545                 550 caa ctg agc cct aat cct acc aag act tac ttc gcc cag gag gga tgc      1735
Gln Leu Ser Pro Asn Pro Thr Lys Thr Tyr Phe Ala Gln Glu Gly Cys
        555                 560                 565 agt ttt ctc tat gag aag ttg ccc cca agt cct agc agc cct ggt aat      1783
Ser Phe Leu Tyr Glu Lys Leu Pro Pro Ser Pro Ser Ser Pro Gly Asn
    570                 575                 580 ggg gac tgt aca ctc ttg gcc cta gct caa ctc cgg ggt ccc ctc tct      1831
Gly Asp Cys Thr Leu Leu Ala Leu Ala Gln Leu Arg Gly Pro Leu Ser
585                 590                 595 gtg gac gtc ccc ctg gtg cct gaa ggc ctg ctc aca cct gag gcc tct      1879
Val Asp Val Pro Leu Val Pro Glu Gly Leu Leu Thr Pro Glu Ala Ser
600                 605                 610                 615 cca gtc aag caa agt ttc ttc cac tat aca gag aaa gag cag aat gag      1927
Pro Val Lys Gln Ser Phe Phe His Tyr Thr Glu Lys Glu Gln Asn Glu
            620                 625                 630 ata gat cgt ctc atc cag cag atc agc cag ttg gct cag ggc atg gac      1975
Ile Asp Arg Leu Ile Gln Gln Ile Ser Gln Leu Ala Gln Gly Met Asp
        635                 640                 645 agg ccc ttc tca gct gag gct ggc act ggg ggg ctg gag cca ctt gga      2023
Arg Pro Phe Ser Ala Glu Ala Gly Thr Gly Gly Leu Glu Pro Leu Gly
    650                 655                 660 ggg ctg gag ccc ctg aac ccc aac ctg tcc ctg tca ggg gct gga ccc      2071
Gly Leu Glu Pro Leu Asn Pro Asn Leu Ser Leu Ser Gly Ala Gly Pro
665                 670                 675 cct gtg ctt agc ctg gat ctt aaa ccc tgg aaa tgc agg gag ctg gac      2119
Pro Val Leu Ser Leu Asp Leu Lys Pro Trp Lys Cys Arg Glu Leu Asp
680                 685                 690                 695 ttc ttg gtt gac cct gat aat tta ttc ctg gaa gag acg cca gtg gaa      2167
Phe Leu Val Asp Pro Asp Asn Leu Phe Leu Glu Glu Thr Pro Val Glu
            700                 705                 710 gac atc ttc atg gat ctt tct act cca gac ccc aat ggg gaa tgg ggt      2215
Asp Ile Phe Met Asp Leu Ser Thr Pro Asp Pro Asn Gly Glu Trp Gly
        715                 720                 725 tca ggg gat cct gag gca gag gtc cca gga ggg acc ctg tca cct tgc      2263
Ser Gly Asp Pro Glu Ala Glu Val Pro Gly Gly Thr Leu Ser Pro Cys
    730                 735                 740 aac aac ctg tcc cca gaa gat cac agc ttc ctg gag gac ttg gcc acc      2311
Asn Asn Leu Ser Pro Glu Asp His Ser Phe Leu Glu Asp Leu Ala Thr
745                 750                 755 tat gaa acc gcc ttt gag aca ggt gtc tca aca ttc ccc tat gaa ggg      2359
Tyr Glu Thr Ala Phe Glu Thr Gly Val Ser Thr Phe Pro Tyr Glu Gly
760                 765                 770                 775 ttt gct gat gag ttg cat caa ctc cag agc caa gtt caa gac agc ttc      2407
Phe Ala Asp Glu Leu His Gln Leu Gln Ser Gln Val Gln Asp Ser Phe
            780                 785                 790 cat gaa gat gga agt gga ggg gaa cca acg ttt tga ataagtctgt gactta   2459
His Glu Asp Gly Ser Gly Gly Glu Pro Thr Phe
        795                 800

<210> SEQ ID NO 7
<211> LENGTH: 35
<212> TYPE: DNA
<213> ORGANISM: Artificial Sequence
<220> FEATURE:
```

```
<223> OTHER INFORMATION: Synthetic PCR primer

<400> SEQUENCE: 7
aagcacggag gaggaagccg ccggtgcgtc gggac                          35

<210> SEQ ID NO 8
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 8
acgggagcgc aggtgctcgg gcacccgagc tggag                          35

<210> SEQ ID NO 9
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 9
ggagagcggc tccacgtctt gatgacaata tgcca                          35

<210> SEQ ID NO 10
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 10
ccacgtcttg atgacaatat gccatacttg acgac                          35

<210> SEQ ID NO 11
<211> LENGTH: 17
<212> TYPE: DNA
<213> ORGANISM: Artificial Sequence
<220> FEATURE:
<223> OTHER INFORMATION: Designed oligonucleotide for Gal4 protein
      response element

<400> SEQUENCE: 11
cggaggactg tcctccg                                              17

<210> SEQ ID NO 12
<211> LENGTH: 20
<212> TYPE: DNA
<213> ORGANISM: Artificial Sequence
<220> FEATURE:
<223> OTHER INFORMATION: Designed oligonucleotide for Lex protein
      response element

<400> SEQUENCE: 12
tactgtatgt acatacagta                                           20

<210> SEQ ID NO 13
<211> LENGTH: 22
<212> TYPE: DNA
<213> ORGANISM: Artificial Sequence
<220> FEATURE:
<223> OTHER INFORMATION: Designed oligonucleotide for Lac I receptor
      protein response element

<400> SEQUENCE: 13
```
gaattgtgag cgcgcacaat tc                                              22

<210> SEQ ID NO 14
<211> LENGTH: 42
<212> TYPE: DNA
<213> ORGANISM: Artificial Sequence
<220> FEATURE:
<223> OTHER INFORMATION: Designed oligonucleotide for Tetracycline
      receptor protein response element

<400> SEQUENCE: 14
tcgagtttac cactccctat cagtgataga gaaaagtgaa ag                         42

<210> SEQ ID NO 15
<211> LENGTH: 12
<212> TYPE: DNA
<213> ORGANISM: Artificial Sequence
<220> FEATURE:
<223> OTHER INFORMATION: Designed oligonucleotide for ZFHD-1 protein
      response element

<400> SEQUENCE: 15
taatgatggg cg                                                         12

<210> SEQ ID NO 16
<211> LENGTH: 5
<212> TYPE: DNA
<213> ORGANISM: Artificial Sequence
<220> FEATURE:
<223> OTHER INFORMATION: Designed oligonucleotide for DNA bound by the
      transcription-active complex formed of any one of
      transcription-conjugate factor selected from ARNT1 to 3 and Sim2
      being transcription-regulation factor

<400> SEQUENCE: 16 acgtg                                                                  5

<210> SEQ ID NO 17
<211> LENGTH: 83
<212> TYPE: DNA
<213> ORGANISM: Artificial Sequence
<220> FEATURE:
<223> OTHER INFORMATION: Synthetic PCR primer

<400> SEQUENCE: 17
cgcgtcgagc tcgggtcgga ggactgtcct ccgactgctc gagtcgagct cgggtcggag      60
gactgtcctc cgactgctcg aga                                             83

<210> SEQ ID NO 18
<211> LENGTH: 83
<212> TYPE: DNA
<213> ORGANISM: Artificial Sequence
<220> FEATURE:
<223> OTHER INFORMATION: Synthetic PCR primer

<400> SEQUENCE: 18
cgcgtctcga gcagtcggag gacagtcctc cgacccgagc tcgactcgag cagtcggagg      60
acagtcctcc gacccgagct cga                                             83

<210> SEQ ID NO 19
<211> LENGTH: 22
<212> TYPE: DNA
<213> ORGANISM: Artificial Sequence
<220> FEATURE:
<223> OTHER INFORMATION: Synthetic PCR primer

```
<400> SEQUENCE: 19
agcttcatcc cacgtgagtc at                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic PCR primer

<400> SEQUENCE: 20
ctagatgact cacgtgggat ga                                              22

<210> SEQ ID NO 21
<211> LENGTH: 23
<212> TYPE: DNA
<213> ORGANISM: Artificial Sequence
<220> FEATURE:
<223> OTHER INFORMATION: Synthetic PCR primer

<400> SEQUENCE: 21
agcttcatcc acacgtgagt cat                                             23

<210> SEQ ID NO 22
<211> LENGTH: 23
<212> TYPE: DNA
<213> ORGANISM: Artificial Sequence
<220> FEATURE:
<223> OTHER INFORMATION: Synthetic PCR primer

<400> SEQUENCE: 22
ctagatgact cacgtgtgga tga                                             23

<210> SEQ ID NO 23
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 23
agcttcatcc aacacgtgag tcat                                            24

<210> SEQ ID NO 24
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 24
ctagatgact cacgtgttgg atga                                            24

<210> SEQ ID NO 25
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 25
ggccatggcg gcgactactg ccaacccga aatga                                 35

<210> SEQ ID NO 26
<211> LENGTH: 35
```

<210> SEQ ID NO 26
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 26
tgagggaagg gaagggagag gaacttttat tctgt                          35

<210> SEQ ID NO 27
<211> LENGTH: 56
<212> TYPE: DNA
<213> ORGANISM: Artificial Sequence
<220> FEATURE:
<223> OTHER INFORMATION: Syntheitc PCR primer

<400> SEQUENCE: 27
cccggcggcc gcccagccac catggcggcg actactgcca accccgaaat gacatc    56

<210> SEQ ID NO 28
<211> LENGTH: 45
<212> TYPE: DNA
<213> ORGANISM: Artificial Sequence
<220> FEATURE:
<223> OTHER INFORMATION: Synthetic PCR primer

<400> SEQUENCE: 28
cccgtctaga acccttatc ctcaccccaa tagttctatt ctgaa                 45

<210> SEQ ID NO 29
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 29
catctctcac ctggactgct gtgaccttca ttcat                           35

<210> SEQ ID NO 30
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 30
cacatgggca tcgacatcac agtatgggtg gcact                           35

<210> SEQ ID NO 31
<211> LENGTH: 56
<212> TYPE: DNA
<213> ORGANISM: Artificial Sequence
<220> FEATURE:
<223> OTHER INFORMATION: Synthetic PCR primer

<400> SEQUENCE: 31
gggcgcggcc gcccagccac catggcttca gacatacctg gatctgtgac gttgcc    56

<210> SEQ ID NO 32
<211> LENGTH: 45
<212> TYPE: DNA
<213> ORGANISM: Artificial Sequence
<220> FEATURE:
<223> OTHER INFORMATION: Synthetic PCR primer

<400> SEQUENCE: 32

```
gggctctaga ctactcagaa aacggtggaa acatgcccag gtcgg         45
```

<210> SEQ ID NO 33
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 33

```
atggacacag acaaagatga ccctcatgga aggtt                   35
```

<210> SEQ ID NO 34
<211> LENGTH: 36
<212> TYPE: DNA
<213> ORGANISM: Artificial Sequence
<220> FEATURE:
<223> OTHER INFORMATION: Syntheitc PCR primer

<400> SEQUENCE: 34

```
tgtttacagc ggccatggca agtcactaaa gtcaac                  36
```

<210> SEQ ID NO 35
<211> LENGTH: 56
<212> TYPE: DNA
<213> ORGANISM: Artificial Sequence
<220> FEATURE:
<223> OTHER INFORMATION: Synthetic PCR primer

<400> SEQUENCE: 35

```
ggggcggccg ccccagccac catggacaca gacaaagatg accctcatgg aaggtt    56
```

<210> SEQ ID NO 36
<211> LENGTH: 45
<212> TYPE: DNA
<213> ORGANISM: Artificial Sequence
<220> FEATURE:
<223> OTHER INFORMATION: Synthetic PCR primer

<400> SEQUENCE: 36

```
gggtctagat gtttacagcg gccatggcaa gtcactaaag tcaac         45
```

<210> SEQ ID NO 37
<211> LENGTH: 34
<212> TYPE: DNA
<213> ORGANISM: Artificial Sequence
<220> FEATURE:
<223> OTHER INFORMATION: Synthetic PCR primer

<400> SEQUENCE: 37

```
agctatgggg tcttccagct cacacatgac agag                    34
```

<210> SEQ ID NO 38
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 38

```
atcaaaggct agagggtcca ctggatgtca ctgaa                   35
```

<210> SEQ ID NO 39
<211> LENGTH: 56
<212> TYPE: DNA
<213> ORGANISM: Artificial Sequence
<220> FEATURE:
<223> OTHER INFORMATION: Synthetic PCR primer

<400> SEQUENCE: 39
gggcgcggcc gcccagccac catggggtct tccagctcac acatgacaga gtttcc        56

<210> SEQ ID NO 40
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 40
atcaaaggct agagggtcca ctggatgtca ctgaa        35

<210> SEQ ID NO 41
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 41
gtctaatatg cccggagccg aggcgcgatg aagga        35

<210> SEQ ID NO 42
<211> LENGTH: 36
<212> TYPE: DNA
<213> ORGANISM: Artificial Sequence
<220> FEATURE:
<223> OTHER INFORMATION: Synthetic PCR primer

<400> SEQUENCE: 42
tcacctcccg ttggtgatga tgaccgaggc gcccag        36

<210> SEQ ID NO 43
<211> LENGTH: 56
<212> TYPE: DNA
<213> ORGANISM: Artificial Sequence
<220> FEATURE:
<223> OTHER INFORMATION: Synthetic PCR primer

<400> SEQUENCE: 43
gggcgcggcc gcccagccac catgaaggag aagtccaaga atgcggccaa gaccag        56

<210> SEQ ID NO 44
<211> LENGTH: 45
<212> TYPE: DNA
<213> ORGANISM: Artificial Sequence
<220> FEATURE:
<223> OTHER INFORMATION: Synthetic PCR primer

<400> SEQUENCE: 44
gggctctaga tcacctcccg ttggtgatga tgaccgaggc gccca        45

<210> SEQ ID NO 45
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 45
gatccaagga gtacaaaagg agaagtacaa atgtc        35

<210> SEQ ID NO 46
<211> LENGTH: 34
<212> TYPE: DNA
<213> ORGANISM: Artificial Sequence
<220> FEATURE:
<223> OTHER INFORMATION: Synthetic PCR primer

<400> SEQUENCE: 46
tactgcatct catgaaactg ctggaacttt ccct                    34

<210> SEQ ID NO 47
<211> LENGTH: 40
<212> TYPE: DNA
<213> ORGANISM: Artificial Sequence
<220> FEATURE:
<223> OTHER INFORMATION: Synthetic PCR primer

<400> SEQUENCE: 47
gggcgggatc cccagccacc atgttgttta ccgtaagctg              40

<210> SEQ ID NO 48
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 48
ctactgtggt tgaaccttgg                                    20

<210> SEQ ID NO 49
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 49
ctagaaattt gtacgtgcca caga                               24

<210> SEQ ID NO 50
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 50
tctgtggcac gtacaaattt ctag                               24

<210> SEQ ID NO 51
<211> LENGTH: 18
<212> TYPE: DNA
<213> ORGANISM: Artificial Sequence
<220> FEATURE:
<223> OTHER INFORMATION: Synthetic PCR primer

<400> SEQUENCE: 51
caagtccacg tgcaggga                                      18

<210> SEQ ID NO 52
<211> LENGTH: 18
<212> TYPE: DNA
<213> ORGANISM: Artificial Sequence
<220> FEATURE:
<223> OTHER INFORMATION: Synthetic PCR primer

<400> SEQUENCE: 52
tccctgcacg tggacttg                                                    18

<210> SEQ ID NO 53
<211> LENGTH: 41
<212> TYPE: DNA
<213> ORGANISM: Artificial Sequence
<220> FEATURE:
<223> OTHER INFORMATION: Synthetic PCR primer

<400> SEQUENCE: 53
gggcgctgca gcccagccac catgtaccga tccaccaagg g                          41

<210> SEQ ID NO 54
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 54
aatctcggcg ttgatctggt                                                  20

<210> SEQ ID NO 55
<211> LENGTH: 54
<212> TYPE: DNA
<213> ORGANISM: Artificial Sequence
<220> FEATURE:
<223> OTHER INFORMATION: Synthetic PCR primer

<400> SEQUENCE: 55
ctagcctaga aatttgtacg tgccacagac tagaaatttg tacgtgccac agag            54

<210> SEQ ID NO 56
<211> LENGTH: 54
<212> TYPE: DNA
<213> ORGANISM: Artificial Sequence
<220> FEATURE:
<223> OTHER INFORMATION: Synthetic PCR primer

<400> SEQUENCE: 56
ctagctctgt ggcacgtaca aatttctagt ctgtggcacg tacaaatttc tagg            54

<210> SEQ ID NO 57
<211> LENGTH: 56
<212> TYPE: DNA
<213> ORGANISM: Artificial Sequence
<220> FEATURE:
<223> OTHER INFORMATION: Synthetic PCR primer

<400> SEQUENCE: 57
ctttagccac gtgacagtgt aagcacacgt gggccctcaa gtccacgtgc agggac          56

<210> SEQ ID NO 58
<211> LENGTH: 64
<212> TYPE: DNA
<213> ORGANISM: Artificial Sequence
<220> FEATURE:
<223> OTHER INFORMATION: Synthetic PCR primer

<400> SEQUENCE: 58
tcgagtccct gcacgtggac ttgagggccc acgtgtgctt acactgtcac gtggctaaag      60
gtac                                                                   64

```
<210> SEQ ID NO 59
<211> LENGTH: 7408
<212> TYPE: DNA
<213> ORGANISM: Mus musculus
<220> FEATURE:
<221> NAME/KEY: Intron
<222> LOCATION: (1594)..(2347)
<220> FEATURE:
<221> NAME/KEY: exon
<222> LOCATION: (2348)..(2499)
<220> FEATURE:
<221> NAME/KEY: Intron
<222> LOCATION: (2500)..(2673)
<220> FEATURE:
<221> NAME/KEY: exon
<222> LOCATION: (2674)..(2776)
<220> FEATURE:
<221> NAME/KEY: Intron
<222> LOCATION: (2777)..(2886)
<220> FEATURE:
<221> NAME/KEY: exon
<222> LOCATION: (2887)..(3160)
<220> FEATURE:
<221> NAME/KEY: Intron
<222> LOCATION: (3161)..(3347)
<220> FEATURE:
<221> NAME/KEY: exon
<222> LOCATION: (3348)..(3457)
<220> FEATURE:
<221> NAME/KEY: Intron
<222> LOCATION: (3458)..(3784)
<220> FEATURE:
<221> NAME/KEY: exon
<222> LOCATION: (3785)..(3920)
<220> FEATURE:
<221> NAME/KEY: Intron
<222> LOCATION: (3921)..(4050)
<220> FEATURE:
<221> NAME/KEY: exon
<222> LOCATION: (4051)..(5480)
<220> FEATURE:
<221> NAME/KEY: Intron
<222> LOCATION: (5481)..(6138)

<400> SEQUENCE: 59
aaggaaaaaa aaaaaaagaa aggtgtatgt tgtgcgctca ctcagtgaca agtgcacagg      60
cagaacgagg agccctggag ctaaagatgg agcaagaatt gaagggagat ggggagggga     120
ctctggcaga attaaagggt cttgggtagg tgcagcagcc actgagggca cagcagaccc     180
tggctacttg gcagcctccc cctcttcccg gctgaagcag tggggagagc tttctagagc     240
tgtgcggagg ccggtaggcc ccgcccgccg ctgccgccgc cgcagccgcc ggaggattcc     300
tgtcctaata tggagctggg attccccgg ccccgccccc gccccccagc ccgccggaga      360
gactggggct cgcaagaggg cgggggaaca gctcgtcttg ggggctgaca gcgggaggg     420 gatcgtggga gaggttcaaa cacacatcca gatcctcacc aggccctggg tctttgcctc      480
agtttccccg acaggtggct aagatgaact aatagaggaa aaaggaatcc ctgcagatca      540
cagtggagat gtttgtgttc ctatggtgct aaggaaatat gatcaagacc gaattcaagt      600
ggtctcttct ccacaggacc accattccac cctatcctgg agatttagac cctcaggtca      660
gggcatggag gcgaagaagg aattatttat ttgaaactgg ctaagggact ttcagattga      720 atagaccccca gaaagacccc ccagttgtga cctagcccct ccccaaaagc caaggaaagt      780
ccctcatgta atttcgaccc ctgcctggca gatgcggcaa aattggcaga ggaccaagcc      840
ccttctcatc ctttgcctcc ttagaaaaat ctatgttgat agcagcctcg ctttgccttc      900
tacaaactct cttgttaagg gcttcagacc accctaatcc atgtactgtt cctcctccta      960
```

-continued

```
atagaatgta atggaaaacc tgggtccctg cacccattc ctggctctgc acagctcttg    1020
ccagccggcc ccctctgcac cctcccttct ccccttccc ccgcccctc cctctcccgt     1080 tcgacgtcac gggatgacgt cggaagtctg ggagggagga ggagcacccc cctcccag     1140 ccagtggctc cctctgcagc ttgctttagc ccagcctccc gcctcccgct gcccccccg    1200 tctctaaaaa cgagcccccc acgcctgtca ggagctatat aaggcggatc gaggcaggcg   1260
aggggggcag cgctgccgag cggagcccag gagtggagcg agagcgagca agagcctgag   1320
cgaaaagacc gggaagcaag gaagaggaag cctccggtgc atcgggaaag gatcgcaggt   1380
gctcgggagc cggagctgga gctccacagc cggcagtc atg tac cga tcc acc aag  1436
                                      Met Tyr Arg Ser Thr Lys
                                        1               5 ggc gcc tcc aag gcg cgc cgc gac cag atc aac gcc gag att cgg aac   1484
Gly Ala Ser Lys Ala Arg Arg Asp Gln Ile Asn Ala Glu Ile Arg Asn
         10                  15                  20 ctc aag gag ctg ctg ccg ttg gct gaa gcg gac aag gtc cgg ctg tcc   1532
Leu Lys Glu Leu Leu Pro Leu Ala Glu Ala Asp Lys Val Arg Leu Ser
     25                  30                  35 tac ctg cac atc atg agt ctt gcc tgc atc tac act cgc aag ggt gtc   1580
Tyr Leu His Ile Met Ser Leu Ala Cys Ile Tyr Thr Arg Lys Gly Val
 40                  45                  50 ttc ttt gct gga g gtgagcagct tgggctaccg gagaccagag ctgacgggga      1633
Phe Phe Ala Gly
55 ccagggatgg aggagctgag ggaatgtgct aaaactgccg cttgtctagc acagcgtgct   1693 ggaagcctgt ggagagaagg gacttgaggg gaccctggac ttcctacttt tcttctgag    1753 ctccatctag actagcctaa acgatagtcc tagcactgga tttgtgtgag atagagcgct   1813 aaaacagaat ggtccaggct cccattgcct cagaggcact ccaggaatcc ggggagggta   1873 cggaaggaag cctggcaagc tacagggaaa gcctgcaaag gcaaagtatg aggaagagta   1933 gcttgtgcta gaaaatgctg agagggtctt tctatgcgct ctggagctgt tcgacgtcct   1993 gaagccatca ccctttctgg cgctgcccgc ggtgctgaaa tggccatagc ccttttcgc    2053 aggagctgtc cgcggtgctg aatcccagtc ctttcgggag agctctgtcc acagtgctga   2113 cagcagaggg ctgctgaggt tccggccagg cttggaagtc caggggctcc ctggctagat   2173 agttttagca acaggtctcc tggccaagat ccacaagcat agggtcaaca ggtgttggca   2233 gaaataggtc tatgggaatt tcctgtgtct tctccaagac tcaaaagatg ttctcttat    2293 ttctgtgttg tccctgattc ttatcctgac tcaccacatc ttctcaccct acag gc     2349
                                                               Gly act cct ttg gct ggc ccc acc ggg ctt ctc tct gct caa gag ctt gaa   2397
Thr Pro Leu Ala Gly Pro Thr Gly Leu Leu Ser Ala Gln Glu Leu Glu
60                  65                  70                  75 gac att gtg gca gca cta cct gga ttt ctc ctt gta ttc aca gct gag   2445
Asp Ile Val Ala Ala Leu Pro Gly Phe Leu Leu Val Phe Thr Ala Glu
             80                  85                  90 ggg aag ttg cta tac ctg tcg gag agt gtg agc gag cat ctg ggc cac   2493
Gly Lys Leu Leu Tyr Leu Ser Glu Ser Val Ser Glu His Leu Gly His
                 95                  100                 105 tct atg gtgagtacta aaagtccttg catctcaagt tggggtatat gtgagataaa     2549
Ser Met atgagcctct cactactgaa aacagagtta ttagaggcga gtgtggggga gtcttccta    2609 agaaaaatca ttggttgcag ataggctctt gctgccttca ctaatgatca cttctccttt   2669 ctag gtg gac ctg gtt gcc cag ggc gac agt atc tac gat atc att gac   2718
     Val Asp Leu Val Ala Gln Gly Asp Ser Ile Tyr Asp Ile Ile Asp
```

```
            Val Asp Leu Val Ala Gln Gly Asp Ser Ile Tyr Asp Ile Ile Asp
            110                 115                 120 cct gct gac cat ctc act gtg cgc cag cag ctc acc atg ccc tct gct        2766
Pro Ala Asp His Leu Thr Val Arg Gln Gln Leu Thr Met Pro Ser Ala
125                 130                 135                 140 ctg gat gct g gtaagaacct cctctcggtt cttcagttta ctcctctgct              2816
Leu Asp Ala gccctgccct aactatctac tctcctccaa tgcccaccct cttagtcagt ttttccttt       2876 gctcacctag at  cgc ctt ttc cgt tgt cga ttc aac acc tcc aag tcc         2924
               Asp Arg Leu Phe Arg Cys Arg Phe Asn Thr Ser Lys Ser
                       145                 150                 155 ctc cgg cgc cag agt tca gga aac aaa ctg gtg ctt att cga ggt cga        2972
Leu Arg Arg Gln Ser Ser Gly Asn Lys Leu Val Leu Ile Arg Gly Arg
                160                 165                 170 ttc cat gct cac cca cct ggg gcc tac tgg gca gga aac cct gtg ttc        3020
Phe His Ala His Pro Pro Gly Ala Tyr Trp Ala Gly Asn Pro Val Phe
        175                 180                 185 acc gct ttc tgc gcc cca ctg gag cca aga ccc cgc cct ggc ccc ggc        3068
Thr Ala Phe Cys Ala Pro Leu Glu Pro Arg Pro Arg Pro Gly Pro Gly
190                 195                 200 cct ggc cct ggc cct ggt cct gct tct ctc ttc ctg gcc atg ttc cag        3116
Pro Gly Pro Gly Pro Gly Pro Ala Ser Leu Phe Leu Ala Met Phe Gln
205                 210                 215                 220 agc cgg cat gct aag gac cta gcc cta ctg gac gtt tct gaa ag             3160
Ser Arg His Ala Lys Asp Leu Ala Leu Leu Asp Val Ser Glu Ser
                225                 230                 235 gtaagcccaa agtgttcaaa ctccagtaag aaggaggcc agaaagaagg gaactttaga       3220
ttcgtgatct tagattcagg gcagggagga tggggcttaa gtgggcagag agcatgggag      3280
ggagtgaagt gcatgcattt tgagtaaggt aaacagaaag ctgacctcat catttccacc     3340 ttcccag t gtc cta atc tac ctg ggc ttt gag cgc agc gaa ctg ctc tgt      3390
          Val Leu Ile Tyr Leu Gly Phe Glu Arg Ser Glu Leu Leu Cys
                  240                 245 aaa tca tgg tat gga ctg cta cac ccc gag gac ctg gcc caa gct tct        3438
Lys Ser Trp Tyr Gly Leu Leu His Pro Glu Asp Leu Ala Gln Ala Ser
250                 255                 260                 265 tct caa cac tac cgc ctg t gtgagtgtcc tgagaggccg tgcataacac             3487
Ser Gln His Tyr Arg Leu
                270 aggaagctgg gagaaagcat gggagacagg ccaggactg gctgtggtcc aaactgatgt       3547 taaggagttt cggaggctac agagtgagct tgaggatgag aagtcaaggc aagaatagga     3607 cagagttaga aaacactgtg tgataaggtc aagtggggag cctagaggta caggttaggg     3667 tagttagaag agaatatgtc atggctccct caattcagtg tagaggtaag aaaggtgggt    3727 gtgtaggtgg tgttgattga tggaccttct aatccggtat tcctttttc tccccag        3784 tg gct gaa agt gga gat att cag gct gaa atg gtg gtg aga ctt caa        3831
   Leu Ala Glu Ser Gly Asp Ile Gln Ala Glu Met Val Val Arg Leu Gln
                 275                 280                 285 gcc aag cat gga ggc tgg aca tgg att tac tgc atg cta tac tca gaa       3879
Ala Lys His Gly Gly Trp Thr Trp Ile Tyr Cys Met Leu Tyr Ser Glu
        290                 295                 300 ggt cca gaa ggc cct ttt act gcc aat aac tac cct atc ag                3920
Gly Pro Glu Gly Pro Phe Thr Ala Asn Asn Tyr Pro Ile Ser
305                 310                 315 gtaagctgta agatacaaga tggcggagag gggaggggag ctgaggtcag catagaagaa     3980
atgcaacgaa gaaaactact ctggtaatgg acagcagacc cttacaagct gccacctctt    4040
```

```
cccttccag t gac acg gaa gcc tgg agc ctc cgc cag cag cta aac tct    4090
          Asp Thr Glu Ala Trp Ser Leu Arg Gln Gln Leu Asn Ser
              320                 325                 330 gaa gac acc cag gca gcc tat gtc cta gga acc cca gct gtg cta ccc    4138
Glu Asp Thr Gln Ala Ala Tyr Val Leu Gly Thr Pro Ala Val Leu Pro
            335                 340                 345 tca ttc tct gag aat gtc ttc tcc cag gag caa tgc tct aat cca ctc    4186
Ser Phe Ser Glu Asn Val Phe Ser Gln Glu Gln Cys Ser Asn Pro Leu
            350                 355                 360 ttt aca cca tcc ctg ggg act cct aga agt gcc agc ttc ccc agg gct    4234
Phe Thr Pro Ser Leu Gly Thr Pro Arg Ser Ala Ser Phe Pro Arg Ala
            365                 370                 375 cct gaa cta ggt gtg atc tca aca cca gaa gag ctt ccc caa ccc tcc    4282
Pro Glu Leu Gly Val Ile Ser Thr Pro Glu Glu Leu Pro Gln Pro Ser
            380                 385                 390 aaa gag ctg gac ttc agt tac ctg cca ttc cct gct agg cct gag cct    4330
Lys Glu Leu Asp Phe Ser Tyr Leu Pro Phe Pro Ala Arg Pro Glu Pro
395                 400                 405                 410 tcc ctc caa gca gac ctg agc aag gat ttg gtg tgt act cca cct tac    4378
Ser Leu Gln Ala Asp Leu Ser Lys Asp Leu Val Cys Thr Pro Pro Tyr
            415                 420                 425 aca ccc cac cag cca gga ggc tgt gcc ttc ctc ttc agc ctc cat gaa    4426
Thr Pro His Gln Pro Gly Gly Cys Ala Phe Leu Phe Ser Leu His Glu
            430                 435                 440 ccc ttc cag act cac ttg ccc cct ccg tcc agc tct ctc caa gaa cag    4474
Pro Phe Gln Thr His Leu Pro Pro Pro Ser Ser Ser Leu Gln Glu Gln
            445                 450                 455 ctg aca cca agt aca gtg act ttc tct gaa cag ttg aca ccc agc agt    4522
Leu Thr Pro Ser Thr Val Thr Phe Ser Glu Gln Leu Thr Pro Ser Ser
            460                 465                 470 gct acc ttc cca gac cca cta acc agt cta caa gga cag ttg aca         4570
Ala Thr Phe Pro Asp Pro Leu Thr Ser Ser Leu Gln Gly Gln Leu Thr
475                 480                 485                 490 gaa agc tca gcc aga agc ttt gaa gac cag ttg act cca tgc acc tct    4618
Glu Ser Ser Ala Arg Ser Phe Glu Asp Gln Leu Thr Pro Cys Thr Ser
            495                 500                 505 tcc ttc cct gac cag cta ctt ccc agc act gcc aca ttc cca gag cct    4666
Ser Phe Pro Asp Gln Leu Leu Pro Ser Thr Ala Thr Phe Pro Glu Pro
            510                 515                 520 ctg ggc agc ccc gcc cat gag cag ctg act cct ccc agc aca gca ttc    4714
Leu Gly Ser Pro Ala His Glu Gln Leu Thr Pro Pro Ser Thr Ala Phe
            525                 530                 535 cag gct cat ctg aac agc ccc agc caa acc ttc cca gag caa ctg agc    4762
Gln Ala His Leu Asn Ser Pro Ser Gln Thr Phe Pro Glu Gln Leu Ser
            540                 545                 550 ccc aat cct acc aag act tac ttc gcc cag gag gga tgc agt ttt ctc    4810
Pro Asn Pro Thr Lys Thr Tyr Phe Ala Gln Glu Gly Cys Ser Phe Leu
555                 560                 565                 570 tat gag aag ttg ccc cca agt cct agc agc cct ggt aat ggg gac tgt    4858
Tyr Glu Lys Leu Pro Pro Ser Pro Ser Ser Pro Gly Asn Gly Asp Cys
            575                 580                 585 aca ctc ctg gcc cta gct cag ctc cgg ggc ccc ctc tct gtg gat gtc    4906
Thr Leu Leu Ala Leu Ala Gln Leu Arg Gly Pro Leu Ser Val Asp Val
            590                 595                 600 ccc ctg gtg ccc gaa ggc ctg ctc aca cct gag gcc tct cca gtc aag    4954
Pro Leu Val Pro Glu Gly Leu Leu Thr Pro Glu Ala Ser Pro Val Lys
            605                 610                 615 caa agt ttc ttc cac tac aca gag aaa gag caa aat gag ata gat cgt    5002
Gln Ser Phe Phe His Tyr Thr Glu Lys Glu Gln Asn Glu Ile Asp Arg
```

```
                620              625               630
ctc att cag cag atc agc cag ttg gct cag ggc gtg gac agg ccc ttc      5050
Leu Ile Gln Gln Ile Ser Gln Leu Ala Gln Gly Val Asp Arg Pro Phe
635                 640                 645                 650 tca gct gag gct ggc act ggg ggg ctg gag cca ctt gga ggg ctg gag      5098
Ser Ala Glu Ala Gly Thr Gly Gly Leu Glu Pro Leu Gly Gly Leu Glu
                655                 660                 665 ccc ctg aac cct aac ctg tcc ctg tca ggg gct gga ccc cct gtg ctt      5146
Pro Leu Asn Pro Asn Leu Ser Leu Ser Gly Ala Gly Pro Pro Val Leu
            670                 675                 680 agc ctg gat ctt aaa ccc tgg aaa tgc cag gag ctg gac ttc ctg gtt      5194
Ser Leu Asp Leu Lys Pro Trp Lys Cys Gln Glu Leu Asp Phe Leu Val
        685                 690                 695 gac cct gat aat tta ttc ctg gaa gag acg cca gtg gaa gac atc ttc      5242
Asp Pro Asp Asn Leu Phe Leu Glu Glu Thr Pro Val Glu Asp Ile Phe
    700                 705                 710 atg gat ctt tct act cca gac ccc aat ggg gaa tgg ggt tca ggg gat      5290
Met Asp Leu Ser Thr Pro Asp Pro Asn Gly Glu Trp Gly Ser Gly Asp
715                 720                 725                 730 cct gag gca gag gtc cca gga ggg acc ctg tca cct tgc aac aac ctg      5338
Pro Glu Ala Glu Val Pro Gly Gly Thr Leu Ser Pro Cys Asn Asn Leu
                735                 740                 745 tcc cca gaa gat cac agc ttc ctg gag gac ttg gcc acc tat gaa acc      5386
Ser Pro Glu Asp His Ser Phe Leu Glu Asp Leu Ala Thr Tyr Glu Thr
            750                 755                 760 gcc ttt gag aca ggt gtc tca aca ttc ccc tac gaa ggg ttt gct gat      5434
Ala Phe Glu Thr Gly Val Ser Thr Phe Pro Tyr Glu Gly Phe Ala Asp
        765                 770                 775 gag ttg cat caa ctc cag agc caa gtt caa gac agc ttc cat gaa g        5480
Glu Leu His Gln Leu Gln Ser Gln Val Gln Asp Ser Phe His Glu
        780                 785                 790 gtaagtctag cctgaatgtc caagagccct gcccttctaa tcagacattg catagattgg    5540
gtgaatcagt ccccaactct gaaactctgt tttattaaga gaacaatatt acctcctact    5600
aagaagagta gtgaggtagg aataatacaa agctttgtgt gaaagatgag tagacctggt    5660
gggcggggga ggtgagctag aaaaacgcga tagacaatcc ctaggcaaaa gcttgaaagc    5720
ttctgagaga cctagaccag acaacaccgt cattttatag acaaaaataa tcaaggcccc    5780
agagttaaag aaactttaag tggcacaaaa attgatagaa gttgatgctt cccccctgaag   5840 gggacccaga gcaacaactg gttaaaatta ggagacagaa agaacaatgc caagccccta    5900
gctccaatct ggcggccttg tgctgtttgt ccaaagctgt ggccacagtt tccctccata    5960
tttgcatatt gcctcttatc tgctgacacc ctggggatca gttcatttgg ctaacacatt    6020
tgacgtccat agactatagc aatattgtac cactgcctga gcccaatgac gcttttactg    6080
aataagcttg actaacatac gcactttctc tcttctctct ctctctcttt ccccacag     6138 at  gga agt gga ggg gaa cca acg ttt tgaataagtc tgtgacttaa            6184
Asp Gly Ser Gly Gly Glu Pro Thr Phe
    795                 800 cgtcttcaag tatggcatat tgtcatcaag acgtggagcc gctctccacc cccccgggac    6244
tgttgggggg attctggggg ccagagggg atatatctga ttctccaggc cctgaaggat     6304
ttagggggga ggtgggaggg taaggagggg gagcaacttt ttaaaatcaa gagacttcga    6364
gcgatcccag tttccatttc aatctgtatt cactcgtagt gagtttcctt gaatggattt    6424
caagcggaga atgggggagt ctcacttcct caccgcgctg ccccatgggc ctgggccagt    6484
tctccactcc taggggcaaa gccacccctg ggctttggtg ggggaaaggc atggcccacc    6544
```

```
tggggctagc ctgtgccccg agggctctt gacacccacg tagaattctc tacaaaccag    6604
taacgggatt tcaattccga cggactctgc cgccctggcg gctcttcctg tgactttgc    6664 gccccgcgcc tggggtgggg ggcgcgaaga gacgctacat tcctttccga tggaggaagg    6724
cagatctgcc gtcacacgtg tgcttgcacg agtgcgtgta cctggtgcgg gactcacccg    6784
gccgccagac cgcctaggct tgcccaggtg gccacctcgt ggtgctgcgg tgactttgta    6844
gccaacttta taataaagtc cagtttgcct ttttggtatc tctggtgtca tgcgctattg    6904
tgaaaaggga agggagggga agggagagat tgaggagccc agataggagg ctggggcagg    6964
agtcacaggt tagacctcct ctcagccctg gtatctctaa gtgagtttgt tcatatctcc    7024
atttgactct gcttggtcca cactgtgcta gaagactaag tacttgtcag aagcagacat    7084
tgcaccaaag acactggagt cttctctctg ccctgggttt atggtgtgat ggggaggaaa    7144
gagcctgggg ctgagcaagt ttgtcactgg tcttggatat gggtttaaag tttctggtca    7204
tttcctgcct ggtctttcag gatattgatt tcctcatgga ggcttagatt ttaaaaatca    7264
gaagctgaaa cctgttacgc ttgcgtaggg ctgttcagtt agcaaatacc caatccactg    7324
caataaattt ccacttcatt gggaaagcaa cccgataacg ggtgttcctc cagttacagg    7384
tgagaaacac atcaaccct cccc                                             7408
```

```
<210> SEQ ID NO 60
<211> LENGTH: 20775
<212> TYPE: DNA
<213> ORGANISM: Mus musculus
<220> FEATURE:
<221> NAME/KEY: Intron
<222> LOCATION: (9769)..(10522)
<220> FEATURE:
<221> NAME/KEY: exon
<222> LOCATION: (10523)..(10674)
<220> FEATURE:
<221> NAME/KEY: Intron
<222> LOCATION: (10675)..(10848)
<220> FEATURE:
<221> NAME/KEY: exon
<222> LOCATION: (10849)..(10951)
<220> FEATURE:
<221> NAME/KEY: Intron
<222> LOCATION: (10952)..(11061)
<220> FEATURE:
<221> NAME/KEY: exon
<222> LOCATION: (11062)..(11335)
<220> FEATURE:
<221> NAME/KEY: Intron
<222> LOCATION: (11336)..(11522)
<220> FEATURE:
<221> NAME/KEY: exon
<222> LOCATION: (11523)..(11632)
<220> FEATURE:
<221> NAME/KEY: Intron
<222> LOCATION: (11633)..(11959)
<220> FEATURE:
<221> NAME/KEY: exon
<222> LOCATION: (11960)..(12095)
<220> FEATURE:
<221> NAME/KEY: Intron
<222> LOCATION: (12096)..(12225)
<220> FEATURE:
<221> NAME/KEY: exon
<222> LOCATION: (12226)..(13655)
<220> FEATURE:
<221> NAME/KEY: Intron
<222> LOCATION: (13656)..(14313)

<400> SEQUENCE: 60
tctcctgatt tttaaagccc ctctgtcttt cctggccccg cttggcctcc ctgaagatgc    60
```

-continued

```
cctgccctct gcatacctag ggccaatagg agtgatgagc ccatgtcatg tctgctctgg      120
gattctaatg acccaatccc tacaccagac acacaaggca tggacatctg ctcacctgta      180
ggctccatgt cactgggtac acgcaggtga tattacagac aagtgtaaag cttcggtctg      240
tggtggcctg caggtttgtg tgtacctagg tagaagagga agtgaggagg caccagtcag      300
aagcaactct gagaaacagg agccagaatt taagctgggt aagaacatga agatggccaa      360
aggattgcaa ttgttggccc ctggagaaca cactgggact ggtcttggat gttctgttct      420
gtactggagg gatatgggat gcctgctgac acacaggaag ggtctgaacc cagaccctca      480
gggtcactag gtatgcgtac ctcagtttcc taaggctcat tgacttcttt gttcgtttat      540
tcggagaaca gcacctattc tggccacctc cataaggagg gtttcaggaa gcacccaggg      600
ctatgaaccc atcgagccac ttctgtctga ctgcattcaa aacgatagtt tccttaagac      660
aatggccact ccccgtgcat tctccaacac ttactccgtt ccttccgtgc ctatggcttt      720
gttctgagtg ttttgacaaa ttagttcacc tggctcttgt gtcagagctc taacacaaat      780
tgtattctcc tcttcacaac tctatttaat acactggtaa actgaggcat gagaggctgc      840
agtccttacc tcagcagtgt cacagtctgt aacagaggca agacctccct ccaggcccca      900
ccctcttgcc tacctgcct tggctctctt ccggtctcta tgcgaagatc ctatgtattc      960
agacccttct tttaattttt taatggcttt tttatttact ctgtgtgcat gcatgtgagt     1020
gagtgtgtgc cgtggtttat gtgtggcagt cagaggacat cttcggctc ccttccacc      1080 atggaggtcc tggggattga agttaggctg tcaggcttgg cagcaagtgc ctttacctga     1140
ttaaccttgc tgcccacccc taacccttc ttgctggctc ttccattcgg aataaggcaa     1200
accatgccct ttcagcccttc ttttcaccga gaagaattat cttccttctt ttcatcttct    1260 caattttttcc tacaaatata cctggaatgc ttcgatcaga gctgatggca gacaaaggtg    1320
acagctccta cccaggggtc tccaatacaa gccagagaag acagcagctc attaatgaaa    1380
cgaagtgtaa aactgtcacc atcacaactg gcaacagaag cacagggaac cctgggacct    1440
acagctgggg atttgacccg atagagaaga ttttctggag tgatatttga gccaagctat    1500
tgtgaaaaat gaggatcagg tgcaaggaga ggcaaggggc gtgcatgtgt gcacggagct    1560
gcagaaccac aatggaagag ctgcctgtgg ctagaagaga gggacgggga ggaaggaggc    1620
agggtcgggg gttgggggga agatcaccag agtgcagcct gggagaaggc ttagggtggc    1680
tcctcacagt tcttgacatc cttgatgatg gaagctaagc ctggccactt cacctcatag    1740
gacagctcct gcagccatac ctgctgcgta aagaagcctc agctcccttc ccccacagca    1800
ccacctcatt cccatctaat taattgtttg cttttacctt ggctactgct actcaccaca    1860
ccttataaag ccatgagacc acgctcttgc taatctcatc ctccccaccc acccagcaca    1920
gccacgttgg tcagttggcc acttgactcc caagcaacgt ggcgcaaaca cacctcccta    1980
ggaaccccac tgccatatcc ctaggcttgg tcttccccat gttgcagcca ccgagcaccc    2040
cagatgcccc tttccagaca gcatctcatt cagatggctt cctcttaccc tgtggaagct    2100
ccatgatgtt aaagccaagc ttgtgcctct ccccgacccc cgccagtatc caccagagag    2160
gctggcctct ggcctcaatt catcccacag ccctgtgcag tgagcgtgac atccatcccc    2220
acggtccctg tgacagatgc tggcagtatg gcggccagct gaggtcccg tgtgggtggg    2280 caaggaatag catttgagaa gcagaggcag gagggtcaca agttcaaggt tatcctctgc    2340
tatatatgag gatgcatgcg attctttctc aaattttaga aaatgtgcat caaggaagag    2400
```

```
gcacaggtcg ggtgtgaggg cagagggggc aagctagtca cctctagaag atcagcaggg    2460
cagagttccc ttgctgagga aagtcagaca tgaacatgtg aggcagatct agagggcagg    2520
ggccacaccc tcggtttcta tcttcatgcc actgaggcac atggggtccc tggtctgaat    2580
tttatctctg gtccatgaat taattttcct ctcctccttg gagcagatgc ctccagtcag    2640
ccccatcctc aagccttgcc cagataccct caattttctc atccaggttc cagtctctcc    2700
ctcctgccca caccatccct ccccgccctc acctctgctc agcccactcc cctggctctg    2760
accgtttcta tgcgtaggtg gcagcgtgta ccctcttcac aggagatttg ttgatttcat    2820
aaccataaat agataaaatg ttctgagtgc ttccatgagc gagtagaatt gagggagtga    2880
tcacacaatg aaaaggctgt aggagaagga aaacagcctg tggagacaca gctgaaaccg    2940
gcttggtgct gcacaaacca gcactacctg agggcgagct tgccgttgca taagaggtat    3000
accataaaca caggacttgg gactgccaga gaaccttctg gaaaacactt atgagactgc    3060
aagtctgtca attcaaagga acaatatatt aagaaaatct agatttaaaa tgaaaacaga    3120
acgtggaagc caacaaacat ggatttttaa ttctgagttc atctcatttt ggctgtgtga    3180
ctatgagcaa gttctctcatc ctctctggga aggtgtatat tcatctcttg ggtcagacta    3240
gagggaccaa tcatataata tgctcatttt ttcctctaag aaaaagtggt cttctcgatt    3300
acaacttaac ctccaatatg gaacaatttg tcttcccaaa acgcagtccc aagcactaa    3360
ggatggatag ggtaacctgc ttttcattg tcaagtagaa ctcatgttga catggaaatg    3420
ggttatgcac aatcattctt ggatggggag accatatatt catagttaca agaaagcta    3480
gacattagga aggacttccc aagttcttct ccctaagatg ggtaaagaga gtagagagag    3540
gatgtgacag ctcagtttgt tctgagactg gagagctttc cagagagagg gaaagctatt    3600
tctttacctt ctgctctaag ggtggcagga ttttctgtca agggttaggt agtaggtgtt    3660
tgggcttggt gggagctcta gtcccttctg cacttaactc tgtgactgtg tgaagaaggg    3720
caccagccat aagtatgtga atggtctgaa tgtgtcccag taaaacttca ttaatgaaaa    3780
gaaacagcgg accagatttt attcggtgcc atagtgtata ggccccaatc tcgttctaca    3840
cggcaagaga acaagtttga atggggagga atgaaccatg cacagggcac tgccagagcc    3900
ctgctgtctg actttaagtc attgctcact tctgatctta acctcatcga ctatagaatg    3960
aacgtaataa tctcaatcat cagtcctgag acaaatagcta agaggaaggt tagggtggct    4020
aggaaggctg tgtgtcaaag tgaaagaact gacgcctgca agttaacctc tgacctccac    4080
acacagacac catgacacat gtgtgttctc ttcatgtgac aaattaaaaa ttgcaaaata    4140
aaaagtgcct aagagatcag agtaagtctc tctctccctt tactccaccc ctttgagtgg    4200
cactgagtct agcagcacac gaggccacat ccttgtctgc tgcaggtgac ggtggccttc    4260
ttggatggag acaaatattt cattatagtt ggattcttgg tctgtctttc taacatgcgg    4320
tcctcagtga ccccatttct ggagcaagcc cagcacagga ggaaacgagg aatctctctt    4380
cctctccact gtccgggcat ttggcagggt gctagagttc atgtcaggga gcaacatggc    4440
cgcagtggct ggtgccagac cttgggagag gccttcaaga ctcaggctgg gatcagagtc    4500
aggaacagaa agctctgagt tctcccagaa cattcagctc tggtcccagc ttccctgggg    4560
tctccacgaa gcagccacag ctgtggtcca ctgggaacct gcagcccac ccacggcatc    4620
ataaagtgaa agttgtcctg ctcatctgct cagatgatct cggagtgctg catccttcag    4680
cactgattta tctcagaagc cctagcaagg gattcctta ttttctcatt ctgtccctct    4740
tcctcttccc ctccctctcc tttgcttcat ccttccttct cttcctcata ggcatacttg    4800
```

```
tgcagacaaa taccacatgt atgccgacag tcccccgtca catccttgct ccagtatttg    4860
agaaaaggag ccaggagtct ccatgatatt cttaagaatc aaaccctcca ttccaattcc    4920
tcaggaggtc ttcctcctgg acaatctctg aaaaagatgc accatttctc taatagggat    4980
tgaggggtga tgaccctcta gagccccaat aaagccatga agagaggagc agaggacttc    5040
atggtctgct cttgctataa aaaggccttt ttcgggaaaa aaataaagaa aggaatcagc    5100
caatcccttc acgatgccat cacctcttct tggtggtttt tcggggaagg agtgggtggg    5160
tttccatggc aacagatgcg agctctgctc agtaaagaag ggaccttgat attttttctc    5220
tctcattctc tcagttgtgt gtgtgcctgt gtgtatgtgc gtgctacaca tgcctatgcc    5280
cacaccagca attttttag aactaaagaa agcccttcta tcagctcccc aaatatggag    5340
tgatagaaaa ccatgcactc ctgcaggcca gagaaggttc tggatggttc cagagaaggg    5400
tgctcctgtg aacttgtttt cctccattgc agagattgtg tgcagcagag aggcctttgc    5460
aaactgttag aggctaagag ttagaaaaaa ggatgtttgg tggagagagg ggaacaaagg    5520
atagatggtg caaaaaccaa cgaatggcgt cctagtgggc aaccaaaggt gcacggagtc    5580
tcaggaagca cagtcagcac aaaccaccta acgctgaaga aaaggctcaa ggcagactca    5640
tatatggaca caaacacaca gagaggtata aaagcaaata tattaggcaa aaccgcaaaa    5700
ctgcatacaa cacagaaagg cagagactta gagaaataaa acagacaaat aaaaacacag    5760
atgcaggtac tggcagatat gtagacacac aaggatgcag agcctatcat caaaacacag    5820
gcaaatagat acatggatgc agatagataa gtgtatccag acagataggt ttggatgcag    5880
acatagaaca tgcaacacag cctcattcaa gtgcacacac tcgtgtgcgc tcacacacac    5940
actccccttt ccccctttag ttgctcaagc ttcctatagc aggaaggcag atctgcaaat    6000
gctgcatgtt cacccagtaa gtttggctgt gaatatcttg taaccccac ctattgcttc     6060 tacacacaca cacacacaca cacacacaca cacacacaca cacacacacc caaagccccc    6120
tctcccaact ttgtccactt tccataacc aaaggctgtg atacctcccc catctcaggc     6180
ttccaattct gttttgctgc tgctgctgcc gccgcctgcc gcttgggggg ggagagagtg    6240
gggtgactca gccaggccag gatgactcac actgacagta ttttagcag cggccaggag    6300 ctctctagcg tgccagccgc cccctcctc ctgcttgcta tttcggaacc gtcactggtg     6360
atataaatag ctcttctccc acggcctgaa gctgctgcca ggctattttt ggttctgcac    6420
agttaaaaat agtttcatgg aggtgggagg caagaggagt gggagctggc ctagggagag    6480
gagacattgg gggcatacag agcttctcaa cttgaatcag agtagtcgaa ctaagatgat    6540
cccttcccta ccccctccct tgcccctttc tagaaccttc tccccttcca acgttcctta    6600
tccctagtcc atcctcctgg aaaaatccaa ggattcctcc cttgagccca ttttctttc    6660 caagcttaac taattcctag aaccgaggag tcttgacagc cacacctgta aatagcccat    6720
atgtattctc aatgaggagg atgacagcat cgggatgcca ttctcatcta tcccgaggcc    6780
cagctcggct ttgatgtcac aggcaaaacca cgaccattct gagtgggaag gcaacattca    6840
gcaccacgga cagcgacaac atccccccc ccctccccc ttccaggtct gcttaaattg      6900
cttggagacc agctgtggac ccagcagaga gatgcaactt attgtggagg agatatcaag    6960
aacgtctcct ggccagggct taaagcacct gtctgtgagg aagacagggc agagatgaac    7020
cccagagata gaatggttgt ctagcataca cagagccctg gtttcatcct cagctttggg    7080
aaactaatct agaaactcca tcttggattt gcatatggaa agagaatcca aaaccaagg     7140
```

```
gaagagaatg gaacagggag tggtggtgtt gagtggggat atcagagtta ataaggatga   7200
aacatgccag agagaaatac atcctgaaga aaccatttct gtcacccata aggttggaaa   7260
cagtgtctta cagacacaca ccattttctc catctcagct ataccactgg ctggctacat   7320
ggttgtatat gtagatgctt tctatctgaa ctaaaattgt acaaaatatt aggatagggg   7380
ctctacaacc atgaacctct ccccgcccct ccccggcatt actagggagt gcactcaagt   7440
cttgagcatg atagaagtgt gaactcctac taagccatgg ccctggtcac caaagtaccc   7500
tcttcccata cccccctgct ttcactccac gttgcctctc ttgctatcac cccttttccat  7560
gaagaacagg ggtttcttga ccacaaactt ttctccttgg tgtcaaagtt catctctaac   7620
tttctgcagc cagttctgtc cctctctccc aattttttttt tgttttttgt tctgtttgtt   7680
tgtgtgtttt tgtttttga cagggtttt ctctgtgtag ccttggctgt cctgaactc    7740
actttgtaga ccaggctggc ctcgaactca gaaatctgct tgcctctgcc tcccaagtgc   7800
tgggattaaa ggcgtgtgcc accacgcccg gcttccctca acttttttaaa tggtcttgtt   7860
tttcaggctc taaaagtgct tttatatgtt cctactctaa atgaaatttt gggcaaaaag   7920
tttctctagt cctttgtgaa atggttgtgg gataaaaaaa gggctcccat accctgtgta   7980
gacagcaatc gcatgtaagt gacctgaaga aaggtgtgtg tgggggtgtg tgtctggagg   8040
ggtgggggtga tgcaaaggcc acactacaaa gacaagcctg acatgacagg tagttaaacc   8100
aaaggtgcaa attagagggg tgggggtggg gggcgcccac aaagccgaga tagactgtcc   8160
aacgctcaat gaacgaagga aaaaaaaaaa aagaaaggtg tatgttgtgc gctcactcag   8220
tgacaagtgc acaggcagaa cgaggagccc tggagctaaa gatggagcaa gaattgaagg   8280
gagatgggga ggggactctg gcagaattaa agggtcttgg gtaggtgcag cagccactga   8340
gggcacagca gaccctggct acttggcagc ctccccctct tcccggctga agcagtgggg   8400
agagcttct agagctgtgc ggaggccggt aggccccgcc cgccgctgcc gccgccgcag   8460
ccgccggagg attcctgtcc taatatggag ctgggattcc cccggccccg cccccgcccc   8520
ccagcccgcc ggagagactg gggctcgcaa gagggcgggg gaacagctcg tcttgggggc   8580
tgacaagcgg gaggggatcg tgggagaggt tcaaacacac atccagatcc tcaccaggcc   8640
ctgggtctttt gcctcagttt ccccgacagg tggctaagat gaactaatag aggaaaaagg   8700
aatccctgca gatcacagtg gagatgtttg tgttcctatg gtgctaagga aatatgatca   8760
agaccgaatt caagtggtct cttctccaca ggaccaccat tccaccctat cctggagatt   8820
tagaccctca ggtcagggca tggaggcgaa gaaggaatta tttatttgaa actggctaag   8880
ggactttcag attgaataga ccccagaaaa gaccccagt tgtgacctag cccctcccca   8940
aaagccaagg aaagtccctc atgtaatttc gacccctgcc tggcagatgg cggcaaattg   9000
gcagaggacc aagccccttc tcatcctttg cctccttaga aaatctatg ttgatagcag    9060
cctcgctttg ccttctacaa actctcttgt taagggcttc agaccaccct aatccatgta   9120
ctgttcctcc tcctaataga atgtaatgga aaacctgggt ccctgcaccc cattcctggc   9180
tctgcacagc tcttgccagc cggccccctc tgcaccctcc cttctcccccc ttccccgcc   9240
ccctccctct cccgttcgac gtcacgggat gacgtcggaa gtctgggagg gaggaggagc   9300
accccccctc cccagccagt ggctccctct gcagcttgct ttagcccagc ctcccgcctc   9360
ccgctgcccc cccgtctct aaaaacgagc ccccacgcc tgtcaggagc tatataaggc   9420
ggatcgaggc aggcgagggg ggcagcgctg ccgagcggag cccaggagtg gagcgagagc   9480
gagcaagagc ctgagcgaaa agaccgggaa gcaaggaaga ggaagcctcc ggtgcatcgg   9540
```

```
gaaaggatcg caggtgctcg ggagccggag ctggagctcc acagccggca gtc atg       9596
                                                          Met
                                                          1 tac cga tcc acc aag ggc gcc tcc aag gcg cgc cgc gac cag atc aac    9644
Tyr Arg Ser Thr Lys Gly Ala Ser Lys Ala Arg Arg Asp Gln Ile Asn
        5               10                  15 gcc gag att cgg aac ctc aag gag ctg ctg ccg ttg gct gaa gcg gac    9692
Ala Glu Ile Arg Asn Leu Lys Glu Leu Leu Pro Leu Ala Glu Ala Asp
            20              25              30 aag gtc cgg ctg tcc tac ctg cac atc atg agt ctt gcc tgc atc tac    9740
Lys Val Arg Leu Ser Tyr Leu His Ile Met Ser Leu Ala Cys Ile Tyr
        35              40              45 act cgc aag ggt gtc ttc ttt gct gga g gtgagcagct gggctaccg          9788
Thr Arg Lys Gly Val Phe Phe Ala Gly
50              55 gagaccagag ctgacgggga ccagggatgg aggagctgag ggaatgtgct aaaactgccg   9848
cttgtctagc acagcgtgct ggaagcctgt ggagagaagg gacttgaggg gaccctggac   9908
ttcctacttt ttcttctgag ctccatctag actagcctaa acgatagtcc tagcactgga   9968
tttgtgtgag atagagcgct aaaacagaat ggtccaggct cccattgcct cagaggcact  10028
ccaggaatcc ggggagggta cggaaggaag cctggcaagc tacagggaaa gcctgcaaag  10088
gcaaagtatg aggaagagta gcttgtgcta gaaaatgctg agagggtctt tctatgcgct  10148
ctggagctgt tcgacgtcct gaagccatca ccctttctgg cgctgcccgc ggtgctgaaa  10208
tggccatagc ccctttttcgc aggagctgtc cgcggtgctg aatcccagtc ctttcgggag  10268
agctctgtcc acagtgctga cagcagaggg ctgctgaggt tccggccagg cttggaagtc  10328
caggggctcc ctggctagat agttttagca acaggtctcc tggccaagat ccacaagcat  10388
agggtcaaca ggtgttggca gaaataggtc tatgggaatt tcctgtgtct tctccaagac  10448
tcaaaagatg ttctctttat ttctgtgttg tccctgattc ttatcctgac tcaccacatc  10508
ttctcaccct acag gc act cct ttg gct ggc ccc acc ggg ctt ctc tct    10557
              Gly Thr Pro Leu Ala Gly Pro Thr Gly Leu Leu Ser
              60              65                  70 gct caa gag ctt gaa gac att gtg gca gca cta cct gga ttt ctc ctt   10605
Ala Gln Glu Leu Glu Asp Ile Val Ala Ala Leu Pro Gly Phe Leu Leu
            75              80              85 gta ttc aca gct gag ggg aag ttg cta tac ctg tcg gag agt gtg agc   10653
Val Phe Thr Ala Glu Gly Lys Leu Leu Tyr Leu Ser Glu Ser Val Ser
        90              95                  100 gag cat ctg ggc cac tct atg gtgagtacta aaagtccttg catctcaagt      10704
Glu His Leu Gly His Ser Met
            105 tggggtatat gtgagataaa atgagcctct cactactgaa aacagagtta ttagaggcga  10764 gtgtgggggga gtcttcccta agaaaaatca ttggttgcag ataggctctt gctgccttca  10824 ctaatgatca cttctccttt ctag gtg gac ctg gtt gcc cag ggc gac agt    10875
                          Val Asp Leu Val Ala Gln Gly Asp Ser
                              110             115 atc tac gat atc att gac cct gct gac cat ctc act gtg cgc cag cag   10923
Ile Tyr Asp Ile Ile Asp Pro Ala Asp His Leu Thr Val Arg Gln Gln
    120             125             130 ctc acc atg ccc tct gct ctg gat gct g gtaagaacct cctctcggtt        10971
Leu Thr Met Pro Ser Ala Leu Asp Ala
135             140 cttcagttta ctcctctgct gccctgccct aactatctac tctcctccaa tgcccaccct  11031
```

-continued

```
cttagtcagt ttttcctttt gctcacctag at  cgc ctt ttc cgt tgt cga ttc       11084
                                    Arg Leu Phe Arg Cys Arg Phe
                                    Asp
                                    145                 150 aac acc tcc aag tcc ctc cgg cgc cag agt tca gga aac aaa ctg gtg        11132
Asn Thr Ser Lys Ser Leu Arg Arg Gln Ser Ser Gly Asn Lys Leu Val
            155                 160                 165 ctt att cga ggt cga ttc cat gct cac cca cct ggg gcc tac tgg gca        11180
Leu Ile Arg Gly Arg Phe His Ala His Pro Pro Gly Ala Tyr Trp Ala
        170                 175                 180 gga aac cct gtg ttc acc gct ttc tgc gcc cca ctg gag cca aga ccc        11228
Gly Asn Pro Val Phe Thr Ala Phe Cys Ala Pro Leu Glu Pro Arg Pro
    185                 190                 195 cgc cct ggc ccc ggc cct ggc cct ggc cct ggt cct gct tct ctc ttc        11276
Arg Pro Gly Pro Gly Pro Gly Pro Gly Pro Gly Pro Ala Ser Leu Phe
200                 205                 210                 215 ctg gcc atg ttc cag agc cgg cat gct aag gac cta gcc cta ctg gac        11324
Leu Ala Met Phe Gln Ser Arg His Ala Lys Asp Leu Ala Leu Leu Asp
                220                 225                 230 gtt tct gaa ag  gtaagcccaa agtgttcaaa ctccagtaag aagggaggcc            11375
Val Ser Glu Ser
            235 agaaagaagg gaactttaga ttcgtgatct tagattcagg gcagggagga tggggcttaa      11435 gtgggcagag agcatgggag ggagtgaagt gcatgcattt tgagtaaggt aaacagaaag      11495 ctgacctcat catttccacc ttcccag t gtc cta atc tac ctg ggc ttt gag        11547
              Val Leu Ile Tyr Leu Gly Phe Glu
                                     240 cgc agc gaa ctg ctc tgt aaa tca tgg tat gga ctg cta cac ccc gag        11595
Arg Ser Glu Leu Leu Cys Lys Ser Trp Tyr Gly Leu Leu His Pro Glu
    245                 250                 255 gac ctg gcc caa gct tct tct caa cac tac cgc ctg t gtgagtgtcc           11642
Asp Leu Ala Gln Ala Ser Ser Gln His Tyr Arg Leu
260                 265                 270 tgagaggccg tgcataacac aggaagctgg gagaaagcat gggagacagg ccagggactg      11702
gctgtggtcc aaactgatgt taaggagttt cggaggctac agagtgagct tgaggatgag      11762
aagtcaaggc aagaatagga cagagttaga aaacactgtg tgataaggtc aagtggggag      11822
cctagaggta caggttaggg tagttagaag agaatatgtc atggctccct caattcagtg      11882
tagaggtaag aaaggtgggt gtgtaggtgg tgttgattga tggaccttct aatccggtat      11942
tccttttttc tccccag tg  gct gaa agt gga gat att cag gct gaa atg         11991
                      Leu Ala Glu Ser Gly Asp Ile Gln Ala Glu Met
                                  275                 280 gtg gtg aga ctt caa gcc aag cat gga ggc tgg aca tgg att tac tgc        12039
Val Val Arg Leu Gln Ala Lys His Gly Gly Trp Thr Trp Ile Tyr Cys
        285                 290                 295 atg cta tac tca gaa ggt cca gaa ggc cct ttt act gcc aat aac tac        12087
Met Leu Tyr Ser Glu Gly Pro Glu Gly Pro Phe Thr Ala Asn Asn Tyr
    300                 305                 310 cct atc ag  gtaagctgta agatacaaga tggcggagag gggaggggag                12135
Pro Ile Ser
315 ctgaggtcag catagaagaa atgcaacgaa gaaaactact ctggtaatgg acagcagacc      12195 cttacaagct gccacctctt ccctttccag t gac acg gaa gcc tgg agc ctc         12247
                                   Asp Thr Glu Ala Trp Ser Leu
                                                   320 cgc cag cag cta aac tct gaa gac acc cag gca gcc tat gtc cta gga        12295
Arg Gln Gln Leu Asn Ser Glu Asp Thr Gln Ala Ala Tyr Val Leu Gly
325                 330                 335                 340
```

```
acc cca gct gtg cta ccc tca ttc tct gag aat gtc ttc tcc cag gag    12343
Thr Pro Ala Val Leu Pro Ser Phe Ser Glu Asn Val Phe Ser Gln Glu
            345                 350                 355 caa tgc tct aat cca ctc ttt aca cca tcc ctg ggg act cct aga agt    12391
Gln Cys Ser Asn Pro Leu Phe Thr Pro Ser Leu Gly Thr Pro Arg Ser
            360                 365                 370 gcc agc ttc ccc agg gct cct gaa cta ggt gtg atc tca aca cca gaa    12439
Ala Ser Phe Pro Arg Ala Pro Glu Leu Gly Val Ile Ser Thr Pro Glu
        375                 380                 385 gag ctt ccc caa ccc tcc aaa gag ctg gac ttc agt tac ctg cca ttc    12487
Glu Leu Pro Gln Pro Ser Lys Glu Leu Asp Phe Ser Tyr Leu Pro Phe
390                 395                 400 cct gct agg cct gag cct tcc ctc caa gca gac ctg agc aag gat ttg    12535
Pro Ala Arg Pro Glu Pro Ser Leu Gln Ala Asp Leu Ser Lys Asp Leu
405                 410                 415                 420 gtg tgt act cca cct tac aca ccc cac cag cca gga ggc tgt gcc ttc    12583
Val Cys Thr Pro Pro Tyr Thr Pro His Gln Pro Gly Gly Cys Ala Phe
                425                 430                 435 ctc ttc agc ctc cat gaa ccc ttc cag act cac ttg ccc cct ccg tcc    12631
Leu Phe Ser Leu His Glu Pro Phe Gln Thr His Leu Pro Pro Pro Ser
            440                 445                 450 agc tct ctc caa gaa cag ctg aca cca agt aca gtg act ttc tct gaa    12679
Ser Ser Leu Gln Glu Gln Leu Thr Pro Ser Thr Val Thr Phe Ser Glu
            455                 460                 465 cag ttg aca ccc agc agt gct acc ttc cca gac cca cta acc agt tca    12727
Gln Leu Thr Pro Ser Ser Ala Thr Phe Pro Asp Pro Leu Thr Ser Ser
        470                 475                 480 cta caa gga cag ttg aca gaa agc tca gcc aga agc ttt gaa gac cag    12775
Leu Gln Gly Gln Leu Thr Glu Ser Ser Ala Arg Ser Phe Glu Asp Gln
485                 490                 495                 500 ttg act cca tgc acc tct tcc ttc cct gac cag cta ctt ccc agc act    12823
Leu Thr Pro Cys Thr Ser Ser Phe Pro Asp Gln Leu Leu Pro Ser Thr
                505                 510                 515 gcc aca ttc cca gag cct ctg ggc agc ccc gcc cat gag cag ctg act    12871
Ala Thr Phe Pro Glu Pro Leu Gly Ser Pro Ala His Glu Gln Leu Thr
            520                 525                 530 cct ccc agc aca gca ttc cag gct cat ctg aac agc ccc agc caa acc    12919
Pro Pro Ser Thr Ala Phe Gln Ala His Leu Asn Ser Pro Ser Gln Thr
            535                 540                 545 ttc cca gag caa ctg agc ccc aat cct acc aag act tac ttc gcc cag    12967
Phe Pro Glu Gln Leu Ser Pro Asn Pro Thr Lys Thr Tyr Phe Ala Gln
550                 555                 560 gag gga tgc agt ttt ctc tat gag aag ttg ccc cca agt cct agc agc    13015
Glu Gly Cys Ser Phe Leu Tyr Glu Lys Leu Pro Pro Ser Pro Ser Ser
565                 570                 575                 580 cct ggt aat ggg gac tgt aca ctc ctg gcc cta gct cag ctc cgg ggc    13063
Pro Gly Asn Gly Asp Cys Thr Leu Leu Ala Leu Ala Gln Leu Arg Gly
                585                 590                 595 ccc ctc tct gtg gat gtc ccc ctg gtg ccc gaa ggc ctg ctc aca cct    13111
Pro Leu Ser Val Asp Val Pro Leu Val Pro Glu Gly Leu Leu Thr Pro
            600                 605                 610 gag gcc tct cca gtc aag caa agt ttc ttc cac tac aca gag aaa gag    13159
Glu Ala Ser Pro Val Lys Gln Ser Phe Phe His Tyr Thr Glu Lys Glu
            615                 620                 625 caa aat gag ata gat cgt ctc att cag cag atc agc cag ttg gct cag    13207
Gln Asn Glu Ile Asp Arg Leu Ile Gln Gln Ile Ser Gln Leu Ala Gln
            630                 635                 640 ggc gtg gac agg ccc ttc tca gct gag gct ggc act ggg ggg ctg gag    13255
Gly Val Asp Arg Pro Phe Ser Ala Glu Ala Gly Thr Gly Gly Leu Glu
```

-continued

| | |
|---|---|
| cca ctt gga ggg ctg gag ccc ctg aac cct aac ctg tcc ctg tca ggg<br>Pro Leu Gly Gly Leu Glu Pro Leu Asn Pro Asn Leu Ser Leu Ser Gly<br>                    665                            670                        675 | 13303 |
| gct gga ccc cct gtg ctt agc ctg gat ctt aaa ccc tgg aaa tgc cag<br>Ala Gly Pro Pro Val Leu Ser Leu Asp Leu Lys Pro Trp Lys Cys Gln<br>                    680                            685                        690 | 13351 |
| gag ctg gac ttc ctg gtt gac cct gat aat tta ttc ctg gaa gag acg<br>Glu Leu Asp Phe Leu Val Asp Pro Asp Asn Leu Phe Leu Glu Glu Thr<br>                695                            700                        705 | 13399 |
| cca gtg gaa gac atc ttc atg gat ctt tct act cca gac ccc aat ggg<br>Pro Val Glu Asp Ile Phe Met Asp Leu Ser Thr Pro Asp Pro Asn Gly<br>710                            715                            720 | 13447 |
| gaa tgg ggt tca ggg gat cct gag gca gag gtc cca gga ggg acc ctg<br>Glu Trp Gly Ser Gly Asp Pro Glu Ala Glu Val Pro Gly Gly Thr Leu<br>725                            730                            735                        740 | 13495 |
| tca cct tgc aac aac ctg tcc cca gaa gat cac agc ttc ctg gag gac<br>Ser Pro Cys Asn Asn Leu Ser Pro Glu Asp His Ser Phe Leu Glu Asp<br>                    745                            750                        755 | 13543 |
| ttg gcc acc tat gaa acc gcc ttt gag aca ggt gtc tca aca ttc ccc<br>Leu Ala Thr Tyr Glu Thr Ala Phe Glu Thr Gly Val Ser Thr Phe Pro<br>                760                            765                        770 | 13591 |
| tac gaa ggg ttt gct gat gag ttg cat caa ctc cag agc caa gtt caa<br>Tyr Glu Gly Phe Ala Asp Glu Leu His Gln Leu Gln Ser Gln Val Gln<br>          775                        780                        785 | 13639 |
| gac agc ttc cat gaa g gtaagtctag cctgaatgtc caagagccct gcccttctaa<br>Asp Ser Phe His Glu<br>    790 | 13695 |
| tcagacattg catagattgg gtgaatcagt ccccaactct gaaactctgt tttattaaga | 13755 |
| gaacaatatt acctcctact aagaagagta gtgaggtagg aataatacaa agctttgtgt | 13815 |
| gaaagatgag tagacctggt gggcggggga ggtgagctag aaaaacgcga tagacaatcc | 13875 |
| ctaggcaaaa gcttgaaagc ttctgagaga cctagaccag acaacaccgt cattttatag | 13935 |
| acaaaaataa tcaaggcccc agagttaaag aaactttaag tggcacaaaa attgatagaa | 13995 |
| gttgatgctt ccccctgaag gggacccaga gcaacaactg gttaaaatta ggagacagaa | 14055 |
| agaacaatgc caagcccta gctccaatct ggcggccttg tgctgttttgt ccaaagctgt | 14115 |
| ggccacagtt tccctccata tttgcatatt gcctcttatc tgctgacacc ctgggatca | 14175 |
| gttcatttgg ctaacacatt tgacgtccat agactatagc aatattgtac cactgcctga | 14235 |
| gcccaatgac gcttttactg aataagcttg actaacatac gcactttctc tcttctctct | 14295 |
| ctctctcttt ccccacag at gga agt gga ggg gaa cca acg ttt<br>                          Asp Gly Ser Gly Gly Glu Pro Thr Phe<br>                                  795                        800 | 14339 |
| tgaataagtc tgtgacttaa cgtcttcaag tatggcatat tgtcatcaag acgtggagcc | 14399 |
| gctctccacc ccccgggac tgttgggggg attctggggg ccagaggggg atatatctga | 14459 |
| ttctccaggc cctgaaggat ttagggggga ggtgggaggg taaggagggg gagcaacttt | 14519 |
| ttaaaatcaa gagacttcga gcgatcccag tttccatttc aatctgtatt cactcgtagt | 14579 |
| gagtttcctt gaatggattt caagcggaga atgggggagt ctcacttcct caccgcgctg | 14639 |
| ccccatgggc ctgggccagt tctccactcc taggggcaaa gccaccctg ggctttggtg | 14699 |
| ggggaaaggc atgcccacc tgggctagc ctgtgccccg aggggctctt gacacccacg | 14759 |
| tagaattctc tacaaaccag taacgggatt tcaattccga cggactctgc cgccctggcg | 14819 |
| gctcttcctg tgacttttgc gccccgcgcc tgggtgggg ggcgcgaaga gacgctacat | 14879 |

-continued

```
tcctttccga tggaggaagg cagatctgcc gtcacacgtg tgcttgcacg agtgcgtgta    14939
cctggtgcgg gactcacccg gccgccagac cgcctaggct tgcccaggtg gccacctcgt    14999
ggtgctgcgg tgactttgta gccaacttta taataaagtc cagtttgcct ttttggtatc    15059
tctggtgtca tgcgctattg tgaaaaggga agggagggga agggagagat tgaggagccc    15119
agataggagg ctggggcagg agtcacaggt tagacctcct ctcagccctg gtatctctaa    15179
gtgagtttgt tcatatctcc atttgactct gcttggtcca cactgtgcta aagactaag     15239 tacttgtcag aagcagacat tgcaccaaag acactggagt cttctctctg ccctgggttt    15299
atggtgtgat ggggaggaaa gagcctgggg ctgagcaagt tgtcactgg tcttggatat     15359 gggtttaaag ttctggtca tttcctgcct ggtctttcag gatattgatt tcctcatgga     15419
ggcttagatt ttaaaaatca gaagctgaaa cctgttacgc ttgcgtaggg ctgttcagtt    15479
agcaaatacc caatccactg caataaattt ccacttcatt gggaaagcaa cccgataacg    15539
ggtgttcctc cagttacagg tgagaaacac atcaaccct ccccaaatct ggggagctcc     15599
cagatctcaa tgccagcgaa taaccatcat agaccatctc accacagagc tgaggaccag    15659
tcactgggga ggaaatttca gaaaatggtg tttgactcta aactcgtagg ctcaaccca     15719 cagggtgtgg ttagtggagg acaaatgaaa gttaggtggt agaaggacct gacagatcca    15779
atcacgatcc caccttttgt atttggagtg cacctaaagc ccccacttcc tcacaggtca    15839
aaggagggca gcaatcaaga ggcagtgtca gaacaggaca agtctcttcc agctcacgaa    15899
gtgcagtgaa ggcttggtcg gtgcgacctc catttcagtg gtgacccgca gacttagaga    15959
aagccttgtc ctcaaggaga ggacaacaac tccaggctcc agtctttcca cagaagcaca    16019
ggggcacagc cttgaaaacc ctgtagcctc cactcatcct gaagcccagc tgtggagaca    16079
gacaggccct ttggagggtc cttccttcac tgtggagaca gacaggcct ttggagggtc     16139 cttccttcac tgtggagaca gacaggccct ttggagggtc cttccttcac tgtggagaca    16199
ggccctttgg atccttcctt cacagaaagg aaggatccac agggaccttt ccctctttg     16259 atgggtattt gggtggagcc aagaacttcc ctgtcactcc caagaggaac ctgtcttagc    16319
tcagttccct cctcagcaca gggacacgga gatgggagaa tggataaagg tgctgggcca    16379
agcatgatgc tctgatttga tccttgatgg gaagagataa ctgacagttg tcctctgacg    16439
tgtaactgca ctccaggaca tgttacactc acatgtgcac acacacacac tacacacact    16499
acatacacat accatacaca tactatacac aatataccac acacacacat actatacaca    16559
cataccacat acactacaca cagtacacat gctacacata catacacaca ccacacacat    16619
ataccacaca caaacactct acacacacac actacacaca ctacatacat ataccacaca    16679
cacttaccac acatacagta tatacagtac atacatatgc cacacacaca taacacacac    16739
tcacacacac catatatact actaatagaa aataataaaa atttttaaat ggggtggatt    16799
taggaaatga aatttctgtg agaataaagg aaaggcttcc ttgatgtttg gtggtggctg    16859
gcaatagtgt atgctttctt tgtctttgtt tgttgtagtt ttttgttta ttttgctttt     16919 gattttttt ttgttgttgt tgttacttgt ttgttgaaaa cctgcctctg cctcctaagc     16979
actgaattgt cttgggtggt ttttaaaaat taattaatgt tgaaatattt ttttcatttt    17039
tgagacaaga tttctttgtg tagccttagc tgtcttagaa ctagctctgt agactaagct    17099
ggccttaaac ttacagagat ctgcttgctt ctgcctcctg agtgctggga ttaaagtttt    17159 tagttttaa aaaatataaa ttacagatat gcactgtctt tgcatcatgt cctcttgttt     17219
```

```
tgggcttatt tttgttgttg tggtggtgat aagtgatttt ttttgttttgt ttttgttttt   17279 agttttgttt ttcttcagct caggtcaatc tggagttcac tatgtagtcc aaggtggcca   17339 cagactttg caaatccccc tgcctcagcc tcccaggtgc taggattaca aagaaccag    17399 accaactggt cctgtgtgag gaaaataaag tagaagaggc aatactgcca cctgctggaa   17459
ggaaaagaag ctgcttcctt gctggctgct gaggcccttg cagctcagaa tatcttcacc   17519
ttagaatgga gagataaact gagtccctgg gagagaaaag gacttcagga tctgagagtg   17579
agtgatgttc tggaagcaga gtgcatgaga gaaggtgtct taatcattgt agtactgctg   17639
tgagaagaca ccatgaccaa ggtaacataa aataaagcat ttagttgggg acttgcttag   17699
agtttaaaag ggttgctcca tgaccagcag agcagggagc atgggagtat gcaggtagac   17759
acggcactgg agaagtacct gagagcttcc atctgatccc caagatagag gcagagaaa   17819 ccctcaaagc ccacaccccc tccaacaaca aacacctcct gatccttcct aaacagtcca   17879
ccaaatggag actaagcatt cagatatggg gaccattatc atccaaacca ctatggaagg   17939
ctcgagtctg ggaccagac agactgaacc caggagacca aggggatagc ttagtgggta    17999
aaggcgctag ctgccgagct tggagacgca agtccaatcc ctaggttctg tatggtggaa   18059
agaaacggga ttccagtaag tcaccccctg gccttcgcgc acaccatgat gctcatgccc   18119
acacacatac aaatccaaaa gaaagaccga acctaaggat ggttctgctg ttgtacattt    18179
ttcctgtaat agatcatcca tgacacttgc ctgagttctg ggaaaactga acaaacaaga   18239
tgggtggggc cagacagctg tgctctaact gggaacatca caagaggtaa gacagagcct   18299
gagtgctgaa ggcaagagct agggtatcgt gacagagtaa ccggggactg atttatagtg   18359
ccactttctg agaaggtgac actgagcttg ttagcaacag gtgacaacaa agaagagtcc   18419
aacctaaagg aagcatctgt aatgacatta aaacgggaga gtgtctgagc tgcttaagaa   18479
gtacacagga agtgggctga gacaagcagg agaggggctg gagagaaggt cgcccagtac   18539
ttctagacca caataaaaga tgtaggttgc attctggctg agcgtggtag tgcacacctg   18599
caattgcagc ctcaaaaggc cgagggtgga aaatcttgag ctcctggaca gcctgggctc   18659
catagaaaga aaagtctgca acaacagca acaaaaaacc caaaccaaaa accaaagtgc    18719
tggtgtccta gtgagggttc ctattgctat gaggaaaaac aatgatcaaa acaaactgc    18779 ggacgaaagg gtttgtttgc ctggcacttc cacatcacag tccatcattg aaggaatcca   18839
gaacaggaac gcaagcaagg caggaacctg gaggcaggag ccaatgaaga ggtcatgaag   18899
ggttgctgct tatggcttgc tccacatggc tttacagcct gctagatctc agcaccaaca   18959
gcctaccatg agcgtggccc tcctccatca atcactgatt aagaaaatgt cctacacagg   19019
aagggaggaa ggaagagaga gttaggagca tattggatgg ggatagtgac aggataagat   19079
gtagctacta gagtcttctg gtttagatgg tgaatctgcc agaatttgcc actgaaggat   19139
ttagatttag atttaacata acttacaaga ttagcattct agttgttgca cccagagact   19199
gagttaccat tgtttctgaa ctaagtttgt gtgctgtttt tcttcacgcg gtggctcgac   19259
tgggttcaag agagaaaggt acagcggcaa agcctgggtt tgccagatgc gcaccacaaa   19319
ggcagtgggg gtttgaacga tggggctagc acggcagtgg gaactcattg agccgggtgg   19379
agggattttg gagctccagg tcagagagtt tgctgagatg agaacaccag gctgagcca   19439 tgtggcctgc cggtaccttg gcataatgag ggaacttgct gttctttta atatttccca   19499 caacaggtgt tgaaccagca tgttggggaa gaatccacta gaaatgtaag attatgccgg   19559
gcgtggtggt gctcgccttt aatcccagca ctcgggaggc agaggcaggc agatttctga   19619
```

```
gttcgaggcc agcctggtct acaaagtgag ttccaggaca gccagggcta cacagagaaa   19679
ccctgtctcg aaagacaaaa caaaacaaaa caaacaaaac aaaacaaaac gtatgatcat   19739
tagcctgaga gttagagttt tatttgtttg tttgtttgtt tgttatttaa aatgagtagc   19799
tgggtagtgc tgacacaagt catgtggacc caagcgtgga attgaaacaa agactgtaac   19859
tctgaggtcc cctgctgtgg gggctgcagg ctgttctgag tcaggagaag aaggatgaag   19919
ttgcctactt cttagggcag agatggattg aactgtgaat ttataaaatt ggtattattt   19979
gcttttagga aagatttata tctgggtttt gcctgaatca catggggatt ttcgcccact   20039
gttcagaatt aggataggaa aaaaatcagt ccctgactcc aggtagaaaa gacagtgatt   20099
atcgtctgct acaaacaggt atcaattaac tatgtctgtg gctccctgta gagagctcaa   20159
aagatggata ttataacagg tattaataaa attaatgtca cccaggcagt ggtggcacac   20219
gcctttaatc ccagcacttg ggaggcagag gcaggcggat ttctgagttc gaggccagcc   20279
tggtctacag agtgagttcc agcacagcca gggctacaca gagaaaccct atcttgaaaa   20339
aaaaattaaa taaaattaat gtctgtggcc ccagtgctga gcagatagac agtgtaacaa   20399
gatggctgct ctaggcagag agctgaacag gaagatggta tgaagatagt ttgctctaac   20459
acacctcaca ggatgctcaa atcctgtcta tgtgggctcc atgggaatct tttttttaat   20519
taggtatttt cctcatttac atttccaatg ctatcccaaa agtcccccat accctcctcc   20579
caacccccca accacccact cccactttt  ggccctggcg ttcccctgta ctggggcata   20639
taaagtttgc gtgtccaatg ggcctctctt tccagtgatg gctgactagg ccacctttg   20699 atacatatgc agctagagtc aagagctccg gggtactggt tagttcataa tgttgttcca   20759
cctatagggt tgcaga                                                   20775
```